US012680069B2

(12) United States Patent
Stine et al.

(10) Patent No.: US 12,680,069 B2
(45) Date of Patent: Jul. 14, 2026

(54) INTEGRATED CAPSULE SYSTEM FOR REAL-TIME BIOPROCESS MONITORING AND METHOD OF USING THE SAME

(71) Applicant: UNIVERSITY OF MARYLAND, COLLEGE PARK, College Park, MD (US)

(72) Inventors: Justin Stine, Hyattsville, MD (US); Luke Beardslee, Cambridge, MA (US); Reza Ghodssi, Potomac, MD (US); William E. Bentley, Annapolis, MD (US)

(73) Assignee: University of Maryland, College Park, College Park, MD (US)

( * ) Notice: Subject to any disclaimer, the term of this patent is extended or adjusted under 35 U.S.C. 154(b) by 850 days.

(21) Appl. No.: 17/286,262

(22) PCT Filed: Oct. 18, 2019

(86) PCT No.: PCT/US2019/056885
§ 371 (c)(1),
(2) Date: Apr. 16, 2021

(87) PCT Pub. No.: WO2020/081904
PCT Pub. Date: Apr. 23, 2020

(65) Prior Publication Data
US 2022/0041973 A1 Feb. 10, 2022

Related U.S. Application Data

(60) Provisional application No. 62/747,489, filed on Oct. 18, 2018.

(51) Int. Cl.
*C12M 1/36* (2006.01)
*C12M 1/34* (2006.01)

(52) U.S. Cl.
CPC ............ *C12M 41/48* (2013.01); *C12M 41/34* (2013.01)

(58) Field of Classification Search
CPC .............................. C12M 41/48; C12M 41/34
See application file for complete search history.

(56) References Cited

U.S. PATENT DOCUMENTS

| | | | |
|---|---|---|---|
| 6,689,056 B1* | 2/2004 | Kilcoyne | A61B 5/4233 600/300 |
| 8,615,374 B1* | 12/2013 | Discenzo | G06F 15/00 340/521 |
| 2005/0245794 A1* | 11/2005 | Dinsmoor | A61B 5/6882 600/561 |
| 2007/0168127 A1* | 7/2007 | Zaruba | A61B 5/0538 701/500 |
| 2009/0177143 A1* | 7/2009 | Markle | A61B 5/14539 604/66 |
| 2015/0011874 A1* | 1/2015 | Amoako-Tuffour | A61M 31/002 604/503 |
| 2015/0345689 A1* | 12/2015 | Selker | F16L 58/185 422/534 |
| 2017/0124845 A1* | 5/2017 | Potyrailo | G06K 19/0707 |
| 2018/0190096 A1* | 7/2018 | Lundy | G08C 17/02 |

OTHER PUBLICATIONS

Busse, Christoph et al. "Sensors for disposable bioreactors." Engineering in life sciences vol. 17,8 940-952. Aug. 28, 2017, doi: 10.1002/elsc.201700049 (Year: 2017).*

Todtenberg et al., "Autonomous Sensor Capsule for Usage in Bioreactors", IEEE Sensors Journal, 2015, 15 (7): 4093-4102. (Year: 2015).*

Franc et al., "Measurement of Changes in Tissue Metabolism Using a Clark-Type Oxygen Sensor, in Solid-State Sensor", Actuator and Microsystems Workshop, 2002, pp. 177-180. (Year: 2002).*

O'Mara, P et al. "Staying alive! Sensors used for monitoring cell health in bioreactors." Talanta vol. 176 (2018): 130-139. doi: 10.1016/j.talanta.2017.07.088 (Year: 2018).*

Bhadra et al., Wireless Passive Sensor for pH Monitoring Inside a Small Bioreactor, In 2013 IEEE International Instrumentation and Measurement Technology Conference (I2MTC), 2013, pp. 276-279.

Bhadra et al., Fluid Embeddable Coupled Coil Sensor for Wireless pH Monitoring in a Bioreactor, IEEE Transactions on Instrumentation and Measurement, 2014, 63(5):1337-1346.

Franc et al., Measurement of Changes in Tissue Metabolism Using a Clark-Type Oxygen Sensor, in Solid-State Sensor, Actuator and Microsystems Workshop, 2002, pp. 177-180.

Freitas et al., A Brief Review on Biotechnological Process Sensoring, In 2015 12th IEEE International Conference on Electronic Measurement & Instruments (ICEMI), 2015, vol. 3, pp. 1622-1627.

Nasipuri et al., Development of a Wireless Sensor Network for Monitoring a Bioreactor Landfill, in GeoCongress 2006: Geotechnical Engineering in the Information Technology Age, 2006, pp. 1-6.

Todtenberg et al., Estimation of 433 MHz Path Loss in Algae Culture for Biosensor Capsule Application, in 2013 European Microwave Conference, 2013, pp. 712-715.

Todtenberg et al., Wireless Sensor Capsule for Bioreactors, in 2013 IEEE MTT-S International Microwave Workshop Series on RF and Wireless Technologies for Biomedical and Healthcare Applications (IMWS-BIO), 2013, pp. 1-3.

Todtenberg et al., Autonomous Sensor Capsule for Usage in Bioreactors, IEEE Sensors Journal, 2015, 15 (7):4093-4102.

PCT International Search Report and Written Opinion, PCT/US2019/056885, Jan. 15, 2020, 20 pages.

(Continued)

*Primary Examiner* — Gregory S Emch
*Assistant Examiner* — McKenzie A Dunn

(57) ABSTRACT

An apparatus for monitoring a bioprocess parameter. The apparatus includes: a housing; a bioprocess sensor attached to an outer surface of the housing; a power supply contained within the housing; and an electronics module contained within the housing and in communication with the power supply and the sensor, where the electronics module includes a wireless communication unit.

20 Claims, 51 Drawing Sheets

(56) References Cited

OTHER PUBLICATIONS

P. O'Mara et al., Staying alive! Sensors used for monitoring cell health in bioreactors, 176 Talanta. 130-139, https://doi.org/10.1016/j.talanta.2017.07.088 (available online Jul. 29, 2017).

S. Microelectronics, "LIS3MDL Digital output magnetic sensor :," 2017. [Online]. Available: https://www.st.com/resource/en/datasheet/lis3mdl.pdf.

S. Microelectronics, "LPS33HW digital output barometer with water-resistant package," 2017. [Online]. Available: https://www.st.com/resource/en/datasheet/lps33hw.pdf.

K.-Y. Chen, S. N. Patel, and S. Keller, "Finexus: Tracking Precise Motions of Multiple Fingertips Using Magnetic Sensing," in ACM CHI 2016, 2016, pp.

N. Mehmood and S. M. Aziz, "Magnetic sensing technology for in vivo tracking," in 2012 International Conference on Emerging Technologies, 2012, pp. 1-4.

O. Sosnicki, T. Porchez, G. Michaud, N. Bencheikh, and F. Claeyssen, "AC magnetic field detection system applied to motion tracking," Sensoren und Messsyst. 2010, p. 7, 2010.

* cited by examiner

| Device Mode | Device Operation | |
|---|---|---|
| | Write Command | Task |
| OFF | 0 | Device shuts down |
| MEASURE | 1 | Continuous scheduled measurement |
| CALIBRATE | 2 | Single measurement |
| STANDBY | 3 | Apply bias w/o measurement |

Virtual Ground

FIG. 10

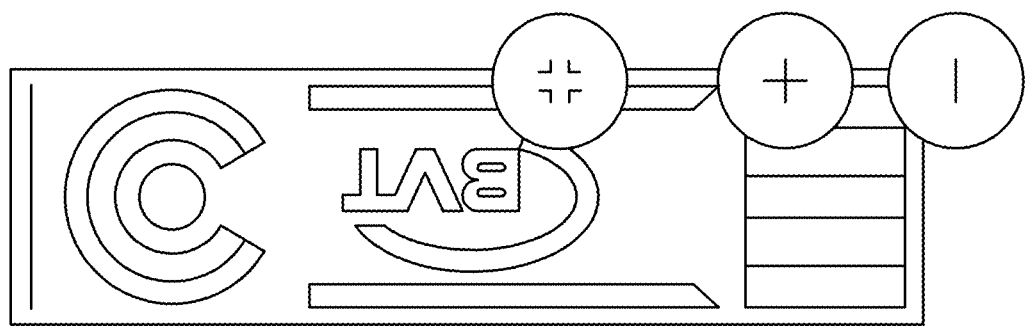
FIG. 11
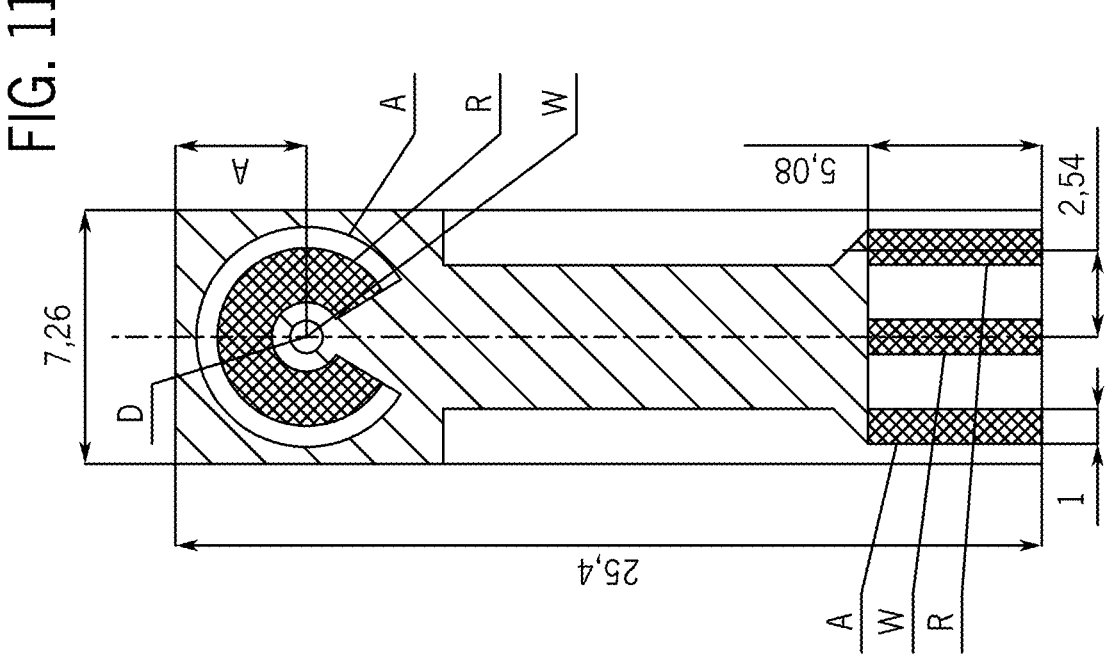

Units are in mm

Silver RE

Epoxy

Gold WE

FEP membrane

9mm

20mm

FIG. 17A 3D-print cover

Simplified Application Schematic

FIG. 23

| Service: Generic Access | Service: Device Information | Service: Service: Custom |
|---|---|---|
| Characteristic: Device Name | Characteristic: Manufacturer Name | Characteristic: Sensor Data |
| Value: bPod<br>Properties: Read-only | Value: Silicon Labs<br>Properties: Read-only | Value: 4 bytes<br>Properties: Read-only |
| Characteristic: Appearance | Characteristic: Model Number | Characteristic: Command |
| Value: unspecified<br>Properties: Read-only | Value: Blue Gecko<br>Properties: Read-only; constant | Value: 1 byte<br>Properties: Read / Write |

FIG. 24

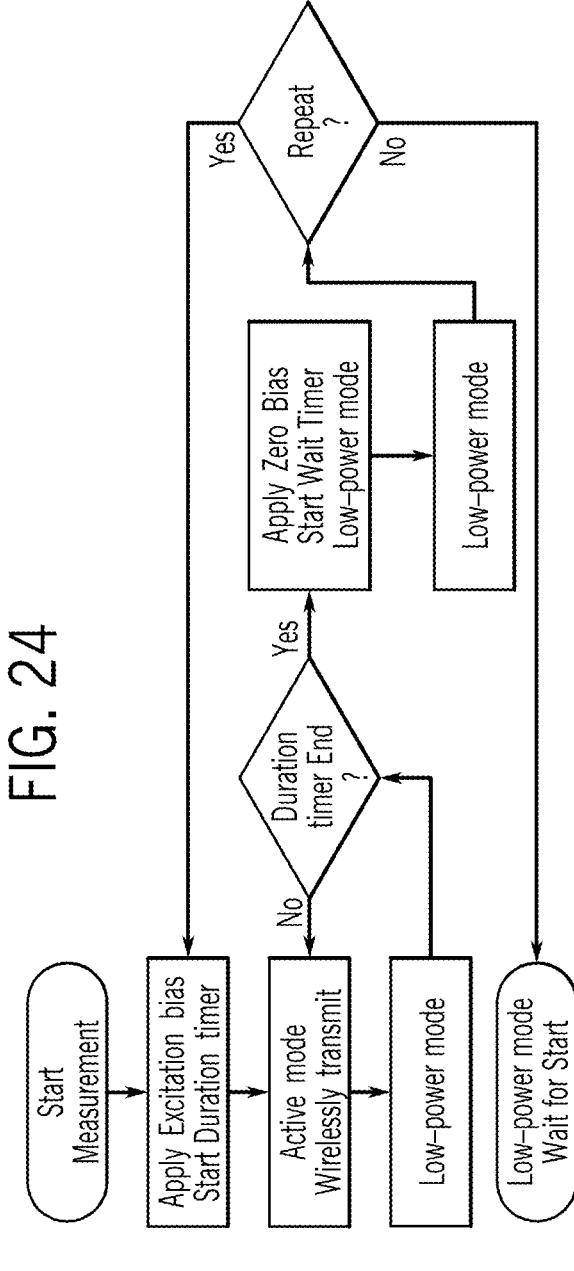

FIG. 25

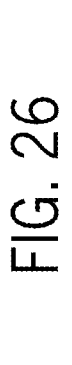
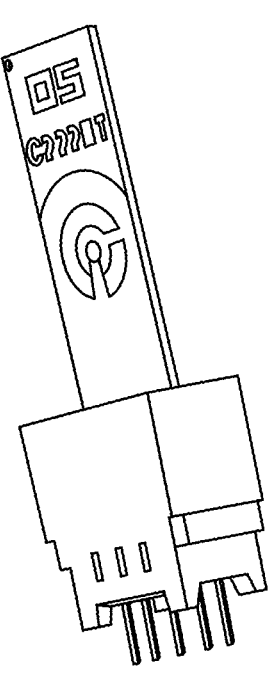
FIG. 26

Generation 1

Generation 2

Generation 3

Voltage Regulator
LM4132

Battery
GM30104H

LMP91000
AFE

MCU

Card Edge Connector
CEC

Bluetooth MCU
BGM121

DO sensor

3D–Printer
Spacer

Cavity

Snap-fit

Sensor
Interface

Ballast Tank 30 mm

Top

Bottom

Battery

Back of board

Micro-controller

Front of board

Sensor

Daughter Board

PCB

Battery

Top View

Side View 9.0 mm x 9.0 mm 5 mm 7.6 mm x 7.6 mm 10 mm

Power Consumption

Transmission Current (Output Power)

- Low-power mode = 1.4 μA
- +0 dbm = 9.7 mAh
- +8 dbm = 27.4 mA
- +18 dbm = 122.7 mA Required Capacity per Week (Measure)

Coincell: Desired Value: 225mAh

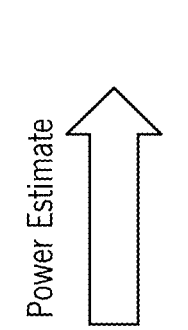

Power Estimate

*Overestimate*

- +0 dbm = 81 mAh
- +8 dbm = 230 mAh
- +18 dbm = 1030 mAh

*Spike pulse Estimate (10 ms)*

- +0 dbm = 16.2 mAh
- +8 dbm = 46 mAh
- +18 dbm = 206 mAh

*Background Bluetooth Pair*

- +0 dbm = 19.6 mAh
- +8 dbm = 55 mAh
- +18 dbm = 245.6 mAh

*Background operation in lower mode = .2 mAh
*All other communication can be accounted for by extending15 sec to 17.85 sec

FIG. 51

INTEGRATED CAPSULE SYSTEM FOR REAL-TIME BIOPROCESS MONITORING AND METHOD OF USING THE SAME

CROSS-REFERENCE TO RELATED APPLICATIONS

This application is a national stage filing under 35 U.S.C. § 371 of International Application No. PCT/US2019/056885, filed Oct. 18, 2019, claims the benefit of U.S. Provisional Patent Application Ser. No. 62/747,489 filed on Oct. 18, 2018, and entitled "Integrated Capsule System for Real-time Bioprocess Monitoring and Method of Using the Same," each of which are incorporated by reference herein in their entirety.

GOVERNMENT SUPPORT

This invention was made with government support under 1624684 awarded by the National Science Foundation. The government has certain rights in the invention.

BACKGROUND OF THE INVENTION

The automation of bioprocess monitoring has afforded unprecedented control over the proliferation and quality of fed-batch cell cultures within bioreactors. In particular, continuous monitoring of a wide range of control parameters such as dissolved oxygen (DO), glucose, temperature, and pH have garnered significant interest for real-time, in situ diagnostic solutions. However, while there has been some work on developing monitoring devices, such systems have continued to have various problems, including poor data transmission through a lossy media and/or power/battery requirements over the process lifetime.

Accordingly, there is a need for improved bioprocess monitoring devices.

SUMMARY OF THE INVENTION

Thus, in various embodiments the presently described invention relates to an integrated device, measurement system, and method of use for providing improved real-time monitoring of bioprocesses.

In one embodiment, the invention provides an apparatus for monitoring a bioprocess parameter. The apparatus includes: a housing; a bioprocess sensor attached to an outer surface of the housing; a power supply contained within the housing; and an electronics module contained within the housing and in communication with the power supply and the sensor, where the electronics module includes a wireless communication unit.

In another embodiment, the invention provides a method for monitoring a bioprocess parameter, including: providing a sensor unit, the sensor unit including: a housing, a bioprocess sensor attached to an outer surface of the housing, a power supply contained within the housing, and an electronics module contained within the housing and in communication with the power supply and the sensor, the electronics module comprising a wireless communication unit; measuring a bioprocess parameter using the bioprocess sensor; storing information identifying the bioprocess parameter in the electronics module; and transmitting the information identifying the bioprocess parameter from the sensor unit using the wireless communication unit.

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 3 shows a schematic of readout circuitry employed in smart marble design for electrochemical measurements.

FIG. 4 shows a cross-sectional view of a Clark electrode contained within a KCl reservoir.

FIG. 10 shows a final dissolved oxygen DO sensor assembly.

FIG. 11 shows a PalmSens glucose electrode with GOx.

FIG. 16A shows thermoset inserts, placement of the electrode, and the sealing of an FEP membrane with a 5 mm O-ring.

FIG. 16B shows a concentric O-ring feature used for creating a leak-proof seal.

FIG. 17A shows an example design of a 3D-printed receptacle sensor interface.

FIG. 17B shows another example design of a 3D-printed receptacle sensor interface.

FIG. 23 shows a GATT profile for bPod device.

FIG. 24 shows a flow diagram for the 'MEASURE' operational state for the bPod.

FIG. 25 shows screenshots of a smartphone app depicting the measurement process from left to right.

FIG. 26 shows a double sided 2.54 mm pitch edge connector with commercial sensor.

FIG. 29 shows an early conceptual representation of the 3D-printed packaging.

FIG. 31A shows generation one of the 3D-printed enclosure.

FIG. 31B shows another view of the generation one of the 3D-printed enclosure.

FIG. 46 shows a conceptual diagram of the printed circuit board (PCB) layout for the electronic module.

FIG. 51 shows power consumption estimates for a bPod device.

DETAILED DESCRIPTION OF EXEMPLARY EMBODIMENTS

Figure 1:
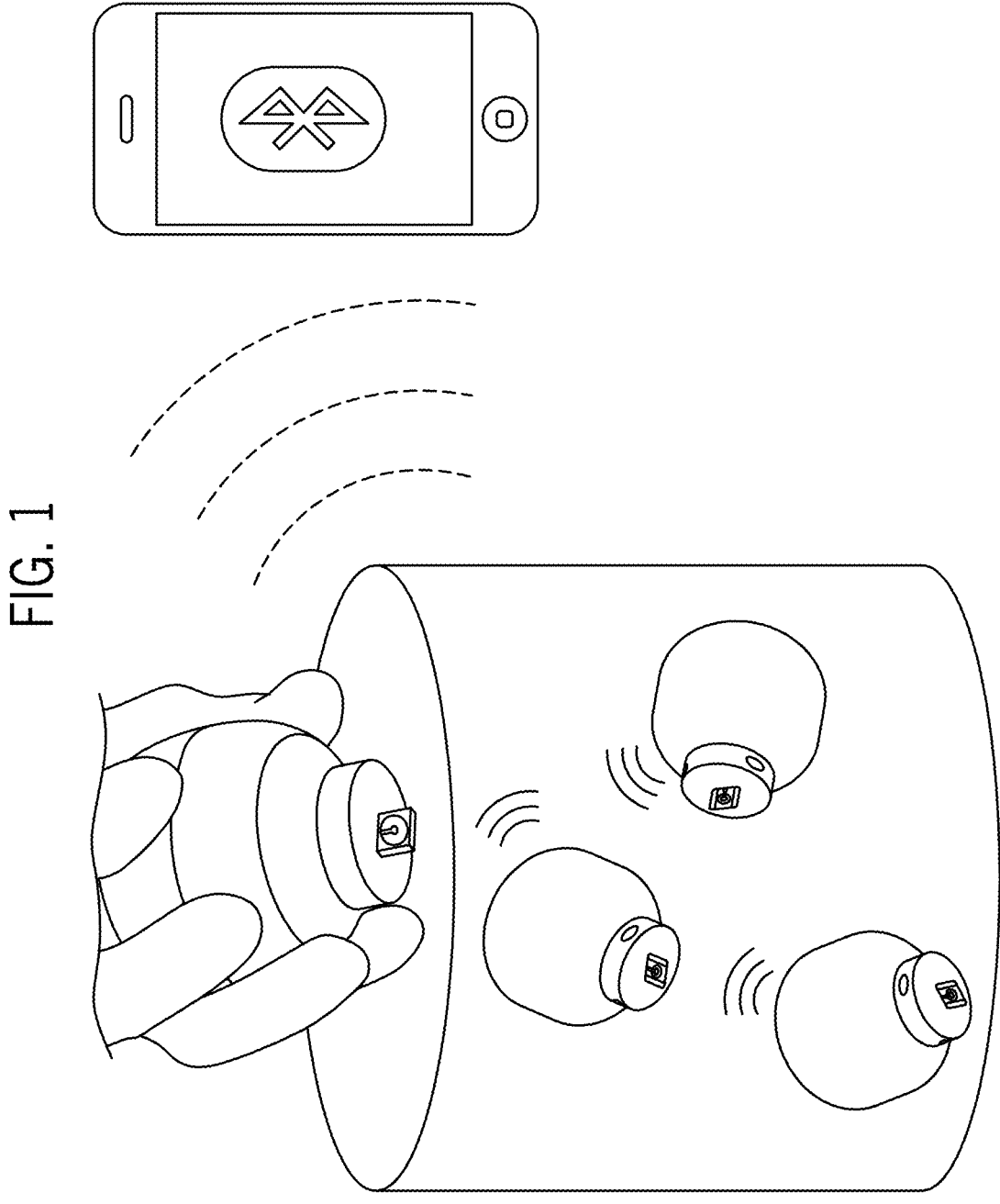
FIG. 1 shows an overview of marble deployment.

In various embodiments, apparatus, systems, and methods are disclosed for providing improved bioprocess monitoring. In certain embodiments, an apparatus for monitoring a bioprocess parameter, for example in a bioreactor environment, is provided (e.g. see FIGS. 1, 2A, 2B). In various embodiments the apparatus, referred to herein as a bioprocess monitoring pod (bPod), may include a housing (which may be leak-resistant or leak-proof), an outer surface of which may have one or more bioprocess sensors attached thereto. Inside the housing may be a power supply and an electronics module coupled to the power supply and the bioprocess sensor.

The bioprocess sensor may be partially housed within the housing of the bPod, with a portion (e.g. a sensor region) of the bioprocess sensor embedded in the housing or projecting through the housing. The bioprocess sensor may be attached to the outer surface of the housing and may communicate with the electronics module via a wired (e.g. a wire that goes through the housing) or wireless connection. In some embodiments the bioprocess sensor may include one or more electrodes (e.g. the Clark electrode disclosed below)

that are separated from the bioreactor environment by a membrane (e.g. a gas-permeable membrane).

The bPod is self-contained, having its own power supply and being equipped to perform wireless communication. The power supply may be a self-contained power source such as a replaceable or rechargeable battery (e.g. one or more coin batteries).

In some embodiments the bPod device electronics module includes a location tracking mechanism for tracking a location of the bPod device. Thus, a combination of one or more of a magnetometer, a pressure sensor, and an RSSI capable receiver system (to obtain signal strength information; RSSI may be integrated into Bluetooth communications) may be used to track the location of the bPod device within the bioreactor.

In certain embodiments the wireless communications may be in the form of a mesh network (e.g. Bluetooth Mesh, which is related to Bluetooth Low Energy) in which the bPod communicates with other bPod units in its vicinity to transfer data locally through the bioreactor and ultimately to a receiver device, for example a receiver that may be located outside the bioreactor. In some embodiments a smartphone may be used to communicate with the bPod devices in a bioreactor environment, for example using a custom app (e.g. for Android, iOS, or other smartphone operating systems).

The bPod may communicate data on a continuous or real-time basis or may communicate at intervals, for example regular intervals (e.g. every second, every 5 seconds, every 10 seconds, every minute, etc.) or at irregular time intervals that may be determined by events such as a change in a parameter reading (e.g. an increase or decrease in a value, a change in a value that exceeds a predetermined threshold amount, etc.), when a particular amount of data has been collected, when a signal is received requesting data, or when another bPod is detected. In some embodiments, the electronics module includes power management capabilities that maximize the life of the power source to extend the deployment time (time without having to replace or recharge the bPod) to at least two weeks.

In various embodiments, the bPod has an approximately neutral buoyancy, which may be adjusted by addition of weights to the device. Neutral buoyancy in certain embodiments refers to a buoyancy which permits the bPod to move at all levels within the liquid environment and not sink to the bottom of the bioreactor or continuously float at the top of the bioreactor. Given that many bioreactor environments include mechanisms for stirring the contents, it is sufficient that the bPod has a substantially neutral buoyancy which permits the device to be driven throughout the environment of the bioreactor by the action of the stirring mechanism of the bioreactor.

To protect the integrity of the electronics module, power supply, and/or other components (e.g. certain electronic parts of the bioprocess sensor), in various embodiments the bPod housing is assembled in a manner that makes the housing leak-resistant or leak-proof. In other words, the bPod is preferably designed in a way so that individual units that are manufactured will be designed to be leak-proof, although with the understanding that some units in large scale manufacturing processes may exhibit some leaks from initial faulty seals or may leak over time as seals erode and the units age, etc. The housing may be made of two parts (e.g. see FIGS. 2A, 2B) that are joined with a leak-proof fitting, for example a fitting with mating parts that include one or more seals (e.g. O-rings) which are held together using compressive forces (e.g. using a bayonet connector).

In some embodiments any connections or points of entry on the housing may have an adhesive (e.g. epoxy) and/or sealant (e.g. silicone-based sealant) added instead of or in addition to any mechanical joining. The housing may include two, three, four, or any other suitable number of components that are joined to form a leak-proof container within which electronics and other components may be sealed. In some embodiments the bPod may be opened and is user-serviceable and in other embodiments the bPod is sealed and is used until no longer functional (e.g. due to failure of the sensor or power supply).

In addition to the joint between housing parts, another potential point of liquid entry that may need to be sealed in a leak-proof manner is where the bioprocess sensor interfaces with the housing. In some embodiments, compressive forces (e.g. using an O-ring pressed between two plates, see FIGS. 2A, 2B) may be used to provide a leak-proof seal that permits a sensor portion of the bioprocess sensor to be exposed to the bioreactor contents while protecting electronic components of the sensor within the housing. Again, adhesives and/or sealants may be used instead of, or in addition to, compressive forces to provide and/or maintain a leak-proof seal.

In certain embodiments, components of the housing may be made of biocompatible materials and individual parts of the housing may be formed using 3D printing, molding, or other suitable manufacturing procedures. The housing may have a "marble" (e.g. approximately spherical) shape or may have other shapes such as a disc, a capsule (e.g. a cylinder with hemispherical ends), various flat-sided solids, or other suitable shapes. In some embodiments the shape may include one or more projections to which are attached components such as bioprocess sensors or communications components (e.g. antennas). The housing may have a size (e.g. in the case of a spherical shaped housing, a diameter) that ranges from 2 cm to 6 cm or more, including sizes of 2.5 cm, 3 cm, 4 cm, or 5 cm. Larger or smaller sizes are possible, with suitable adaptations being made to components such as the bioprocess sensors and electronics to best fit the size of the bPod. In some embodiments the components such as the electronics module may be separated into two or more parts to permit the components to be contained in the bPod in a more compact arrangement, e.g. by stacking of the electronics, power, and sensor components.

Figure 9:
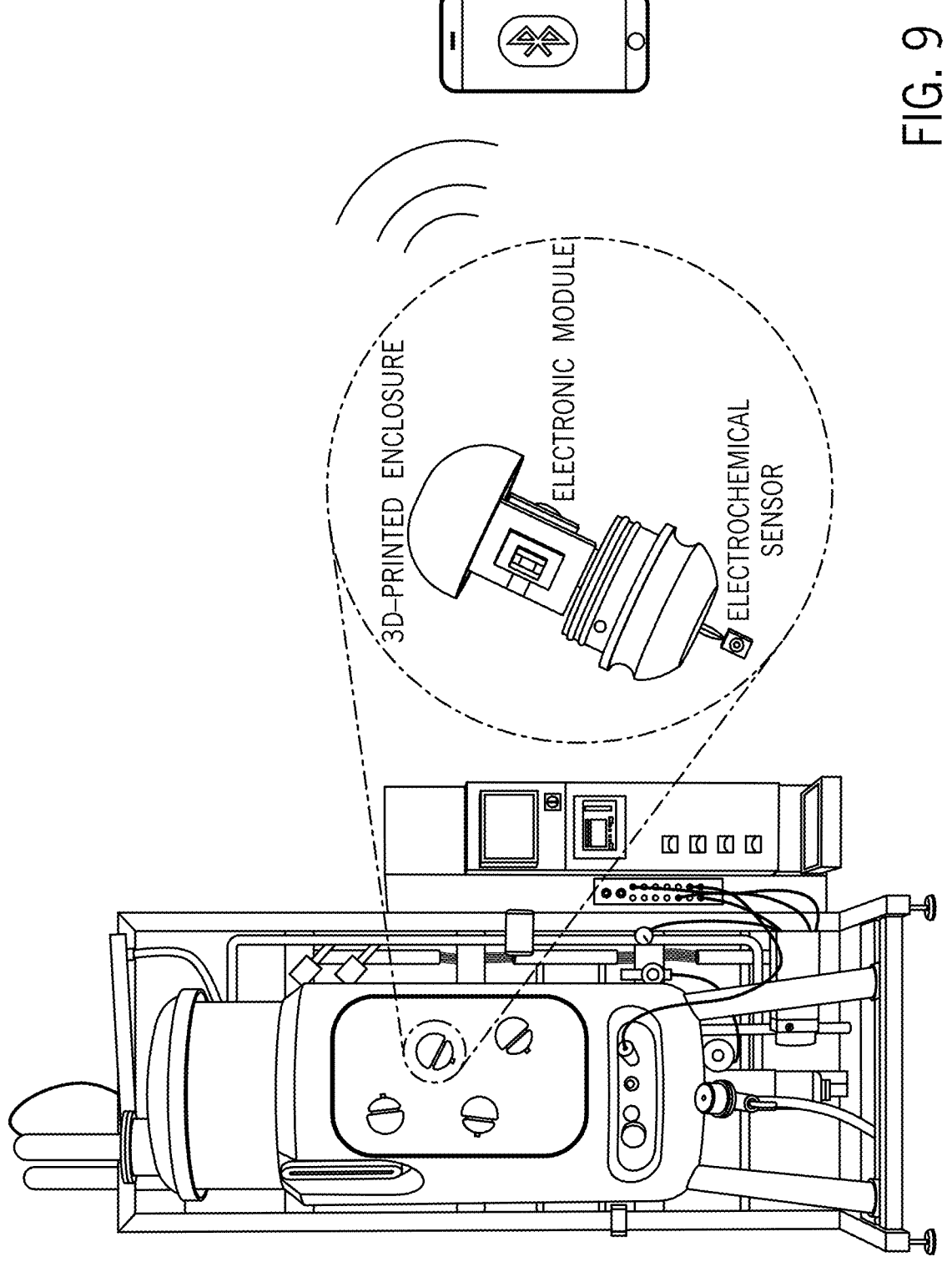
FIG. 9 shows a conceptual overview of fully integrated bio-process online analytical device (bPod).

In various embodiments the bPod device may be part of a method and system for monitoring a bioprocess parameter, e.g. in a bioreactor environment (FIG. 9). For example, multiple bPod devices (e.g. tens, hundreds, or thousands) may be deployed in the same bioreactor environment to obtain information about one or more bioprocess parameters throughout the bioreactor, which may be provided in real time or at other suitable intervals. Each bPod may include one or more bioprocess sensors, which may measure dissolved oxygen (DO), temperature, pH, glucose, and/or pressure. In various embodiments, the bPod-based system and/or method may be implemented based on deploying multiple bPod devices (e.g. tens, hundreds, thousands, or other suitable number) in the same bioreactor environment, where each sensor may be specialized to measure a single or limited number of parameters or each device may be equipped to measure all of the parameters. Each sensor may collect measurements at regular intervals (e.g. several times per second, several times per minute, several times per hour, or other suitable intervals such as one measurement every 1 second, every 10 seconds, every 15 seconds, every 30 seconds, or every 60 seconds) or at irregular intervals that are determined based on external signals or environmental conditions. Each bPod unit may contain sufficient memory to store its own collected data as well as data from many other devices until the data can be transmitted to an external source such as a base unit. The method or system may further include software to manage collecting, processing, and/or displaying the data regarding one or more environmental parameters within the bioreactor, which may be performed in real time or near real time, depending on how quickly the data can be obtained from the bPods.

The multiple devices may each independently communicate with one or more external sources (e.g. a base unit) and/or each bPod device may communicate with other bPod devices, for example using mesh network technology (e.g. Bluetooth Mesh). To the extent that the bioreactor environment may inhibit wireless communications, an advantage of using a mesh network approach is that each device can transfer data to nearby devices and the particular bPod device(s) that are closer to an outer wall or surface of the bioreactor can in turn pass data from one or more devices to the external source. An additional advantage of using multiple devices is redundancy, that is, a failure of a single device will have a limited impact on the overall data that is collected. For example, if tens, hundreds, or thousands of devices are used, even an unusually high failure rate of 10% of the deployed devices would nevertheless leave many functional devices available to provide an ongoing survey of the bioreactor environment with minimal disruption to the overall data collection.

Automation of bioprocessing has afforded greatly improved scalability and control of batch cell culture growth for the biomanufacturing industry. This allows for continuous monitoring of bioprocess parameters such as dissolved oxygen (DO), glucose, temperature, and pH that are instrumental in the proliferation of a targeted substrate or bacteria within a bioreactor. The precise adjustment of these process parameters directly correlates to product yield and quality.

This technology includes a platform encompassing a deployable in situ, real-time sensing module that passively moves with the turbulent flows within the bioreactor while performing electrochemical measurements and wirelessly transmitting the data via Bluetooth Mesh (FIG. 1). To address concerns about wireless communication through a lossy media the module will be capable of forming a wireless mesh network with additional modules to wirelessly pass along bioprocess parameter information through a single routing unit for plastic, glass, and industrial stainless steel varieties of bioreactors. By increasing the number of modules it will be possible to identify possible gradients within the bioreactor. For the first demonstration of this platform dissolved oxygen has been targeted. This parameter has been determined to be important, since low DO saturation has been found responsible for low cell growth and is susceptible to forming hypoxic zones.

Currently, bioreactors are structurally modified to incorporate inline probes that are inserted directly into the bioreactor chamber, or connected via a filtration module. Sensor probes provide data to a feedback controller, which then makes real-time adjustments to the process control parameters. However, a single-point probe measurement may only provide an averaged value for the entire bulk cell media. For example, monoclonal antibodies (mAb) are produced having varied patterns of oxidation, deamidation, glycosylation, charge, etc., which can result in a heterogeneous distribution of the process parameters throughout the bioreactor. Multiplexing of inline probes also requires further modification to the bioreactor which is costly and introduces a higher risk of contamination to the system.

In order to further explore the heterogeneity that exists within bioreactors researchers have investigated in situ modules that can both monitor process parameters and wirelessly communicate with an external receiver. The benefits of such systems include (1) a lower risk of sample contamination, (2) the ability for the module to explore the bioreactor flow and perform localized measurements, and (3) a cost effective pathway towards device scaling and multiplexing of sensor measurements without excess modification to the bioreactor. Some of the daunting challenges associated with portable wireless sensors are limited power supply, biocompatibility with the cell culture, and communication through a lossy media.

RFID sensor tags affixed onto the walls of glass bioreactors have been used by others as a means for low power wireless measurement of temperature. The tags are sterilized, interrogated via a wireless reader, and operate throughout the batch lifecycle. However, this method is limited to glass bioreactors and would require multiple RFID readers to excite a distributed array of RFID tags. Others have integrated a CMOS readout circuit with multiple sensors types in a capsule device operating at the 433 MHZ transmission frequency range for photobioreactor applications in which the module is able to travel throughout the glass perfusion tubes and transmit pH and glucose data to an external receiver. There has also been work by others demonstrating a wireless sensor network for temperature mapping within a bioreactor landfill. However, in that work, the sensing devices are positioned in fixed locations, and only result in a 2D mapping of the temperature.

Referring to FIG. 1, this invention technology may include a platform encompassing a deployable in situ, real-time sensing module that passively moves with the turbulent flows within the bioreactor while performing electrochemical measurements and wirelessly transmitting the data via Bluetooth Mesh. The data can be transmitted to a smartphone. To address concerns about wireless communication through a lossy media the module will be capable of forming a wireless mesh network with additional modules to wirelessly pass along bioprocess parameter information through a single routing unit for both glass and industrial stainless steel varieties of bioreactors. By increasing the number of modules it will be possible to identify possible gradients within the bioreactor.

The invention evokes a microsystems approach to develop a deployable wireless sensor network of smart devices that can be utilized for autonomous, in situ bioprocess monitoring. The platform is divided into five areas of emphasis that have been individually investigated and unified to construct the current prototype. These include device packaging, readout circuitry, wireless communication, sensor efficacy, and development of the software application.

Figures 2A, 2B:
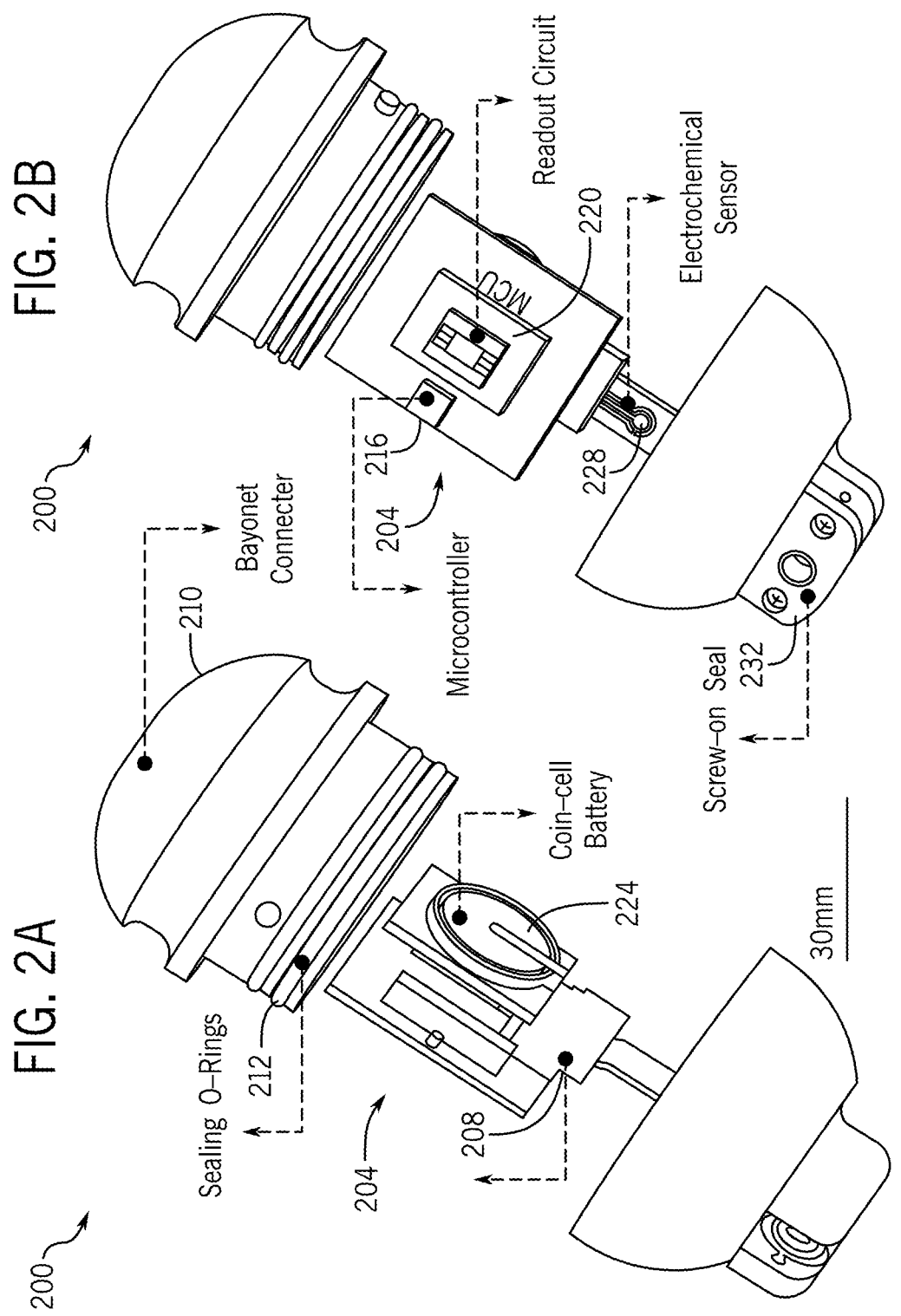
FIG. 2A shows an exploded view of a bPod design.
FIG. 2B shows another exploded view of a bPod design of FIG. 2A.

Referring now to FIGS. 2A and 2B, a bio-process monitoring pod 200 (bPod) is composed of biocompatible 3D printed package (MED610) that isolates the internal electronics from the aqueous environment. The bPod 200 can be the module described above. FIG. 2A is an exploded view of the bPod 200. FIG. 2B is another exploded view of the bPod 200 taken from another side of the bPod 200. The bPod includes a leak-proof package and a hand soldered electronic module 204. The fabricated electrode is isolated in a KCl buffer using a fluorinated ethylene propylene (FEP) membrane and interfaced with the electronics via an edge card reader 208. Commercial O-rings 212 paired with a bayonet connector 210 fitting create the leak-proof seal between the halves of the bPod 200. In one embodiment, the electronic module 204 may include a BGM121 BLE microcontroller 216 (Silicon Laboratories) used for wireless communication and system processing, an LMP 91000 analog front end (AFE) readout circuit 220 (Texas Instruments), and the CR2032 coin cell battery 224 connected with a voltage regulator to provide a 3 volt power supply. The electronics are then interfaced with an electrochemical sensor 228 using the edge card reader 208, and sealed with a screw-on press fit adapter 232. With this approach it is possible develop a suite of sensors and sensor interfaces that accommodate important bioprocessing parameters. For the current iteration a KCl electrolyte has been introduces into the opening of the device and sealed an FEP membrane on top to demonstrate a DO sensor. Further details into these components are described below.

3D-Printed Packaging

The current novel packaging concept was conceived to serve as a prototyping platform, allowing for rapid interchanging of electronic components and interfacing with the microfabricated dissolved oxygen sensor electrode. The module size is current between 60-65 mm in diameter, since most of the internal components are hand soldered as shown in FIGS. 2A and 2B. In the future, the sensor interface may be further refined and the electronic components may be placed onto a PCB, reducing the size of the pod to roughly 25 mm in diameter. The use of 3D-printing enables the incorporation of biocompatible materials for the packaging further minimizing the impact of the device towards cell/bacteria culture viability. Nevertheless, in other embodiments other methods of forming the housing such as PDMS molding may be used and may also incorporate biocompatible materials.

Electronic Module

As previously mentioned, the microcontroller unit (MCU) and the off the shelf AFE chip are integrated to create a smart portable potentiostat. The FC interface of the MCU allows for programming of the LMP91000 register values, enabling precise control over the sensor bias conditions and conversion of the sensor current response to a measurable voltage. The analog voltage is read by the MCU's Analog-to-Digital converter (ADC), which assigns a digital value to the voltage level and transmits the signal wirelessly via Bluetooth. The BGM121 MCU also functions to manage the power consumption of the system. This is accomplished by toggling the energy modes of the device to only provide power to peripherals that are currently in use, as well as scheduling of the device measurements using an application specific algorithm. The MCU can then be controlled monitored remotely via a user interface such as a smart phone.

Figure 3:
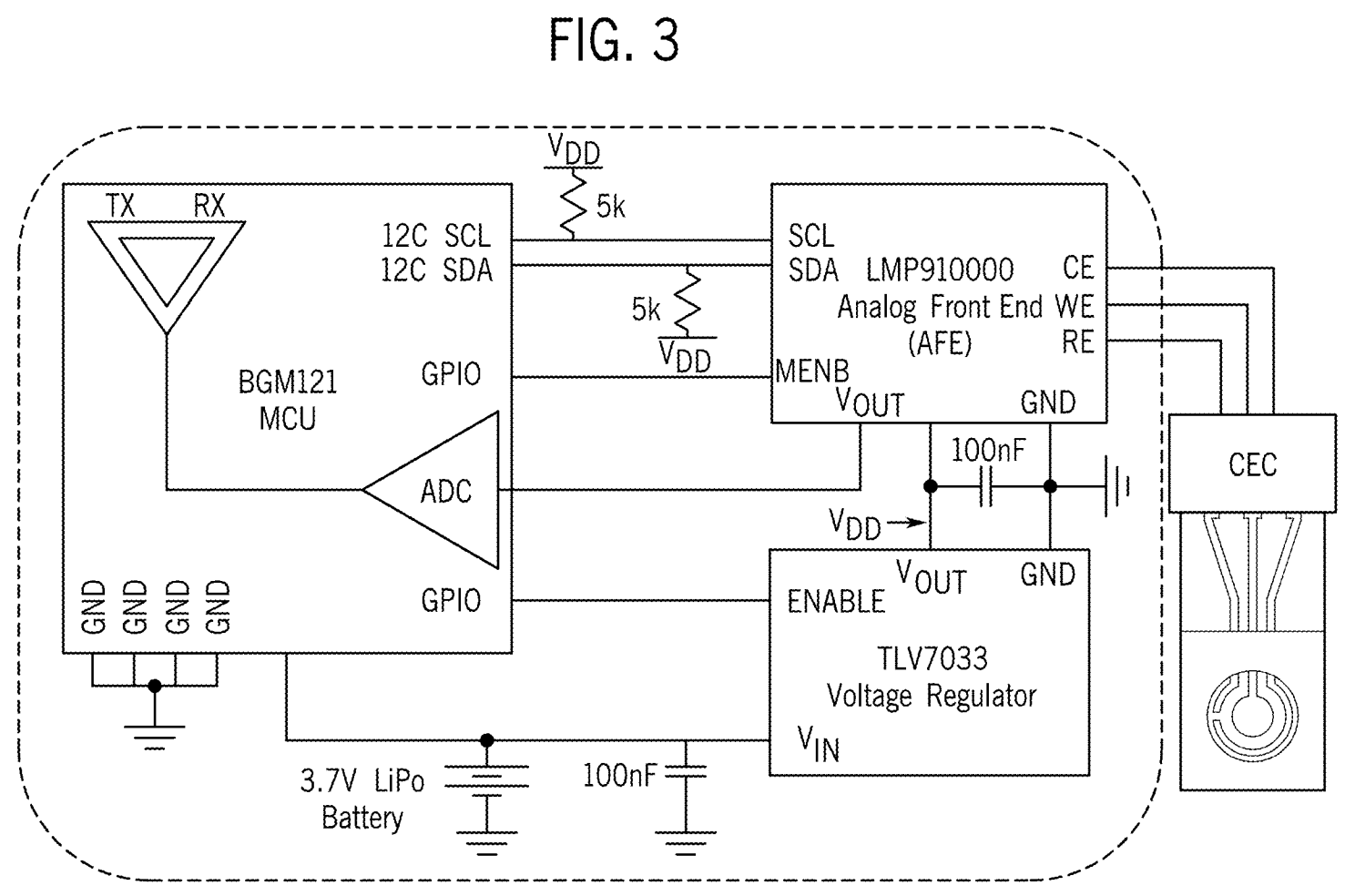

Referring now to FIG. 3, an exemplary schematic of readout circuitry employed in the bPod 200 for electrochemical Measurements is shown.

Electrochemical Sensor

The electrochemical sensor is fabricated using traditional microfabrication techniques on a glass substrate. In one embodiment, the three-electrode sensor configuration may include patterned 200 nm thick gold working and counter electrodes as well as a 250 nm thick silver/silver chloride reference electrode, with 20 nm of chromium serving as an adhesion layer between the gold and the Pyrex surface. The reference electrode is used to maintain a stable voltage bias at the working electrode surface in order to initiate the electrochemical reaction. The current response is then measured between the working and counter electrodes. Gold was chosen as the sensor material due to its biocompatibility with cells and because it will not react during the electrochemical reaction. The 3 electrode sensors were then diced into 9 mm×19.6 mm slides and interfaced with the device.

The dissolved oxygen sensor is realized by introducing an electrolyte buffer to the electrode surface. The device is covered by a gas permeable, liquid impermeable FEP membrane, which allows for diffusion of oxygen between the two solutions while the system reaches an equilibrium. The membrane is then sealed to the device using a small commercial O-ring. Oxygen concentration can then be interrogated at scheduled intervals that depend on the membrane diffusivity and agitation generated by the bioreactor batch process.

Figure 4:
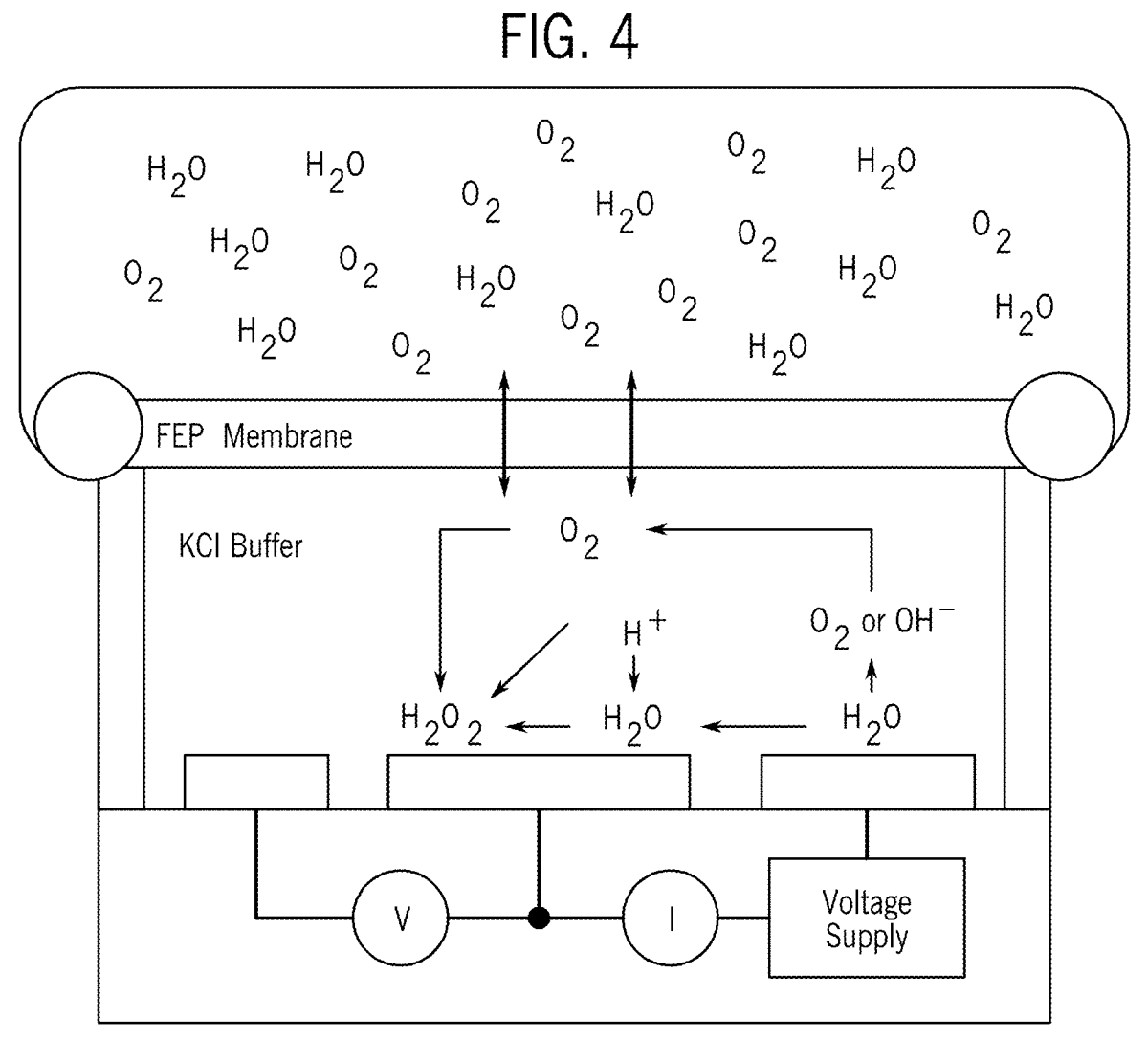

FIG. 4 is a cross-sectional view of Clark electrode contained within the KCl reservoir. Oxygen reduction reaction is represented using a three electrode system with gold working and counter electrodes, and a silver/silver chloride reference electrode.

Figure 5B:
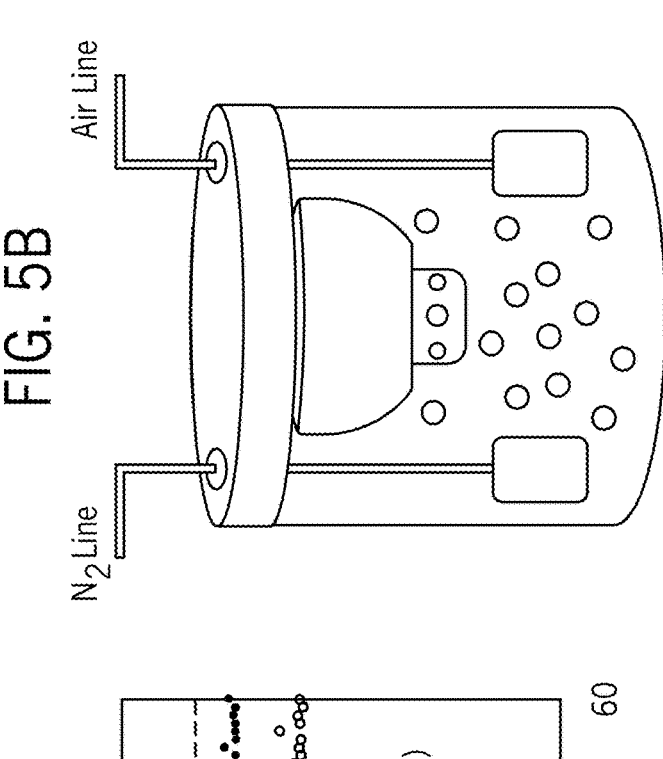
FIG. 5B shows an experimental setup for determining sensor dynamic range in a sparged environment.

For initial characterization of the device prototype a model environment was constructed to simulate two DO states: 0% DO saturation and 100% DO saturation. As seen in FIG. 5B, the bPod is sealed in a glass vessel and submerged in an electrolyte solution. Two gas lines are inserted into the container and connected to bubble diffusers. By purging N2 the DO saturation of the solution is effectively lowered, and vice versa when air (30% O2) is purged into the system then the percent saturation of DO will increase.

Figure 5A:
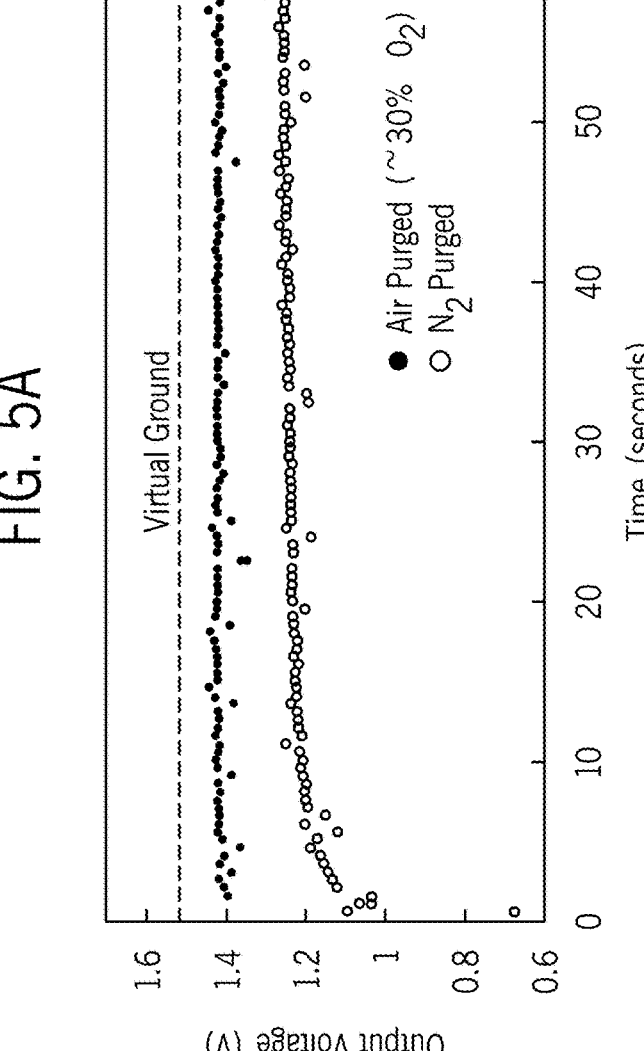
FIG. 5A shows a graph of averaged voltage output of sensor response.

FIG. 5A shows averaged voltage output of sensor response (N=5). System was purged with either air (blue) or N2 (red) at 5 minutes intervals at an applied voltage bias of V=−0.45V. A decrease in the output voltage corresponds to the reduction of dissolved oxygen. FIG. 5B shows an experimental setup for determining sensor dynamic range in a sparged environment.

During the experiment the purging of N2 and O2 was alternated every 5 minutes, and a 60 second measurement was taken by the bPod and transmitted to the PC via wired universal asynchronous receiver-transmitter (UART) communication. This process was repeated 5 times and the results are displayed in FIG. 5A. Based on the decrease of the output voltage of the bPod it is possible to verify the presence of DO. This is due to the reduction of oxygen at the sensor surface, resulting in a higher current response. Also, it is shown that after purging nitrogen the output voltage shifts upwards towards the virtual ground of the circuit, indicating a lower current response from the sensor.

Thus, the invention and concept seek to provide one or more improvements to the capabilities of bioprocess monitoring within bioreactors. The adaptable platform demonstrates a portable in situ solution for enhanced design and optimization of bioreactor control systems. In addition, the device seeks to address bioprocess parameter heterogeneities and gradients resulting in greatly reduced batch product yields. In some embodiments, the presently-disclosed apparatus (the disclosed bPod sensing platform) may be used to form a robust wireless sensor network using Bluetooth Mesh to accurately extract data from a lossy media. In various embodiments, the apparatus may include a sensor interface and electronic module that are interchangeable to a variety of sensor modalities and capable of sensor multiplexing. In further embodiments, the bPod apparatus may be used as an enabling technology with which to perform localized measurements throughout the industrial bioreactor.

Example 1—bPod: Wireless Dissolved Oxygen Sensor System Towards Bioprocess Monitoring This Example presents the bio-process monitoring online device (bPod) towards real-time in situ monitoring of bioprocess parameters such as dissolved oxygen (DO). The system may include an analog-front-end (AFE) potentiostat IC, a Bluetooth Low Energy (BLE) microcontroller, and an electrochemical three-electrode sensor. The components may be integrated into a package that is 3-D-printed or molded. bPod enables tether-less measurements of DO percent saturation and wireless data transfer to a custom Android application. The integrated DO sensor was able to clearly distinguish between nitrogen (0% DO) and air (22% DO) sparged states, with electrochemical responses of 1V (-15 µA) and 0.8V (-20 µA), respectively. This work demonstrates successful integration of the system components within a highly adaptable biosensor package amenable to deployment of wireless sensor networks for monitoring bioreactor environments.

Previous work has reported the successful development of an electrochemical solid state DO sensor. More recently, efforts towards fully integrated in situ systems have incorporated wireless communication capabilities for enzymatic electrochemical sensing in bioreactors. Here, a complete system has been developed, utilizing wireless BLE communication and a portable AFE to perform programmable in situ electrochemical measurements of DO in a robust platform for continuous bioprocess monitoring.

Figure 6:
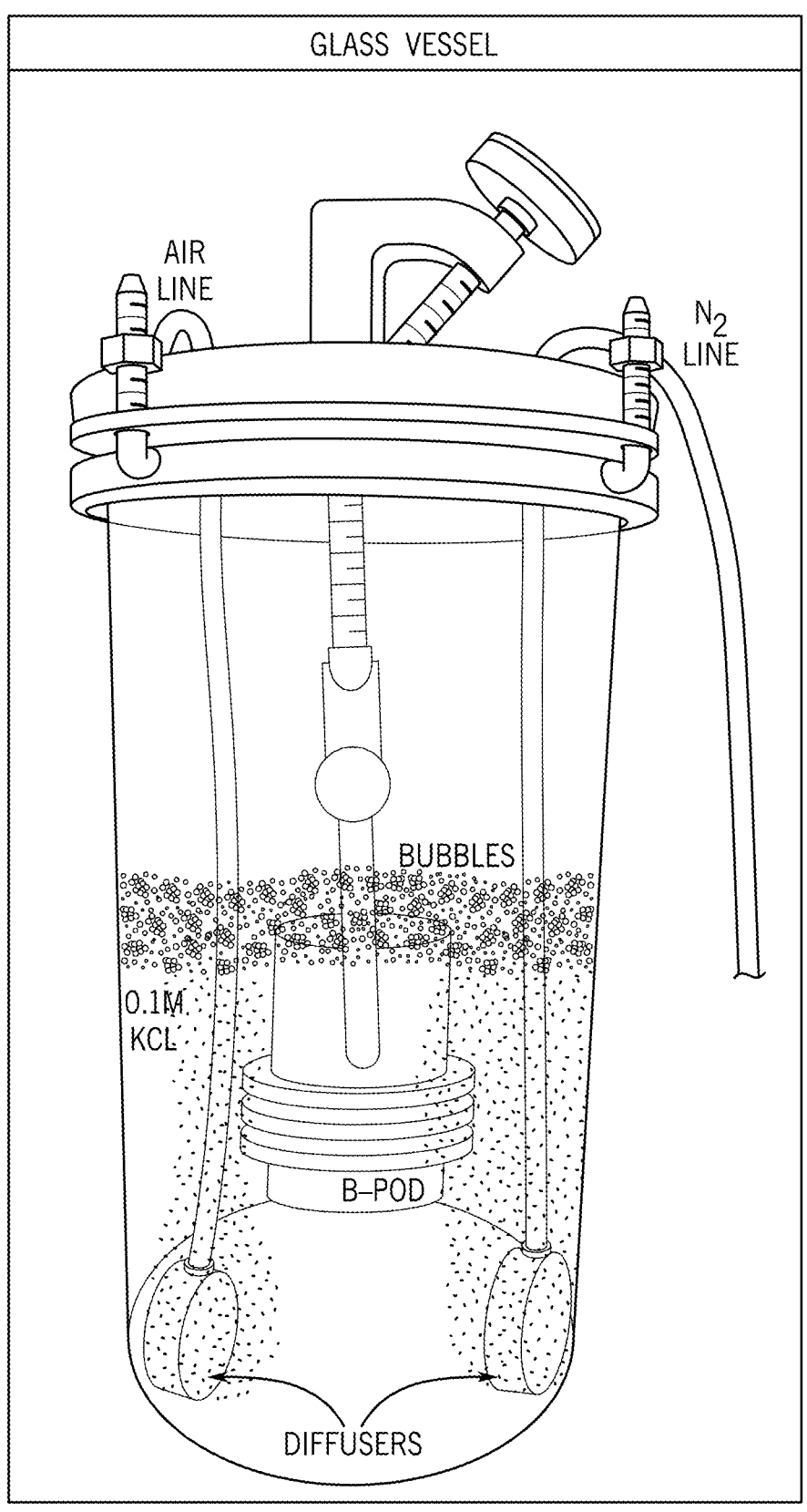
FIG. 6 shows a photo of an experimental setup for controlled sparging of air and N2.
Figure 7:
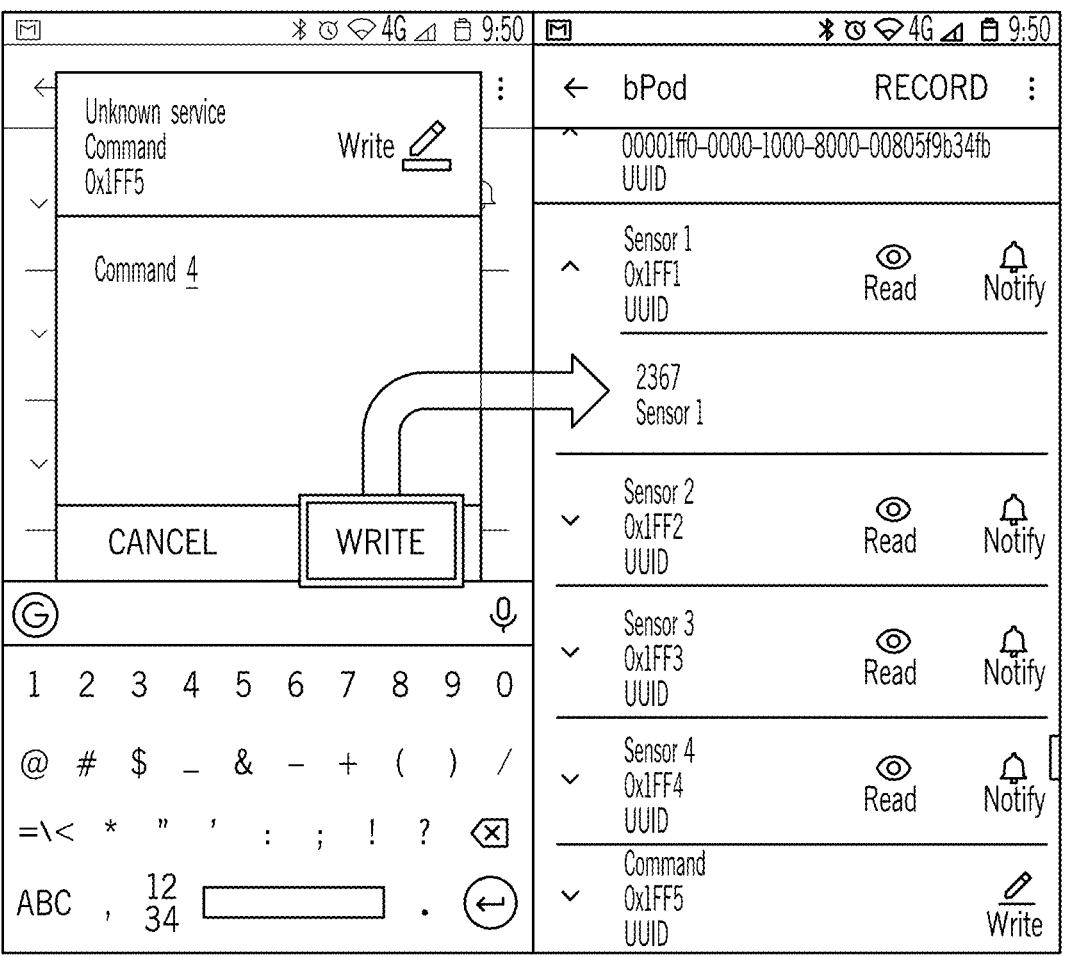
FIG. 7 shows a screen capture of an android application showing data acquisition from DO sensor, with write commands corresponding to desired device operation.

A front and back exploded view of the system is shown in FIGS. 2A and 2B. The electronic module and three-electrode sensor are integrated with the 3-D printed "marble-like" (e.g. spherical) packaging (diameter: 60 mm) and assembled from three attachable parts. The two halves (top and bottom) of the device are attached by a bayonet twist connector, and sealed with three silicone O-rings to prevent leaking. The electrodes are connected to the LMP91000 AFE, which sets the bias voltage point and acts as a current-to-voltage converter. The signal is then sent to an Analog-to-Digital converter (ADC) on the BGM121 wireless microcontroller, as shown in the circuit schematic in FIG. 3. The three-electrode sensor is fabricated on a Pyrex substrate with planar gold working and counter electrodes and a silver reference electrode. The sensor is housed within a 0.1M KCl electrolyte buffer and isolated from the solution with a gas-permeable membrane as shown in FIG. 4. FIG. 6 shows the bPod submerged into the test vessel of 0.1M KCl and sparged with nitrogen or air. Data acquisition is prompted via a command from a smart phone. Data is sent to the phone and then stored into a time-stamped excel file as shown in FIG. 7.

Experimental Results

Figure 8:
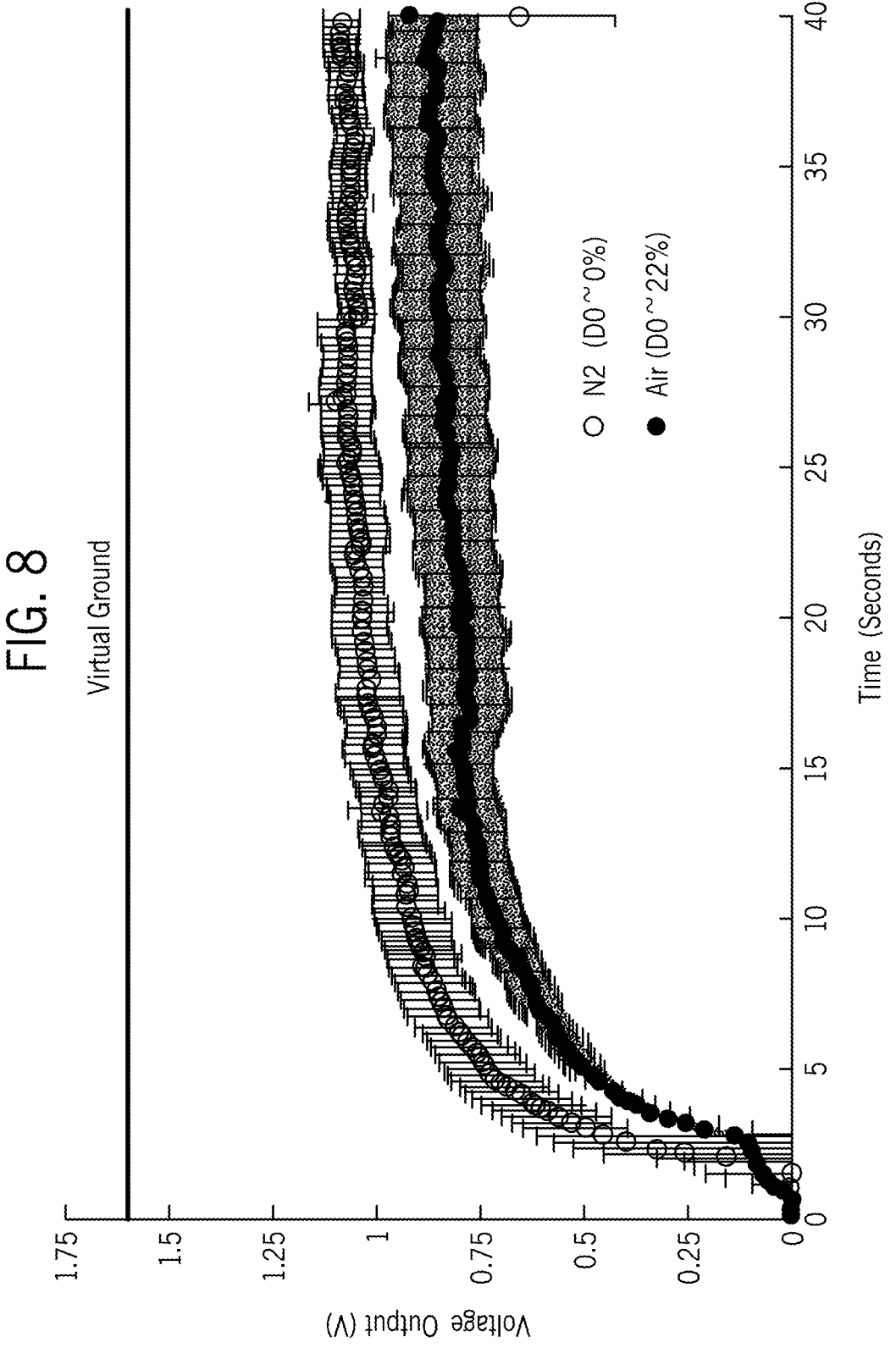
FIG. 8 shows a graph of averaged voltage output of sensor response.

Varying DO saturation levels are generated by purging air and nitrogen into the vessel, which is filled with KCl solution, until an equilibrium is measured using a polarographic DO probe (Mettler Toledo). Data is then sampled with the bPod at 200 ms intervals for 40 seconds per measurement. Parafilm and epoxy were used to maintain a leak-proof seal throughout during the experiments. FIG. 8 presents the averaged voltage output at the two DO saturation states, as compared to a baseline virtual ground measurement. As the DO saturation percentage is increased, the detection of dissolved oxygen is reflected as a 5 µA increase in peak reduction current as compared to the nitrogen state. The results confirm system operation and demonstrate significant progress towards real-time wireless bioprocess monitoring. FIG. 5 shows averaged voltage output of sensor response (N=4). System was purged with either air or N2 in 0.1M KCl at 10 minutes intervals using an applied voltage bias of V=-0.45V. Standard deviation is shown in the shaded regions for air and N2, respectively. A decrease in the output voltage corresponds to the reduction of DO.

Systems Integration and Assembly

Systems integration barriers will be overcome by incorporating extensive plans for sub-system evaluation and incorporation—these span biological and electrical components. In-depth study of sub-system interplay is a critical aspect to device assembly that is often overlooked or oversimplified.

System-level integration challenges are present where device-born aspects interact with external environmental factors. For example, fluid flow is governed not only by the external inputs, but also by the fluidic resistances of all parts of the design. The testbeds have been selected carefully, not just for their impact, but also for their relative simplicity in systems integration. For example, deployable modules (e.g., see below) are envisioned having no fluidic valves or pumps, rather time-actuated access can be enabled to wicking materials that, in turn, are electrochemically connected to electronics. For this, means have been developed to functionalize materials that convey molecular information by innovative methods of biofabrication.

Elucidation of the fundamental miniaturization effects will draw guidelines for the design and fabrication of the next generation hybrid devices with embedded biomaterials as the key functional sensing elements for testbed applications. This research will clarify fundamental compatibility and testing aspects towards electrochemical-based analysis of environmental samples using biofabricated and easily programmed microsystems. As noted earlier, component parts and their assembly are inexpensive, and easily assembled. Structural and electrochemical analyses can be developed to compile functional characteristics and limitations of all device components.

Autonomous Bioprocessing Capsule

There is a great need to develop rapid, low cost, and reproducible sensing systems for interrogation of mammalian cell bioreactors. A wirelessly programmable cell-like device will enable near real time access to molecular information.

This will be transformative for the biotechnology industry in several ways. First, a dynamic and autonomously functioning cell-like device, when deployed in parallel, offers the potential for hundreds of real time measurements, each reflecting a microcosm of the bioreactor. It is well known that therapeutic glycoproteins display significant glycan heterogeneity—a problem under intense investigation and FDA oversight. As a result, the regulatory comparison between off-patent biosimilars and innovator products becomes cloudy. Process analytical technologies that inform product quality are a significant unmet need. It is also well known that even lab scale bioreactors are, in fact, truly heterogeneous even with respect to the level of dissolved oxygen. Yet, there is limited knowledge as to whether bioreactor heterogeneity contributes to product heterogeneity, as there are no analytical measurements for bioreactor heterogeneity. These devices do not exist today.

The concept is a standalone, fully deployable, autonomously operating device that wirelessly communicates with distant networks. It is transformative in two key respects. First, it will offer near real time data from within the bioreactor. Second, because it is simple, robust, and neutrally buoyant, deployment of dozens at a time can be possible. There exists no data today on process heterogeneity, even for simple measurements such as oxygen, pH, and glucose. This scenario can be altered by generating devices that are dynamically responsive and that report their findings. This testbed depends on integration of all research-based Thrust Areas for device design, component development, and assembly.

Example 2—bPod Development

Recent advancements in continuous monitoring of large-scale pharmaceutical bioprocessing has enabled rapid, high quality, and high throughput production of a wide variety of mammalian and bacterial culture products (i.e., biopharma-ceuticals, antibiotics, and vaccines). Among these, mono-clonal antibodies (mAb) are a critical product for both therapies and diagnostics. Monoclonal antibodies are capable of targeting specific antigens and are gaining trac-tion in the treatment of cancer and autoimmune disorders among others. Furthermore, scaling and optimization of these processes has driven significant financial investment from biopharmaceutical and biomanufacturing industries with global biopharmaceutical market values expected to reach approximately $390 billion by the end of 2019.

A major concern, most common in large-scale bioreac-tors, is the presence of spatial gradients or heterogeneity of culture parameters that reduces bioreactor product yield and creates products with varying or inconsistent efficacy. For example, controlling bioreactor heterogeneity is relevant to recombinant DNA processes utilizing *Escherichia coli* coil), as well as other highly productive mammalian cell lines, such as Chinese Hamster Ovary (CHO) cells, as a host organism. Widespread use of CHO cells has been attributed to the demonstrated safety of CHO cells as a host, their low specific productivity, capacity for efficient post-translational modification compatible with humans, and easily adaptabil-ity to growth in serum. The proliferation of *E. coli* recom-binant DNA products and CHO cells is controlled by the precise regulation of culture parameters throughout the bioreactor, namely, dissolved oxygen (DO), pH, glucose, and temperature. More uniform distribution of these process parameters throughout the reactor will create better, more reliable products. Understanding the origin of these inho-mogeneities and how process parameters effect the unifor-mity of the reactor products is critical to obtaining higher process yields with ultimately more effective products. Cur-rently, standard techniques for monitoring culture param-eters in bioreactors involve inline instrumental probes—widely used amongst the biomanufacturing and biopharmaceutical industries. However, inline probes only represent a single-point measurement taken as the averaged value for an entire cell reactor. To overcome this limitation, new implementations of real-time in-situ sensors are needed that can permeate the bioreactor flows to achieve high precision bioprocess monitoring.

Wireless in situ devices exhibit numerous advantages over traditional probes and will help to eliminate reactor condition non-uniformities. Most notably, they interact locally with solutions/feedstocks throughout the reactor, have a lower contamination risk and represent a cost-effective path towards device scaling and multiplexed mea-surements, providing significant improvements in process scale-up and bioreactor optimization. However, wireless modules ideally overcome several challenges towards bio-process monitoring before becoming viable replacements, such as power consumption, module size, biocompatibility with products, and communication through a lossy media. Moreover, methods integrating commercial-off-the-shelf (COTS) components with wireless modules have enabled a variety of new applications using in situ sensors and pack-aging configurations for specific environments. By modernizing current approaches with application specific electron-ics, miniaturized sensors, and 'smart' materials, devices can address a variety of challenges at a lower cost and with higher resolution than ever before. The paradigm of inte-grating microsystems and biosensor technologies is well positioned to not only enhance capabilities but revolutionize the next generation of bioprocess monitoring for the bio-medical and biomanufacturing industries.

FIG. 9 shows a conceptual overview of fully integrated bio-process online analytical device (bPod). Module swarm is deployed into stain-less steal bioreactor. bPod system components allow for underwater amperometric measure-ment of DO and wirelessly transmit the data to an external device via Bluetooth communication.

In this work, the bio-process online analytical device (bPod) was developed for real-time wireless, in situ moni-toring of dissolved oxygen. The bPod highlights integration and design of key system components to achieve a scalable prototype that specifically addresses challenges associated with in situ sensing within bioreactors. The platform includes an electrochemical Clark-type oxygen sensor and an amperometric potentiostat readout circuit paired with a Bluetooth low energy (BLE) system-in-package (SiP) microcontroller all contained within a leak-proof 3D-printed package. The BLE functionality allow for wireless data transmission to a custom smartphone app while the Clark-type gold electrochemical sensor enables the measurement of dissolved oxygen partial pressure in a non-conductive media.

Development of Wireless 'Smart Marble' Platform

The goals of this research are the design and systems integration of a marble-like platform for wireless real time, in situ bioprocess monitoring within industrial bioreactors. Initial efforts into this topic sought to improve understanding of suitable wireless modalities for data transmission through a lossy media, design of a readout circuit topology that would enable electrochemical sensing, as well as 3D-print-ing a bio-compatible enclosure designed to encapsulate the device. Comparative studies of multiple wireless communi-cation methods were conducted focusing primarily on scal-ability of the system and the availability of needed func-tionality. Key metrics considered were form factor, power consumption, available peripherals, and wireless transmis-sion performance. It was determined that a BLE communi-cation solution would satisfy all key design requirements, while also providing capabilities for future adaptation into a sensor network (i.e. Bluetooth Mesh) enabling robust device-to-device communication. Additionally, the system takes advantage of COTS components to achieve a workable prototype for sensor testing.

Integration of Dissolved Oxygen Sensor for Real-Time Monitoring

In order to successfully demonstrate the effectiveness of the platform, monitoring of a pertinent bioprocess parameter was explored. While initially investigating glucose and temperature sensing it was determined that the detection of dissolved oxygen content during the cell culture would prove to be essential in multiple bioreactor environments. Therefore, the primary focus of this work is the fabrication and integration of a dissolved oxygen sensor with the proposed platform. A three-electrode electrochemical oxy-gen sensor based on a Clark-type electrode configuration was explored. For oxygen sensing, the electrodes are con-tained within an electrolyte solution and are isolated from the surrounding media using a gas permeable fluorinated ethylene propylene (FEP) membrane. Leveraging the mate-rial properties of the electrodes and membrane, respectively, a fully integrated device prototype was assembled and tested at various dissolved oxygen saturation percentages generated using mixtures of pure oxygen and nitrogen and compared to a commercial inline DO probe.

System Overview of Bio-Processing Analytical Online Device (bPod)

The preceding sections presented the motivation behind the development of in situ wireless nodes for deployment in bioreactors, along with background information providing context for the design and development of the research and work presented herein.

The proposed device contains three main system components: an electronic module, a leak-proof 3D-printed enclosure, and an electrochemical DO sensor. The electronic module utilizes a Bluetooth Low-Energy chipset and a portable potentiostat integrated circuit, or analog front end (AFE), to enable wireless amperometric monitoring of DO. The leak-proof packaging is 3D-printed using a biocompatible material, MED610, to seal the device using a combination of O-rings and an interlocking bayonet connector. A Clark-type DO sensor is assembled by forming an electrolyte well with electroplating tape, trapping the electrolyte with a liquid impermeable fluorinated ethylene propylene (FEP) membrane. This creates a gas permeable diffusion barrier between the solution and the electrolyte above the electrode surface.

In the envisioned implementation of the bPod deployment, multiple bPod's will be placed inside the bioreactor with each individual device performing localized measurements of relevant culture parameters. The bPod could be deployed in large stainless-steel bioreactors as well as small and large single use bioreactors (SUB), allowing the convenient extraction of information via BLE, or a Bluetooth Mesh approach. Eventually, these measurements could be fed back into the control system of the bioreactor enabling real-time tuning of culture parameters increasing process yield.

Fabrication of Electrochemical DO Sensor

Figure 10:
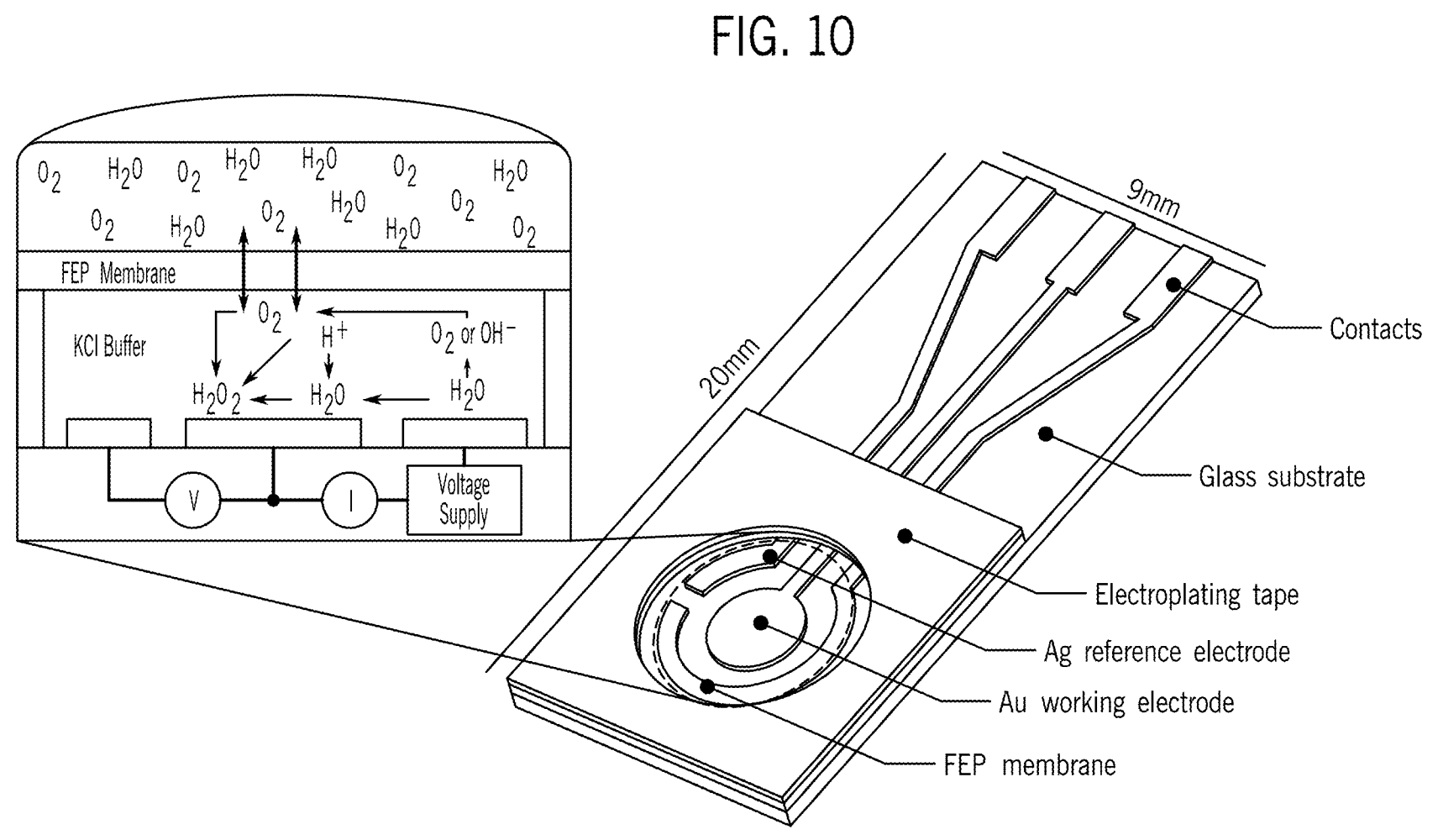

In this work, a three-electrode configuration is utilized for the amperometric measurement of dissolved oxygen partial pressure, denoted as a saturation percentage. FIG. 10 illustrates the final DO sensor assembly, including a contained reservoir of electrolyte solution on the three-electrode sensor with an attached fluorinated ethylene propylene (FEP) membrane to create a gas permeable, but liquid impermeable, interface between a contained electrolyte solution and the surrounding media. FIG. 10 illustrates an assembled dissolved oxygen sensor and a cross-sectional diagram of oxygen reaction at the Clark-type electrode. The oxygen reduction reaction is measured using a three-electrode system with gold working and counter electrodes, and a silver reference electrode.

The bPod platform has been disclosed above, along with the system components used for interfacing with the sensor. The challenge of ensuring a reliable and leak-proof interface is addressed herein and dictates several modifications to the DO sensor assembly. In the following sections, the design, fabrication, and assembly of the proposed DO sensor and its components will be discussed.

Sensor Designs

Here the full design and specifications for the fabricated electrode are explained, beginning with motivations for the sensor materials and topology, then moving towards specific fabrication details to complete the miniaturized DO sensor.

Glucose Sensor

The initial electrochemical sensor that was investigated for use in the bPod was a glucose sensor, chosen for the importance of glucose concentration in cell growth and metabolism. Typical glucose sensing topologies involve three-electrode sensors with a glucose oxidase (GOx) functionalized working electrode. As glucose interacts with GOx at the surface of the electrode, under a specific voltage bias, a chemical reaction will produce hydrogen peroxide ($H_2O_2$). Reduction of $H_2O_2$ at a platinum working electrode produces a measurable reduction current, corresponding to a maximal excitation voltage peak. Extensive studies have been conducted that characterize both the functionalization/bonding of GOx to Clark electrodes, as well as modifications such as dendrimer analogues (nano-sized, radially symmetric molecules with homogeneous tree-like structures ideal for binding) to achieve chemical specificity to glucose as compared to other sugars (i.e. lactose and fructose). While glucose biosensor applications are well documented and widely used amongst researchers and the general population, their one-time use or limited use (i.e. glucose strips) application makes long term sensing at small scales very challenging. Since the overall architecture of the glucose sensor is based on similar implementations to the Clark cell oxygen sensor, it served as a natural segue into the design of a dissolved oxygen sensor, however the application was not pursued beyond electrochemical characterization of the sensors in glucose solutions. Additionally, signal conditioning requirements for the glucose sensor provided an initial platform for the development of the bPod electronics. Details of this characterization are included below and were critical for identifying several key design features of the final DO sensor assembly.

A commercial screen-printed glucose sensor (BVT Technologies), with GOx derived from *Aspergillus Niger* immobilized on a 1.0 mm diameter platinum electrode, was purchased from PalmSens for determining electrochemical parameters needed for design of the bPod potentiostat IC as shown in FIG. 11. FIG. 11 shows a PalmSens glucose electrode with GOx (*Aspergillus Niger*). The schematic provides the relevant dimensions of the AC1.GOD glucose sensor (in mm). The electrodes were 7.26 mm in width and 25.4 mm in length with a 2.54 mm pin pitch. The counter electrode was made of platinum and the reference electrode was made from silver.

The AC1.GOD glucose sensors were stored in a −20° C. refrigerator. Prior to performing glucose measurements, the electrodes were first allowed to acclimate to room temperature, then submerged into a negative control of 1× pH7.2 phosphate buffered-saline (PBS) for 30 seconds. The 30 second wait time was normalized across each glucose concentration prior to electrochemical measurement. Cyclic voltammetry (CV) was performed to identify the peak current response from the sensor, which was verified with a chronoamperometry (CA) utilizing the excitation bias at which the peak current response occurred (VB=−0.1 V).

Figure 12A:
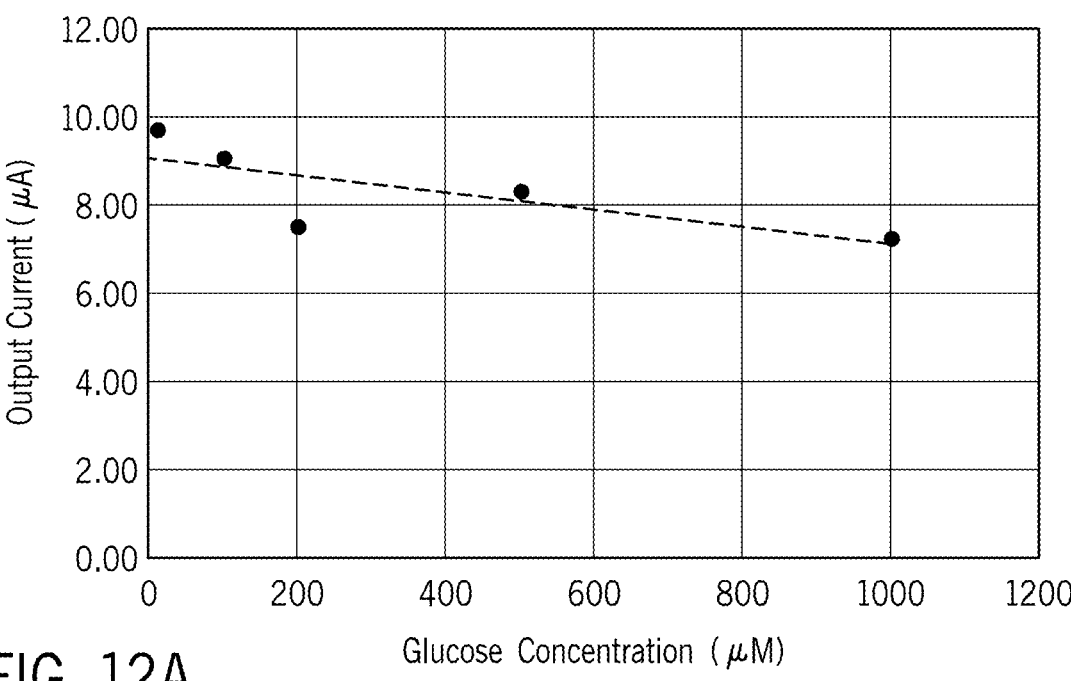
FIG. 12A shows concentration curves for aGOx sensor in glucose solutions.
Figure 12B:
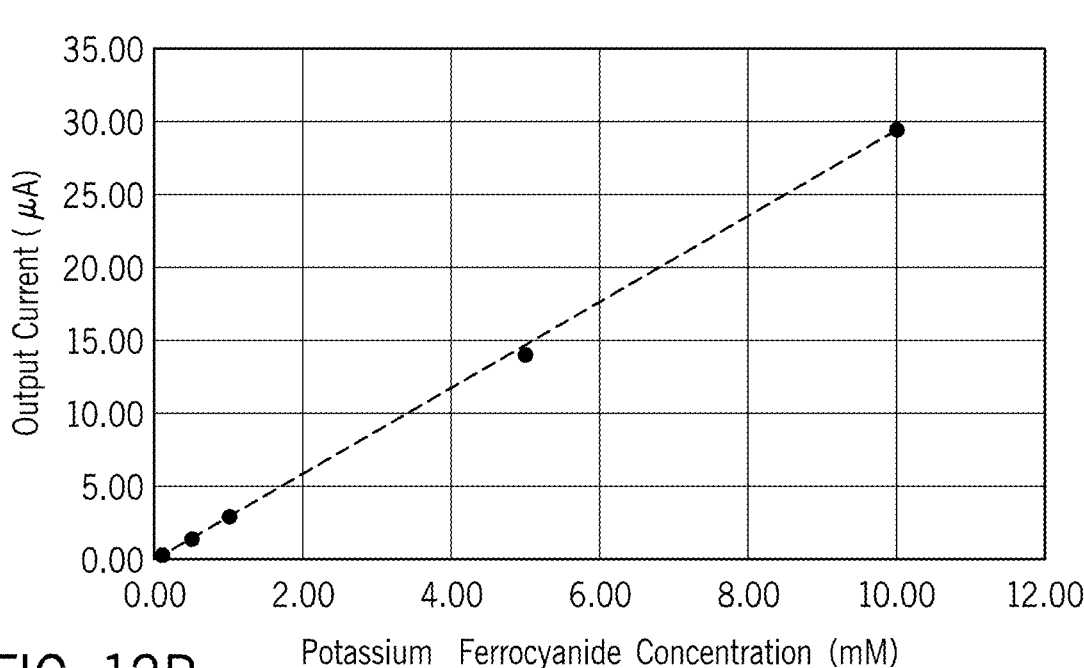
FIG. 12B shows concentration curves for a bare gold sensor in several $K_4Fe(CN)_6$ solutions, ranging from PBS, 10 µM, 100 µM, 200 µM, 500 µM, and 1 mM.

Electrochemical characterization was performed with the BioLogic potentiostat, to generate concentration curves for the GOx electrodes. For these sets of experiments the concentrations of the glucose solutions were chosen to reflect glucose ranges described in the datasheet reported by the manufacturer. The targeted glucose concentrations include PBS alone (i.e., 0 M glucose), 10 μM, 100 μM, 200 μM, 500 μM, and 1 mM. The findings are summarized in the calibration curve below in FIG. 12A. FIG. 12A shows concentration curves for aGOx sensor in glucose solutions. FIG. 12B shows concentration a bare gold sensor in several $K_4Fe(CN)_6$ solutions, ranging from PBS, 10 μM, 100 μM, 200 μM, 500 μM, and 1 mM. In order to eliminate any doubt from the instrumental setup correlated to the poor linear fit of the glucose electrode, electrochemical measurements were performed with a chemical which exhibits Nernstian behavior, potassium ferrocyanide ($K_4Fe(CN)_6$), using a commercial 2.0 mm diameter bare gold electrode (DropSens). These electrodes differed slightly in size, though could be fitted into the same card edge connector. Calibration curves were generated similarly to the glucose measurements above, however, a linear fit showed a much improved and predictable response as shown in FIG. 12B.

Since the reference electrode of the AC1.GOx glucose sensor was pure silver and not silver/silver chloride, it was susceptible to a slight voltage shift over repeated measurements. This behavior was monitored by using a separate control solution of only PBS. The PBS and glucose concentration measurements were performed in parallel under the same excitation conditions to determine if the glucose was assisting this voltage shift. On the contrary, the solution with glucose at any concentrations remained reasonably stable, and significant shifting only occurred in the control PBS solution, due to the lack of discernable voltage peak. The only noticeable change found in the target solution was an initial shift when moving from PBS to the lowest concentration, signifying that the reduction peaks associated with glucose were well characterized.

CA and CV measurements of glucose performed using the Biologic potentiostat were later compared to measurements taken using the LMP91000, however the results were not able to confidently reflect an accurate reading of glucose concentration after many repeats. Several factors may contribute to this, including the possibility that the glucose concentrations were too high (~10 mM) and caused sensor saturation, even though the concentrations were chosen in reference to the manufacturer provided calibration curves. Additional parameters such as equilibration time, temperature acclimation, reference electrode shift, and measurement duration were all modified in the attempt to extend electrode lifetime. However, the PalmSens electrodes presented limited effectiveness towards the measurement of glucose beyond one time use applications, which would have been detrimental for integrating with the bPod. The utility of these electrodes lied instead in measurement of more standard and predictable analytes with clear oxidation peaks, such as $K_4Fe(CN)_6$, which has an oxidation peak at 0.22 V, to compare readings from the benchtop potentiostat (BioLogic) to the LMP91000.

In summary, commercial screen-printed electrodes provided the necessary background for the design of the fabricated DO sensor, and assisted in fine tuning methods for evaluating electrochemical properties of the sensors. Specifically, investigation of a commercial glucose sensor highlighted the advantages of the 3-electrode Clark-type topology, as well as design considerations for the surface areas of the working electrode, which could be directly applied to the fabrication of the oxygen sensing electrodes. Not only is robustness and response time of the sensor important, but the electrochemical sensor lifetime ideally lasts for the duration of the bioprocess monitoring application.

Dissolved Oxygen Sensor

Electrodes for the detection of dissolved oxygen were fabricated on top of a Pyrex™ substrate. Each individual sensor was 9.0 mm in width and 20 mm in length with a contact pin pitch of 2.54 mm. These dimensions allowed the sensors to interface with the electronic module through a card edge connector, which had a 10 mm×8 mm cavity for positioning of the sensor, as well as to provide enough spacing (13.7 mm) between the contact pads and sensor area for the addition of leak-proof fittings. Similar to several commercial glucose sensors, the WE electrode was designed to have 4.0 mm diameter. The surface area of the CE compared to the WE was designed in a 2:1 ratio.

Figure 13:
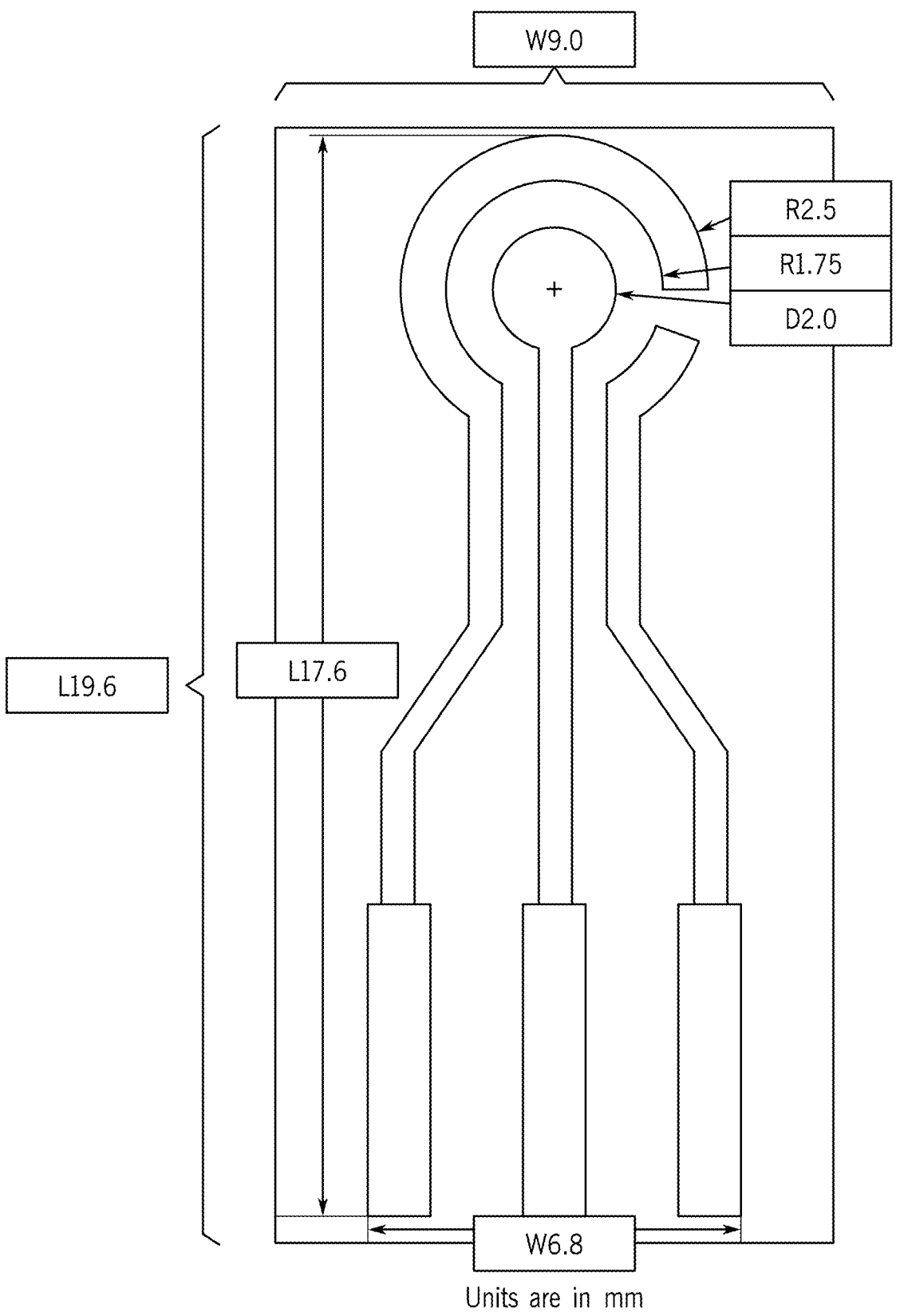
FIG. 13 shows a schematic detailing the dimensions of a custom DO sensor drawn in AutoCAD.

FIG. 13 shows schematic detailing the dimensions of custom DO sensor drawn in AutoCAD. Length and width were determined to interface with a card edge connector (CEC) and the electronic module.

Electrode Fabrication

This section describes the design and fabrication of the electrochemical DO sensor. All fabrication was performed at the UMD Nanocenter and its Fablab.

Shadow Mask Creation

Figure 14B:
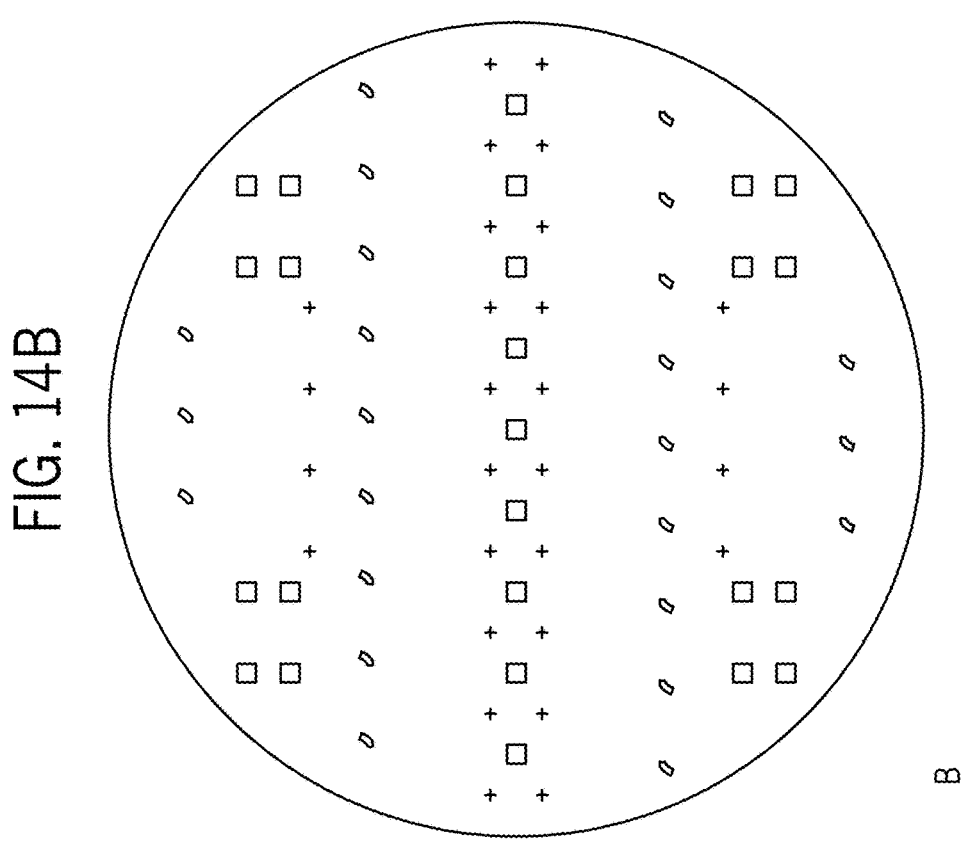
FIG. 14B shows a mask design for electrode patterning for Ag deposition.
Figure 14A:
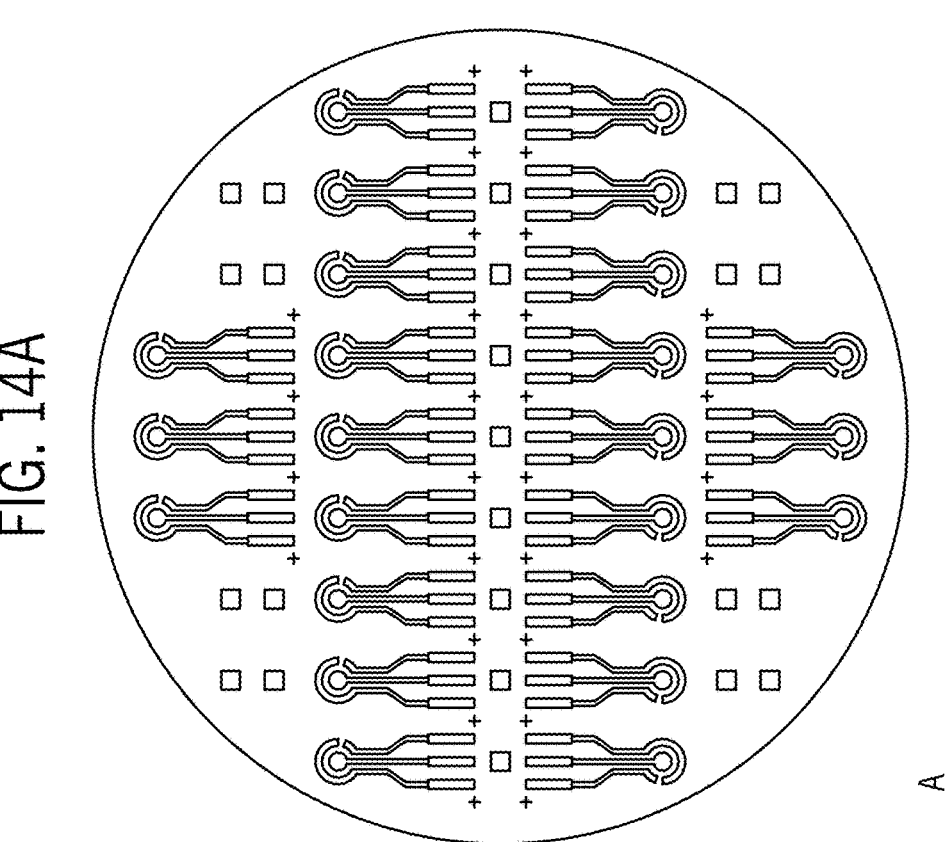
FIG. 14A shows a mask design for electrode patterning for Cr/Au deposition.

Due to the millimeter scale geometry, paper shadow masks provide sufficient spatial resolution of the electrode pattern. Two shadow masks were drawn in AutoCad and then laser cut into cleanroom paper using an Epilog laser cutter, shown in FIGS. 14A and 14B. FIG. 14A shows mask design for electrode patterning for Cr/Au deposition. FIG. 14B shows mask design for electrode patterning for Ag deposition. The first mask was used for patterning gold onto a Pyrex substrate for formation of the working and counter electrodes. A second mask was used to pattern silver onto the reference electrode. Laser raster speed and power output were adjusted to improve the resolution and to completely cut through the cleanroom paper. The resolution of the laser cutter was found to be 100 μm, thereby limiting the smallest feature sizes for the electrode traces. Each mask design included 24 sensors oriented to maximize the surface area coverage on the 100 mm diameter wafer. Alignment marks were added for dicing and metal deposition steps. A critical challenge of using a paper mask is affixing them directly to the surface of the wafer, avoiding gaps between the mask and the wafer which will slightly alter the width of the resulting electrode pattern. To overcome this, spaced rectangular cutouts were added to the mask for taping directly to the Pyrex substrate. Despite this effort to enhance paper mask adhesion to the substrate, any loss of adhesion can impact the clarity of the e-beam patterned features. For example, the paper masks can tend to curl away from the wafer surface, and since e-beam evaporation is highly directional, this may result in some elongated or cutoff electrodes. Sources of this error can result from the placement in the substrate holder, which if the mask was not sized properly would introduce minor folding, and the limited adhesion of the tape while inside the e-beam evaporator. Additional challenges associated with the laser cutting includes accumulation of burn marks (rough edges) on the paper, which lead to non-uniform features on several of the patterned electrodes on the wafer.

E-Beam Evaporation

Figure 15:
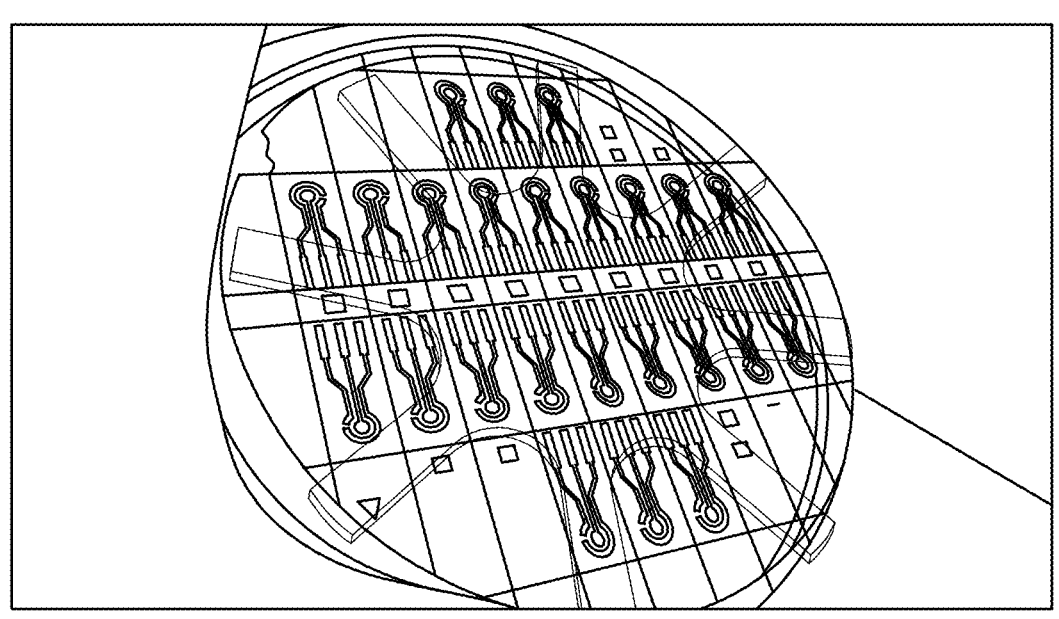
FIG. 15 shows a photograph of fabricated Clark-type sensors with gold working and counter electrodes, and a silver reference electrode.

The three-electrode sensor with a thin-film 4 mm diameter gold working electrode, gold counter electrode, and a silver reference electrode was fabricated as depicted in FIG. 15 with fabricated Clark-type sensors with gold working and counter electrodes, and a silver reference electrode. Cr/Au (20 nm/200 nm) layers were deposited using e-beam evaporation, followed by deposition of Ag (250 nm) onto the patterned reference electrode. As mentioned, the deposition pattern was created via two separate laser cutting steps (Epilog Laser Fusion) and the cleanroom paper masks were affixed sequentially to the Pyrex wafer. The alignment of the subsequent Ag mask to the initial Au patterned electrodes was performed by manually aligning the cross features on the mask through the backside of the wafer, aided by the transparency of the Pyrex substrate. After deposition, the masks were removed and the wafers were cleaned with a combination of acetone, methanol, and isopropanol (AMI), followed by rinsing with DI water and drying with nitrogen gas. The wafers were then prepped for dicing by spin coating a thin layer of Shipley S1813 positive photoresist (Micro-Chem, Westborough, MA) to protect the wafer from dust and debris during the dicing process. This procedure was completed using the Model P-6708D 8" spin coater. Spin parameters are summarized in Table 2-1 below. The wafer was then diced into individual sensors (9 mm×19.6 mm) using the dicing saw (Microautomation, Centreville, VA). A 100 μm thick perforation was leftover following the dicing process such that the sensors could be stored and then separated when ready for assembly. The yield of the fabrication process was roughly 20 electrodes per wafer, due to variations in the coverage of the reference electrode and cracking of the substrate when separated individual sensors. To remove the photoresist layer, the electrodes were once again cleaned using the AMI process and rinsed with DI water.

Table 2-1 below shows spin parameters for deposition of photoresist to achieve desired thin film thickness for wafer dicing. Wafer was baked for 100 seconds at 100° C. on a hotplate following spin coating.

TABLE 2-1

| RPM | Ramp | Time |
| --- | --- | --- |
| RPM1 = 100 | Ramp1 = 1 s | Time1 = 1 s |
| RPM2 = 1500 | Ramp2 = 1 s | Time2 = 5 s |
| RPM3 = 2000 | Ramp3 = 2 s | Time3 = 40 s |
| RPM4 = 0 | Ramp4 = 3 s | Time4 = 0 s |

Preparation of the Ag/AgCl Reference

Once cleaned, the reference electrode (RE) was functionalized to have a Ag/AgCl surface layer. This was done to ensure a stabile voltage peak for the reduction of dissolved oxygen. The Ag/AgCl REs were prepared using a 50 mL solution of 50 mM Ferric chloride to create an AgCl layer. Electrodes were dipped into solution for about 5 seconds as the electrode underwent a change in color from silver to black. The electrodes were then rinsed in two separate DI water petri dish baths to minimize contamination of the rinses and to completely remove the ferric chloride. Following this process, all sensors were cleaned using AMI. Following Ag/AgCl RE fabrication, characterization of the reference potential for stability and voltage level was conducted, as will be discussed herein. However, it was found that Ag REs will spontaneously produce an Ag/AgCl surface when under KCl solution, which is the electrolyte used for DO sensing by the Clark electrode. In fact, the ferric chloride treatment often removed too much of the silver layer and significantly reduce the lifetime of the sensor.

Electrochemical Cell

In one example, the electrochemical cell may be thought of as including three main components: a sensor, an electrolyte solution, and a gas permeable membrane. The chemical reaction with oxygen enabled by the presence of the electrolyte is explained herein. Potassium chloride is a salt that dissolves easily in water and dissociates into K+ and Cl− ions. These ions support the transfer of electrons between the electrodes, making the electrolyte more conductive. The KCl concentration utilized for DO sensing may vary slightly or include additional molecules such as glycerol to support electrochemical reactions, but typically KCl is used in a 0.1 M concentration.

What distinguishes the Clark cell is the use of a gas permeable membrane. In solution, the difference in the dissolved oxygen concentration between the electrolyte solution in the well and the external solution will cause the diffusion of $O_2$ through the membrane. The proposed membrane for the bPod is a 25 μm thick FEP membrane purchased from Strathkelvin. As expected, the $O_2$ molecules diffuse from a high to low pressure until a system equilibrium is achieved. This introduces two diffusion regions that dictate the ability of the sensor to detect changes in the external DO saturation and affects the response time of the sensor: diffusion across the FEP membrane, and within the KCl electrolyte. Therefore, the response time of the measurement of DO is diffusion limited and dependent on diffusion between the outside of the FEP membrane and electrode surface where the electrochemical reaction takes place. To allow for sufficient transfer of DO into the electrolyte chamber, the diffusivity of the FEP membrane is determined by its thickness, hydrophobicity, and pore size. Identifying the FEP membrane or the electrolyte as the diffusion limiting region will guide targeted improvements can be made to the electrochemical cell.

For the bPod, the chemical reaction of the Clark-type electrode can be summarized as follows:

$$O_2 + 2H^+ + 2e^- \rightarrow H_2O_2 \qquad (2\text{-}1)$$

$$H_2O_2 + 2H^+ + 2e^- \rightarrow 2H_2O \qquad (2\text{-}2)$$

In reference to FIG. 4 oxygen diffuses through the FEP membrane until an equilibrium is reached with the external solution. FIG. 4 shows a cross-sectional diagram of the chemical reaction for the Clark-type electrode. The oxygen reduction reaction is represented using a three-electrode system with gold WE and CE, and a silver RE. An excitation bias is applied between the WE and RE while electrons are provided by the counter electrode. The gold working electrode in this system is inert and does not interfere with the reaction, and will only accept and pass electrons to reduce $O_2$ at the working electrode surface into hydroxide ions, thus producing a current which is proportional to the partial pressure of oxygen. Additional bi-products in a KCl solution are found when the $K^+$ ions pair with the excess $OH^-$ and the $Cl^-$ pair with Ag(s) to form KOH and AgCl, thus oxidizing the RE surface. This can be observed visibly as the reference electrode surface darkens overtime, signifying the degradation of the electrode, which can result in a lower unstable current response for the sensor that is unable to be calibrated.

Attachment of FEP Membrane

Three generations of the sensor and membrane attachment to form the electrochemical cell have been explored, to date. Each generation highlights a distinct assembly strategy to achieve the goal of providing a gas permeable, liquid impermeable barrier between the external solution and internal electrolyte well. With each modification, the thickness and complexity of the Clark cell was reduced, which correlated with improved electrochemical measurements due to reduced time of $O_2$ diffusion. The three generations can be summarized as 1) an extrusion from main 3D-printed packaging body, 2) a separate 3D-printed well for each individual sensor that is inserted into the main body, and 3) an electroplating tape-based well that directly interfaces with the sensor substrate. The design motivations and commentary for the assemblies will be discussed below.

3D-Printed Screw-Top Sensor Interface

Figures 16A, 16B:
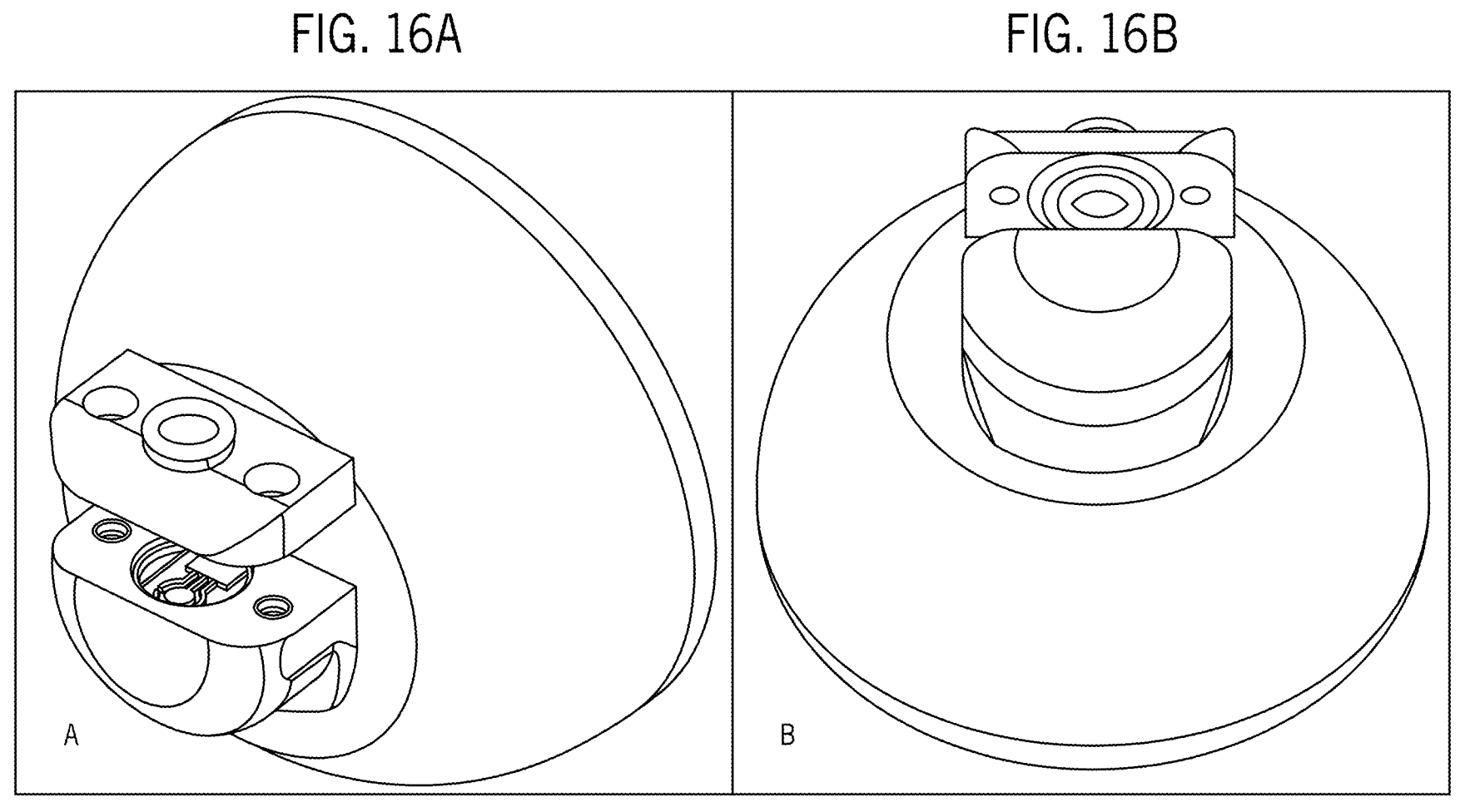

The first attempt to construct the electrolyte well (potassium chloride electrolyte) focused on modification to the main 3D-printed packaging. Though this would increase the complexity of the design significantly, it offered several noted advantages compared to assembling the electrolyte well during the fabrication process or individually for each sensor. In this manner, the same bPod enclosure could be used repeatedly without permanent sealing, by simply inserting a sensor into the packaging and screwing down the top with two screws, as shown in FIG. 16A. Additionally, a variety of electrolyte concentrations and composition could be quickly loaded and reloaded into the well and the gas permeable membrane could be applied in an efficient manner, without formation of bubbles that would skew DO measurements. FIG. 16 shows several images of the generation 2 of the 3D-printed enclosure, which will be covered in detail below. The gas permeable membrane is attached to a 5 mm opening using an O-ring. The relevant dimensions of the sensor interface include a cylindrical electrolyte well of height 7 mm (the distance between the FEP membrane and the electrode surface) and a diameter of 5 mm created by two concentric O-rings used for leak-proof sealing as shown in FIG. 16B. FIG. 16 shows generation 2 of bPod enclosure incorporating the 3D-printed screw-top interface and membrane attached using an O-ring. FIG. 16A highlights the thermoset inserts, placement of the electrode, and the sealing of the FEP membrane with a 5 mm O-ring. FIG. 16B shows the concentric O-ring feature used for creating a leak-proof seal.

However, the interface resulted in issues with leaking into the main body of the bPod at sparging system pressures, which are on the order of 10-50 mmHg. This was attributed to ill-fitting O-rings and slight bending in the 3D-printed parts resulting from the placement of the screws between the two 3D-printed pieces. Leaking issues were overcome with several iterations of the 3D-printed screw-top sensor interface as well as application of epoxy. Another concern with the electrolyte well integrated into the 3D-printed package was the distance between the FEP membrane and the surface of the sensor. This distance was found to be non-negligible, and in fact was the predominant source of diffusion limited behavior as sensor response times were observed on the order of 10-15 minutes during integrated testing of the bPod. Experiments even showed at times that there were no changes in the CA current signal between a nitrogen purged state (0% DO) and a fully oxygen saturated state (100% DO) due to prohibitively slow diffusion across the 7 mm electrochemical well thickness. While leaking issues were solved, the dimensions of the electrochemical well needed to be decreased in the subsequent generation.

3D-Printed Receptacle Sensor Interface

Figures 17A, 17B:
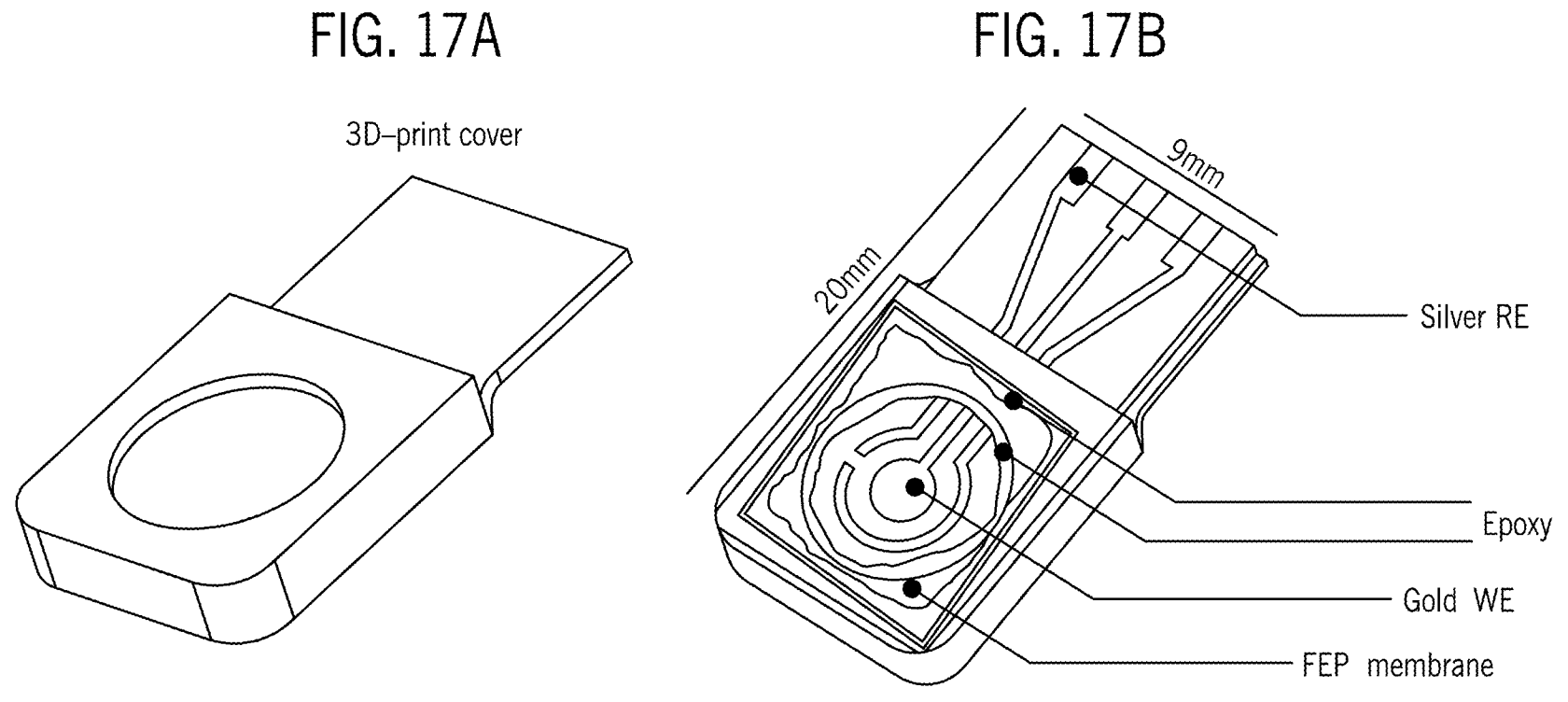

The electrochemical well was redesigned to minimize the electrolyte chamber volume, hence reducing the distance between the FEP membrane and the gold WE. To accomplish this, a 3D-printed receptacle, as shown in FIGS. 17A and 17B, was designed such that the sensor could be inserted and fixed with epoxy. FIGS. 17A and 17B show conceptual drawings of the 3D-printed receptacle sensor interface. The electrochemical well was formed by trapping 1 mL of KCl onto the sensor surface with an FEP membrane and epoxy. This was a shift in design philosophy as the modifications were conducted individually for each sensor as opposed to just the main bPod enclosure. The relevant dimensions for the 3D-printed cover are as follows: the length coincides with previous iterations and is 21 mm in total with 20 mm accounting for the cavity, the diameter of the circular opening was 8 mm, and the opening was 10 mm×0.75 mm giving a 0.25 mm tolerance for inserting the sensor. The 8 mm opening was chosen to maximize the surface area of the FEP membrane. To create the electrolyte well, the sensor was inserted into the 3D-printed part and epoxy was applied along the circumference of the circular junction between the glass substrate and the MED610 part. After drying for 5 minutes, the top of the part was covered with a thin layer of epoxy along three of the edges and a 10 mm×10 mm square cutout of FEP membrane was attached. Then 1 mL of 0.1 M KCl was pipetted into the well through the unattached side of the FEP membrane, ensuring that no bubbles were formed. Finally, the last edge of the membrane was sealed to the 3D-printed receptacle with epoxy.

The advantage of this approach was seen in the greatly reduced complexity of the overall enclosure design; however, the assembly time of each sensor was also increased to account for three separate applications of epoxy. Though noted success in measurements with this sensor configuration will be discussed below, issues arose regarding the sensor assembly lifetime. This design left very few options for refilling the electrolyte solution, and the KCl solution tended to evaporate over time unless the sensor was stored in a DI water solution. Another disadvantage was the lack of control over the spread of epoxy. During testing of the device, the epoxy may have partially covered the sensor electrodes, reducing the effective surface area of the sensing electrodes, thus lowering the electrochemical response. In addition, wicking of the epoxy along the FEP membrane could also lead to substantially lower response times and long wait times in order for the dissolved oxygen to diffuse through the membrane. As a result, the inconsistency of this design generation led to further innovation of the sensor interface that would minimize application of epoxy and speed up assembly times.

Tape-Based Sensor Interface

Figure 18:
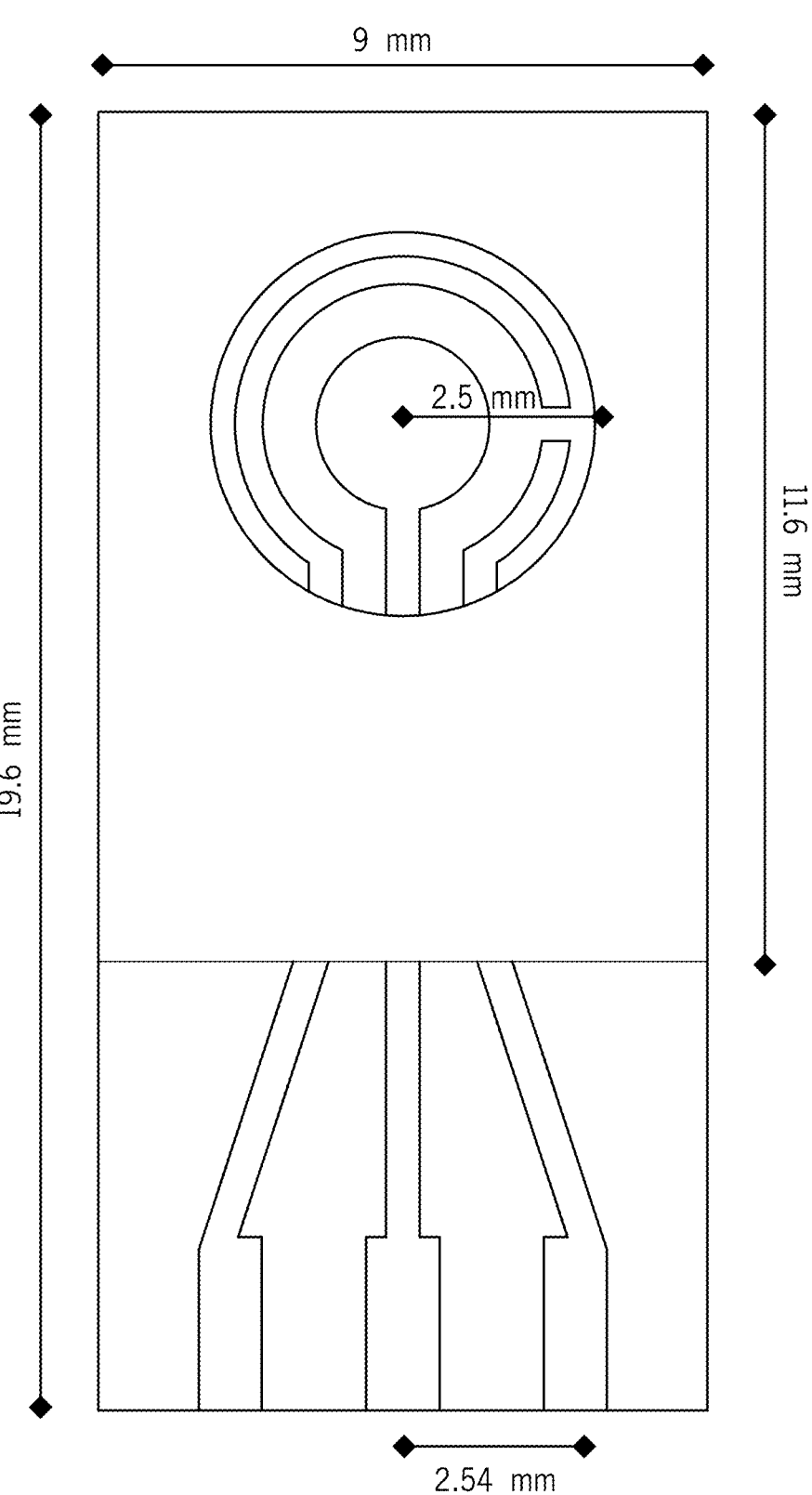
FIG. 18 shows a schematic of a tape-based DO sensor.

The tape-based sensor interface for containing the electrolyte solution above the Clark-type sensor was fabricated as using Type-490 electroplating tape (3M), as seen in FIG. 18. Two pieces of electroplating tape were cut to form a circular well (5 mm diameter/25 μm height) using a biopsy punch. The first layer was attached directly to the glass substrate, containing the electrolyte solution, then 10 μL of electrolyte solution (0.1 M KCl) was pipetted onto the electrode surface. To entrap the electrolyte solution, a small square (8 mm×8 mm) of the 25 μm thick FEP membrane was attached to the second piece of electroplating tape and then carefully attached to the first layer, such that no bubbles were trapped in the well. This method of encapsulation was used to minimize the distance between the FEP membrane and the sensor surface, ensuring that only diffusion through the FEP membrane would limit sensor response time. To prevent evaporation of the electrolyte solution through the FEP membrane, the sensors were stored in DI water between successive measurements.

Having addressed the assembly challenges from previous generations of the sensor interface, this iteration proved to be effective for the measurement of dissolved oxygen. By replacing the 3D-printed part with electroplating tape, the cost and assembly time per sensor was greatly reduced. Additionally, the simplicity of the modification provides a clear path towards scaling down the sensor size without needing to redesign an entire accompanying interface. Several aspects of the sensor assembly can be improved. The electroplating tape at times can remove the metal traces if not applied properly and the current application is limited to a single process flow, such that sensors are assembled manually one at a time. However, this electroplating tape method does lend itself to wafer level assembly in the future by using appropriately laser cut materials. The tape-based FEP attachment scheme offers a highly adaptable method for creating an electrochemical well, using a minimal amount of electrolyte solution, hence the diffusion limited properties of the chemical reaction become entirely dependent on the physical characteristics of the gas permeable membrane. Extensive use of this assembly will be discussed in the following sections.

bPod Platform Design and Assembly

Electronic Module

Several considerations for the design of the electronic module to achieve real-time wireless sensing in an aqueous environment were explored. Among these were low power consumption, small form factor, sensor calibration, and robust device to device communication. In FIG. 3, the overview circuit schematic is shown, outlining the connections between the electronic components. The electronics system contains a (1) BLE 4.0 microcontroller for data processing and transmission to an external user device, such as a mobile phone or laptop, (2) an analog-front-end (AFE) portable potentiostat readout circuit to bias and read the signal from the electrochemical sensor, (3) a single 3.7 V lithium polymer (Li—Po) battery with 14 mAh capacity and 30 mA maximum discharge current, and (4) a linear voltage regulator to stabilize and step-down the battery output to 3.3 V for each of the electronic components. Finally, the electronic module is attached to a 2.54 mm pitch card edge connector (CEC) in order to interface with the DO sensor assembly.

Potentiostat IC—LMP91000

The readout circuit for this application included a single AFE potentiostat integrated circuit (IC), namely the LMP91000 from Texas Instruments. This IC, though primarily designed for gas sensing, was instead operated for the amperometric measurement of DO, and has been demonstrated in numerous portable miniaturized analytical devices.

Figure 19:
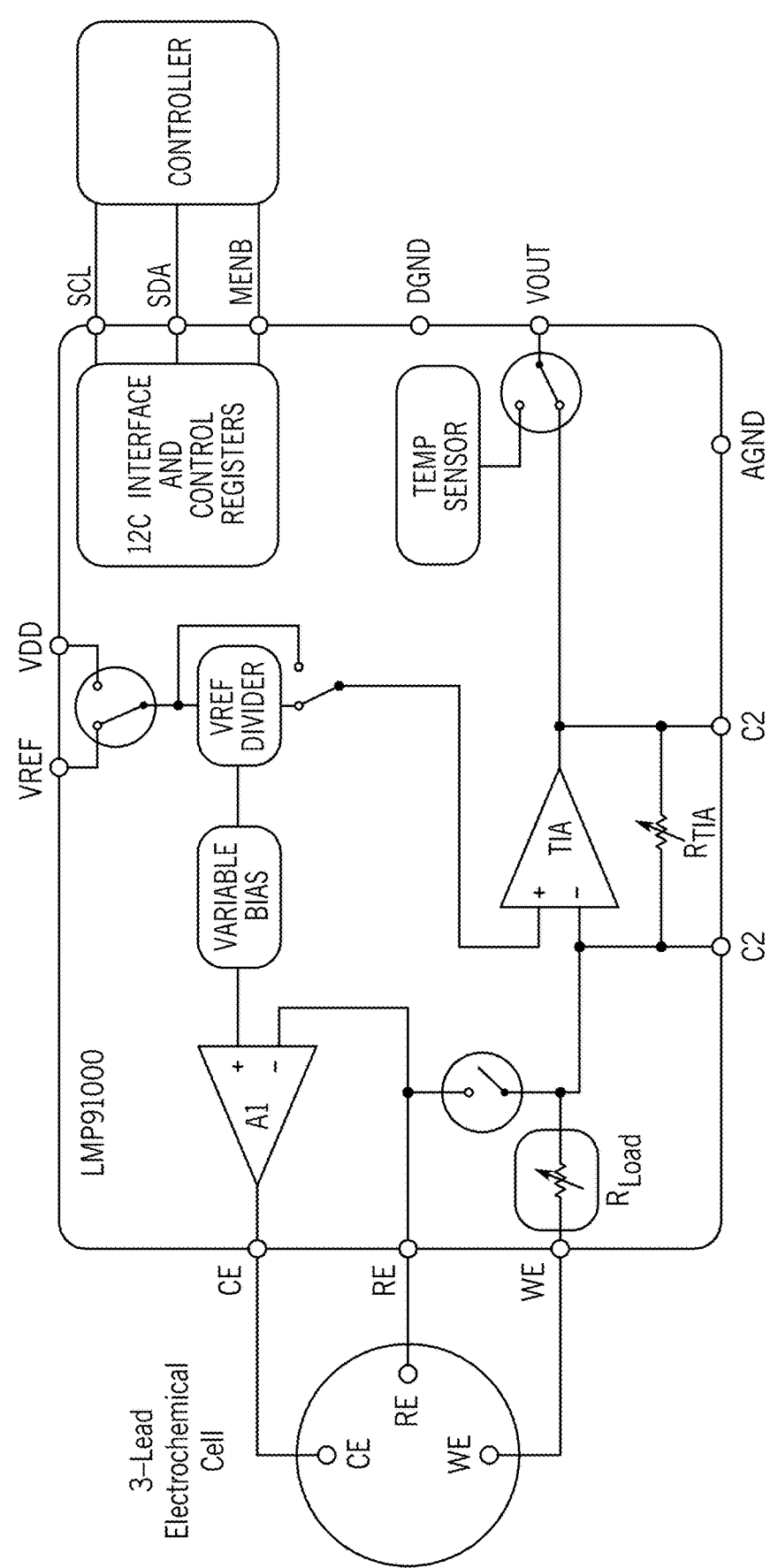
FIG. 19 shows a schematic diagram of LMP91000 AFE from Texas Instruments.

As discussed herein, the desired sensor configuration may include three-electrodes: a working electrode (WE), a reference electrode (RE), and a counter electrode (CE). The primary function of the potentiostat IC is to directly interface with the sensing electrodes, providing both a stable voltage bias across the WE and RE to stimulate an electrochemical reaction, as well as to convert the current response to an analog voltage. To better understand how the LMP91000 functions, it is best to divide the device into several operational blocks. These include a control loop, a transimpedance amplifier (TIA), temperature sensor, and an inter-integrated circuit ($I^2C$) interface as shown in FIG. 19.

Microcontroller Unit (MCU)

Bluetooth Low Energy (BLE) Module—BGM121

Compared to other wireless modalities, BLE boasts a small form factor and low-power consumption at high data rates and easy integration with user devices such as smartphones. The Silicon Labs BGM121 SiP chipset (6.5 mm×6.5 mm×1 mm) was chosen for this application and includes a programmable microcontroller, an integrated 2.45 GHz transceiver antenna, and a flash memory unit (to store code that runs the MCU). The internal inverted-f antenna provides an adjustable+8 dBm transmission signal at a 2.45 GHz excitation frequency. To correct for detuning due to the surrounding media, the length of the antenna ground plane may be modulated; an increase in the length corresponds to a decrease in the resonant frequency and a shortening of the ground plane results in an increase in the resonant frequency. The BGM121 utilizes the Low-Energy protocol described in the Bluetooth 4.0 specifications with a footprint of 6.5 mm×6.5 mm and a height of 1.0 mm. For development of the prototype the BGM121 radio board, a pre-soldered PCB with a sufficient ground plane was used. The PCB allows the design and verification of the rest of the circuit components as well as the DO sensor without having to design an RF PCB layout for the internal antenna.

Figure 20:
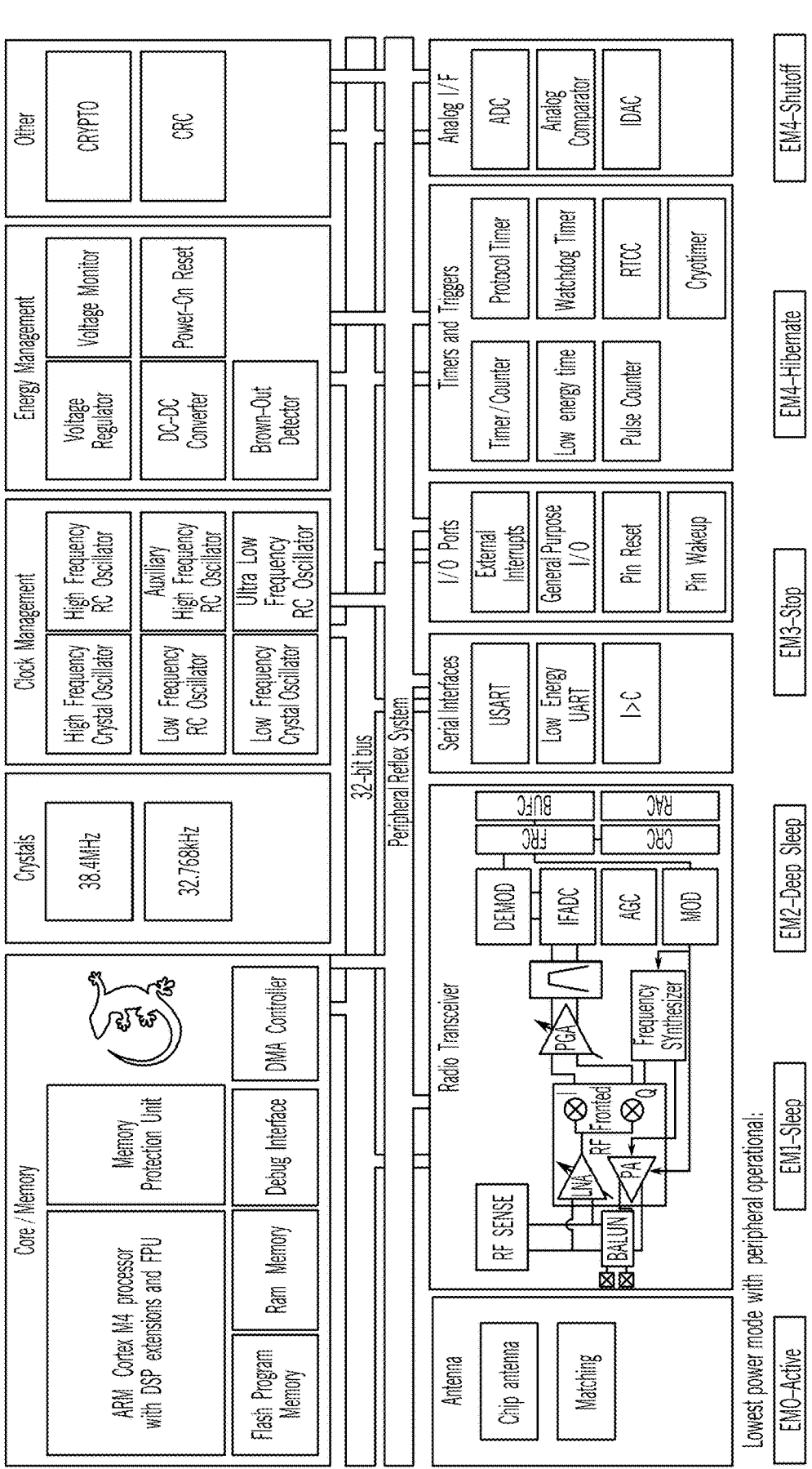
FIG. 20 shows a Schematic of available peripherals for a BGM121 microcontroller.

The core peripheral and energy mode operational guidelines for the BGM121 are shown in FIG. 20. Each function is colored to correspond to the energy mode necessary for its use. Ports are defined as letter blocks and allow programmable access to the device peripherals. The available peripheral pinouts include a 10-bit analog-to-digital converter (ADC) for digitizing sensor data, several general-purpose input-output (GPIO) pins used for toggling the enable pins of electronic components, and two $I^2C$ lines allowing bidirectional communication between the LMP91000 and the BGM121. One of the GPIO pins toggles the $I^2C$ enable on the LMP91000, which allows $I^2C$ communication when the value is low. The bPod relies on $I^2C$ to configure the LMP91000 to handle a variety of sensor types and excitation biases. The other GPIO pin toggles the capabilities of the voltage regulator connected to the LMP91000; when low, the voltage regulator will simply pass the battery voltage. Doing this reduces the power consumption of the voltage regulator. Three pins: PF0, PF1 and RESET are used to program the microcontroller along.

Energy Modes

The BGM121 utilizes several energy saving modes to control current consumption depending on the required function, thus extending the operational lifetime of the device. When transmitting and receiving data, the device enters an "active" mode and draws 25 mA of current. While idling for an event interrupt to occur, the device is set to "deep sleep" mode where it consumes 2.5 µA and can also enter a temporary shutdown of the device using "hibernate" mode consuming 0.58 µA.

Figure 21:
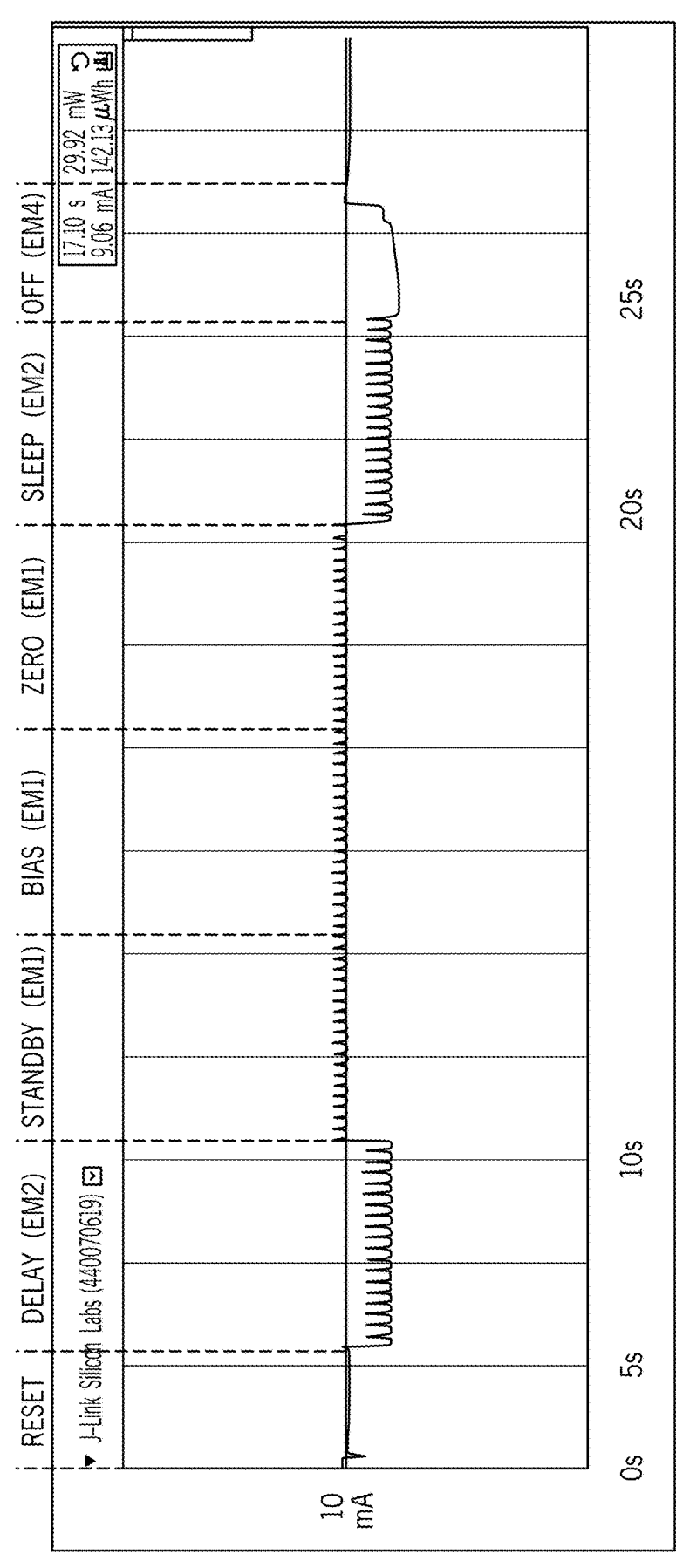
FIG. 21 shows an energy profile of the BGM121 using Simplicity Studios Energy Profiler.
Figure 22:
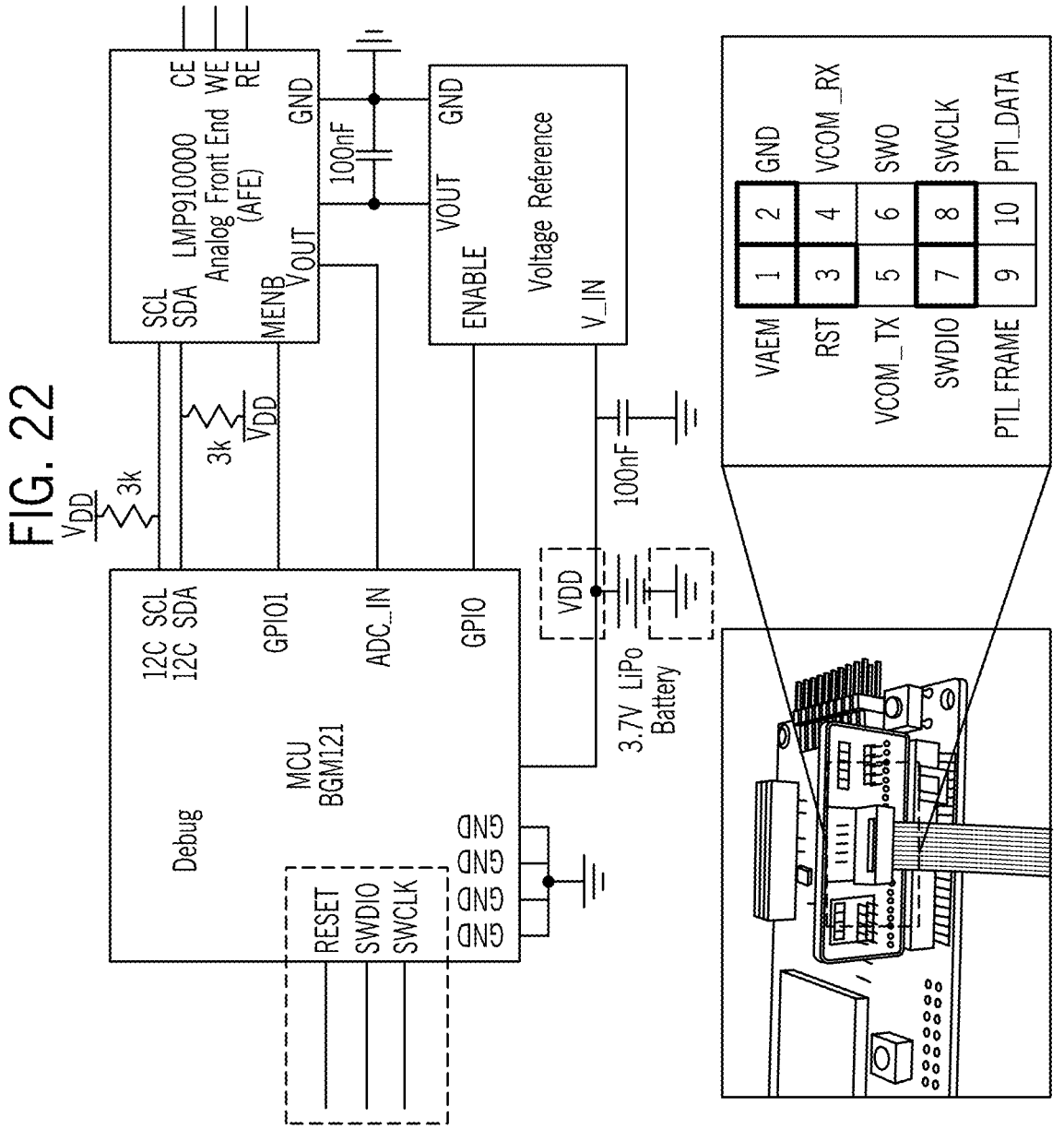
FIG. 22 shows a schematic depicting external debugging of the BGM121 using the WSTK.

To verify the successful transition into the different energy modes of the BGM121, the circuit was connected to the Simplicity Studios Energy Profiler. This utilizes current measurement circuits on the Silicon Labs wireless starter kit (SLWSTK6101C), or WSTK, and the computer program to measure the current consumption from the microcontroller. FIG. 21 shows one iteration of the measurement sequence of the energy profile of the BGM121 using Simplicity Studios Energy Profiler. Spikes represent data pulses, while the overall shifts indicate the switching of the energy mode. The sequence can be customized for the timing of the DC bias and setting of the correct energy modes. The energy modes in the figure are denoted EM1 (high energy mode for data acquisition with the UART), EM2 (sleep mode while the device is waiting for an event), and EM4 (shutdown—everything is off except for a cryotimer that will reset the device to reinitialize and start again). The measurement sequence is described by the following modes: DELAY (wait to start measurements), STANDBY (LMP91000 wakes up and the configuration is switched to a zero bias), BIAS (−0.5 V voltage bias applied between the working and reference electrodes), ZERO (bias returned to zero), SLEEP (LMP91000 put to sleep and UART communication stopped), and OFF (most functions disabled for extended hibernation).

Debugging of the MCU

Programming of the BGM121 was performed using the Silicon Labs IDE, Simplicity Studios 4. Debugging of the electronic module was performed either by connecting the BGM121 radio board directly to the starter kit, or by attaching 24-gauge wires directly to the programming pins. A Simplicity Debug Adapter (SLSDA001A) was connected to the starter kit and connected with wires to externally flash the code onto the device. The five necessary pins were the Reset, SWDIO, SWCLK, GND, and VDD as shown in FIG.

22. Connections highlighted in red are made between the electronic module and the WSTK. Throughout the operation of the electronic module new application code is flashed to the device in this manner.

GATT Profile

For communication between a Bluetooth enabled device, smartphone or PC, and the bPod a GATT profile is generated, detailing how data is exchanged between the two devices. This information is organized into a hierarchy of services and characteristics which contain the data that is to be sent or received. More information can be found in the Bluetooth v5.1 specification manual. There are two main characteristics used for the bPod prototype. The first characteristic, sensor data, contains the DO measurement and is able to both display the information on the screen, as well as save the information to a .csv file for further analysis. The second characteristic, Command, allows writing data to and the control of the bPod by an external device. This characteristic was programmed to control the operational state of the bPod, defining the energy mode, the calibration, and the on/off state of the device. This will be discussed in detail below. The device name and default appearance are also contained within the GATT profile, as shown in FIG. 23.

There are three services incorporated into the coding of the sensor platform. The first is the "Generic Access" service which includes the device name, such as bPod, as well as an appearance characteristic that associates the platform to known Bluetooth devices, such as a phone, computer, or watch. The second service describes the device information and uses two characteristics. The first characteristic identifies the name of the manufacturer and details about the hardware and software specification. For this device the BGM121 is manufactured by Silicon Labs and is part of the Blue Gecko product line. This is used primarily to determine which version of the Bluetooth software SDK or which hardware revision is currently in use. The final service, as mentioned previously, is a custom service containing information on the sensor output. This information is represented as the sensor data characteristic, which provides the DO concentration transmitted by the sensors as a 16-bit integer as measured by the 12-bit ADC. The values are converted into the appropriate voltage and current units using the exported .csv file in Microsoft Excel (Microsoft, Redmond WA). Since the steady state response time of the sensor can vary, proper conversion requires the use of "For" loops, which lock-up the bPod from transmitting the next data point until the sensor response is complete. The command characteristic provides remote access to the bPod, allowing external commands to trigger interrupts and to be used for configuration. The characteristic is an 8-bit write command used to place the bPod into one of four operational states, used to wake the device from sleep mode or shut off for a specific amount of time. These operational states are discussed in detail in the section below.

Operational States

The BGM121 microcontroller was programmed to receive commands from a modified BLE app (Silicon Labs) for data acquisition and transitioning the device into multiple operational states. When a command is received by the microcontroller, it enters one of four operational states: OFF, CALIBRATE, MEASURE, and STAND-BY. The default state of the device is triggered by resetting or reconnecting to the bPod through the app, placing the device in low power mode, or EM2. The OFF state places the device into the lowest energy (hibernate) mode, effectively turning off the device so that it consumes minimal current. In this mode, the device will disconnect from the phone app and will not receive commands, which is ideal for stopping an incorrect measurement; an internal timed wake-up event is programmed using the cryotimer to turn the bPod back on after a specific amount of time, which can vary between 1 second and 18 hours. This feature allows the device to remain in the lowest energy mode when not in use, as well as provide a software reset, which can be useful to reinitialize the bPod. Next, the CALIBRATE, or single-shot, state performs a single measurement sequence. This sequence intermittently toggles between the active mode when transmitting data and the low power mode when operating the BGM121 peripherals. Similarly, the MEASURE state will perform the measurement sequence a finite number of times, alternating the configuration of the LMP91000 between the active mode when data is recorded and a three-minute wait period between measurements, where the device is left in low power mode. Finally, the STANDBY state configures the sensor for monitoring the open circuit potential, but does not transmit the data, keeping the device in a low power state. This allows for sensor conditioning if necessary, prior to applying a voltage bias. The generic process flow for the MEASURE operational state is shown in FIG. 24. By utilizing software timers and external write commands to control the state of the device, the bPod operates autonomously towards the electrochemical monitoring of DO.

Custom Android App

Figure 25:
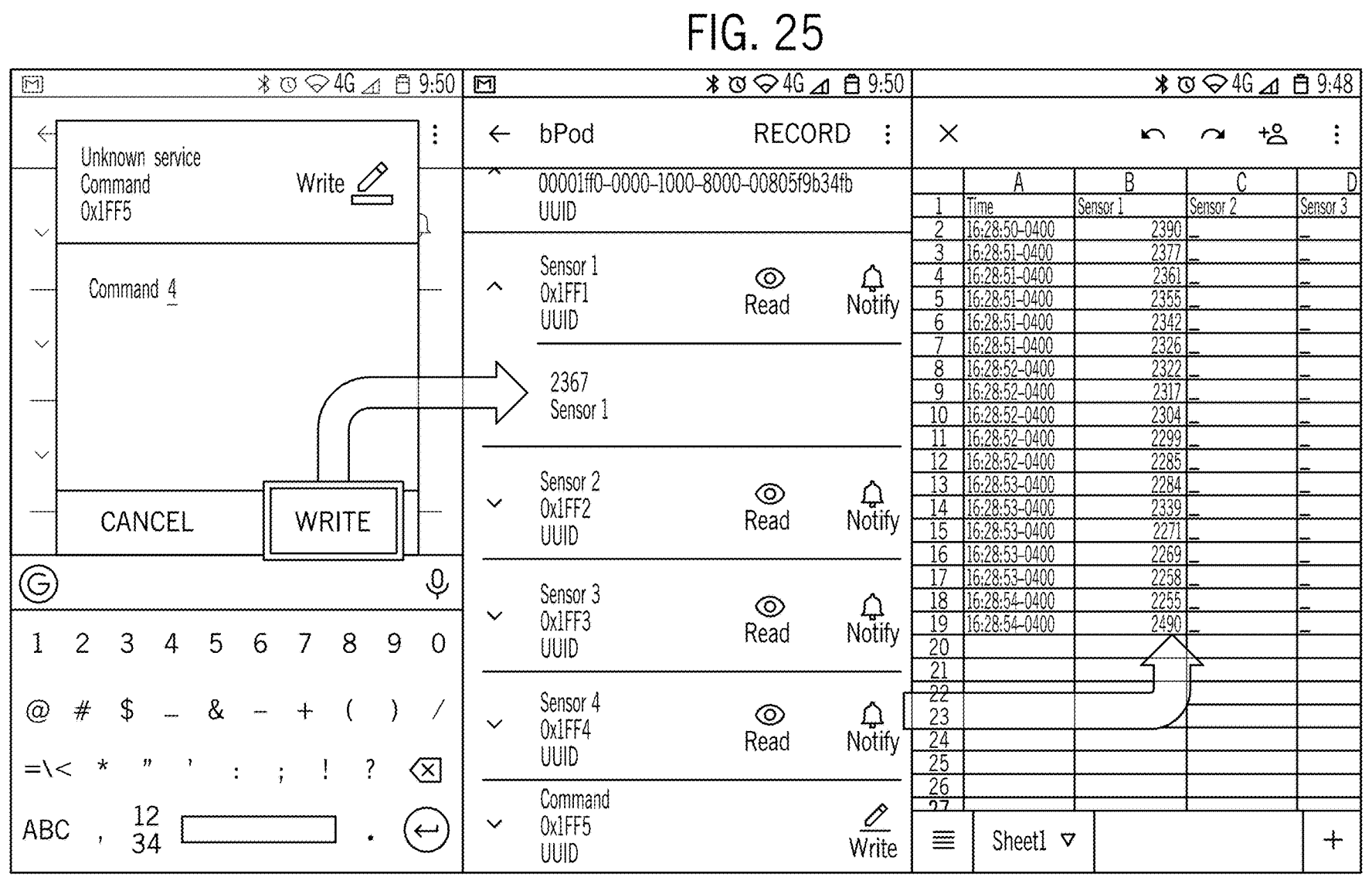

To receive data from the bPod, a custom app (modified from a Silabs demonstration app) was created to send write commands to the BGM121, as well as store and display DO concentrations on the external user device, namely the phone or PC. FIG. 25 shows the command prompt that allows the user to type in a 1-byte command. The "4" present on the screen (left) corresponds to the CALIBRATE state, for example. Next, under the 'Sensor 1' tab (middle), the data begins to populate and refresh onto the screen. The measurement from the bPod is both timestamped by the phone and formatted into an Excel spreadsheet (right). For future development of the bPod coding, it is ideal to perform all post-processing of the data off of the microcontroller. In this manner, the MCU will be able handle interrupts as they occur to reduce unnecessary power consumption and time delays in the device, hence reserving the MCU for event scheduling, sensor transduction, enhanced power management, and data transmission.

Card Edge Connector (CEC)

As discussed herein, interfacing of electrochemical sensors with an electronic module is subject to numerous challenges. A robust connection was necessary for the proper conditioning and measurement of the sensor. The bPod accomplishes this by using a two-sided female 6-position CEC with pin pitch of 2.54 mm (TE Connectivity), ensuring tight physical connections between the electrode contacts and electronic module as shown in FIG. 26. Therefore, multiple sensors could easily be connected and disconnected to a singular platform (electronic module) without using other processes such as wire-bonding or soldering to make the sensor connections. The bPod utilizes 3-pins at a given time and the connections are attached directly to the WE, RE, and CE inputs of the LMP91000. The dimensions of the CEC are 14 mm×10 mm×8 mm with an acceptable card thickness of 1.37 mm-1.78 mm. Due to these size parameters, the DO sensor dimensions were desired to be of sufficient length and width for inserting into the adapter, as well as thick enough to maintain proper contact. The specifics regarding the sensor fabrication dimensions were discussed above. The Pyrex sensor substrate (500 μm thickness) was susceptible to dislodging from the adapter, therefore additional spacers were needed to supplement the connection between the CEC contacts and those of the sensor.

3D-Printed Spacer

Figures 27A, 27B, 27C:
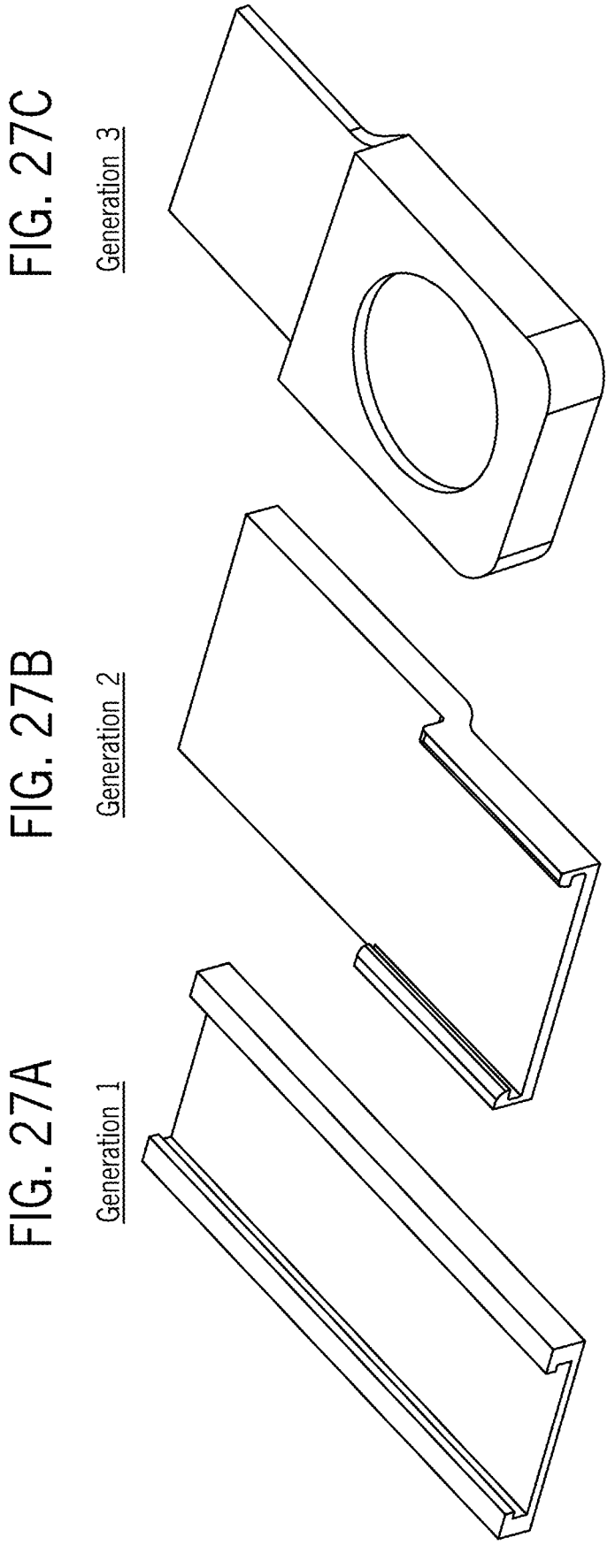
FIG. 27A shows a generation of a 3D-printed spacer used for supporting the sensor when interfacing with the bPod.
FIG. 27B shows another generation of a 3D-printed spacer used for supporting the sensor when interfacing with the bPod.
FIG. 27C shows yet another generation of a 3D-printed spacer used for supporting the sensor when interfacing with the bPod.

For each generation of the 3D-printed enclosure, the electrochemical DO sensor was supported by a 3D-printed spacer. The function of this part was to add thickness to the sensor, which ensured a robust connection with the CEC of the electronic module, as well as supported the sensor, making it less fragile during leak-proof sealing, which was discussed above. The various spacer designs are displayed in FIGS. 27A-C, related to the generation of the bPod enclosure for which they were utilized. Discussion of how the spacers assisted with the creation of an electrochemical well was discussed above. Alternatively, the spacer could have been incorporated into the main 3D-printed enclosure, however, iterative design of tolerances would have proven costly and time consuming.

Power Management

A key consideration for the design of a long-term embedded sensing system is careful power management to preserve battery life. Adequate current was provided to the electronic module to satisfy the power consumption of each measurement processes throughout the bPod lifecycle. The device lifetime is affected by the choice of battery, the power management of the electronic energy modes, and implementing an appropriate duty cycle for bioprocess monitoring. As discussed herein, the operational states were developed to ensure the bPod remains in a low power state unless otherwise necessary. In addition, monitoring parameters such as measurement duration, sampling rate, and downtime between measurements were modulated to limit power consumption. Therefore, for short- to long-term monitoring, the choice of battery for the bPod would be critical to enable extended monitoring applications.

Battery Selection

The bPod power source is contained within the packaging, and as such there exists a tradeoff between battery size and capacity. Several common battery chemistries used for portable applications today are silver oxide, lithium/manganese dioxide, lithium/iodine, lithium/silver vanadium oxide, zinc air, lithium ion (Li-Ion), and lithium polymer (Li—Po). Silver oxide batteries are frequently used for ingestible capsule research and are based on a silver oxide cathode and zinc anode reaction within an alkaline electrolyte. Despite a small feature size (~10 mm), adequate capacity, and excellent 5-7 year shelf life, silver oxide batteries are not always capable of supplying sufficient instantaneous current for wireless communication. Li—Po batteries based on a polymer electrolyte, however, can provide the necessary instantaneous current and are rechargeable, but do not scale quite as efficiently as silver oxide in terms of capacity to size ratio. Therefore, the prototype bPod utilizes a 14 mAh Li—Po battery (GM301014H) from PowerStream with a 10 mm×15 mm size for early validation of the system. This battery can supply an average of 3.7 V at up to 140 mA, which are sufficient for powering the electronic module, particularly for larger bPod embodiments (e.g. 60 mm dia.); in smaller bPod embodiments (e.g. 20-25 mm), a 3.3 V CR2032 coin cell and a 3.5 V Lithium Thionyl Chloride battery LTC-3PN were used. Bioprocess monitoring within bioreactors may require device lifetimes on the order of a couple weeks, therefore future battery options would ideally be equipped with a larger capacity (>500 mAh).

Voltage Regulator

As the battery discharges, the voltage that it supplies drops. A voltage regulator is needed to maintain constant voltage supply to the embedded system. A TLV7033 linear voltage regulator was chosen for the bPod, which stepped down the 3.7 V input from the Li—Po battery and held the supply rail at a steady 3.3 V for the LMP91000. The BGM121 utilized an internal DC-DC converter, though was eventually also connected through the TLV7033. It was found that variations in the supply voltage to the BGM121, when not regulated, had a significant effect on the ADC resolution, thereby reducing the accuracy of the sensor. This was verified experimentally and explained below.

The BGM121 DC-DC converter supply voltage ($V_{DD}$) variation was monitored through the ADC to validate this effect of $V_{DD}$ for device measurement. To determine this, a power supply was connected to the device and swept at a 0.1 V interval from 3.0 to 3.7 V, the expected range for the proposed Li—Po battery. It was found that for potentials larger than 3.3 V, the internal DC-DC converter for the BGM121 was unable to maintain 3.3 V, thus affecting the ADC reference voltage. The output voltage of the ADC was configured to output $V_{DD}/2$ shown in Table 3-1 below. The 'actual' value was measured using a multimeter probe placed at the output of LMP91000, whereas the 'measured' value was read from the smartphone. From this experiment, it was determined that the BGM121 internal DC-DC converter was not sufficient for VDD greater than 3.3 V, therefore the MCU power rail connection was moved to the voltage regulator as opposed to connecting directly to the battery.

Table 3-1 below summarizes the output voltage of the LMP91000 under several different voltage supply rails. The 'actual' measurements were recorded directly from the LMP91000 output, whereas the 'measured' measurements were recorded through the BGM121 ADC.

TABLE 3-1

| Applied Voltage (V) | Actual (V) | Measured (V) |
|---|---|---|
| 3.0 | 1.619 | 1.619 |
| 3.1 | 1.620 | 1.620 |
| 3.2 | 1.620 | 1.620 |
| 3.3 | 1.620 | 1.620 |
| 3.4 | 1.627 | 1.579 |
| 3.5 | 1.627 | 1.534 |
| 3.6 | 1.627 | 1.492 |
| 3.7 | 1.628 | 1.452 |

Assembly of bPod Electronic Module

Figures 28A, 28B:
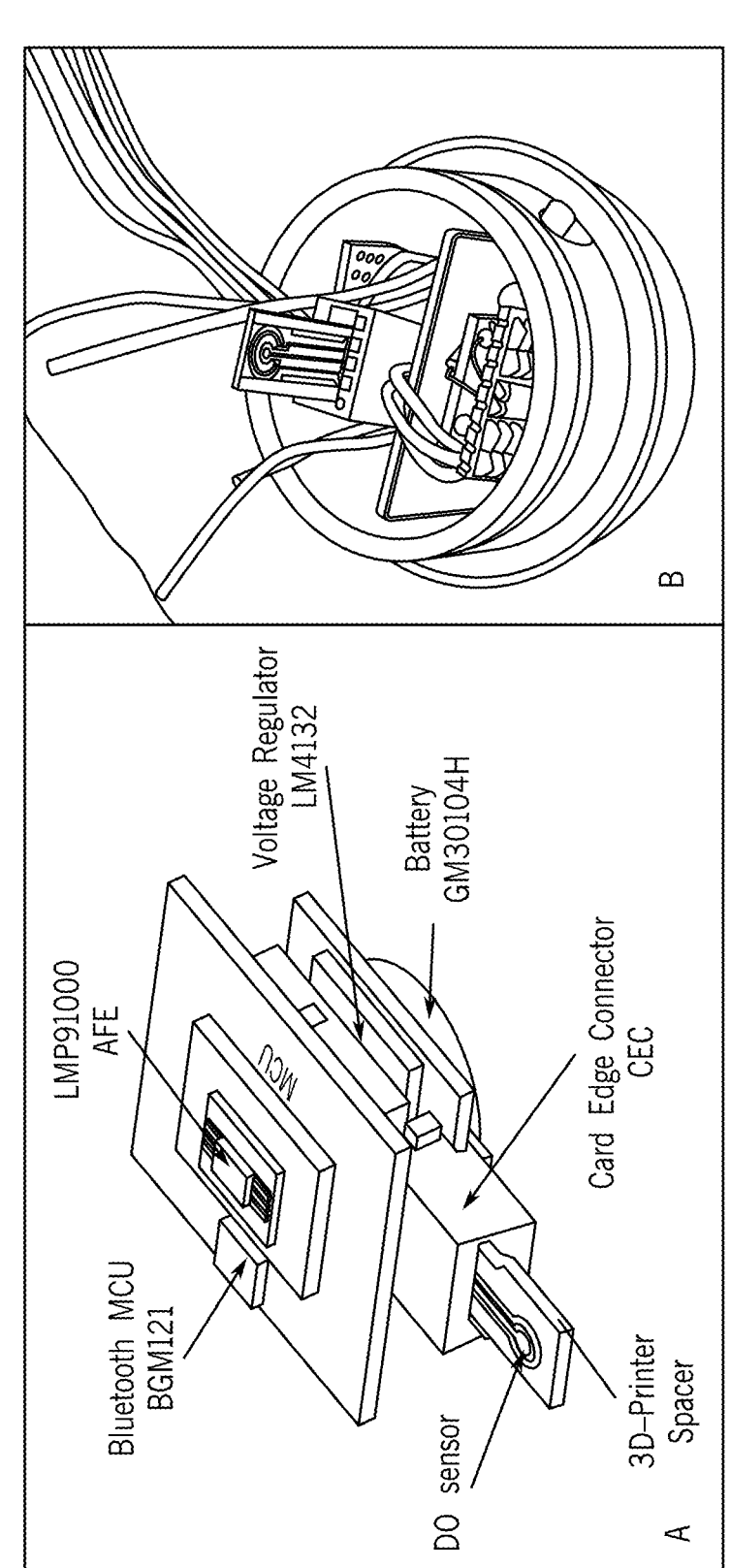
FIG. 28A shows an electronic module and the orientation used to fit within the 60 mm bPod enclosure (45 mm cavity).)
FIG. 28B shows the module of FIG. 33A arranged to fit inside of the 3D-printed enclosure.

The following section briefly discusses the assembly of the hand soldered electronic module for the bPod. A prototype integrating the various electronics and interface components was developed to identify potential challenges and viability within an enclosed package for underwater testing. FIG. 28A provides an illustration of the electronic module and the orientation used to fit within the 60 mm bPod enclosure (45 mm cavity).) FIG. 28B shows the module arranged to fit inside of the 3D-printed enclosure.

In one configuration, the electronic module has 5 separate components (together with accompanying electrical contacts, connectors and connections for communication among the components): (1) LMP91000, (2) coin cell battery, (3) linear voltage regulator, (4) the CEC, and (5) the BGM121 radio board. Individual IC's were first validated using the WSTK and LMP91000 evaluation board (LMP91000EVM). Assembly of the electronic module involved, first, of soldering each IC to a dual inline-package (DIP) adapter that matched the standard land pattern of each chip. Then, long wires (24 gauge), coupling capacitors, and pull-up resistors were soldered onto an FR4 Veroboard cutout, which has a patterned metal surface with mixed vertical and horizontal metal traces (similar to commercial breadboards). Finally, the DIP adapters were then soldered on top. The FR4 Veroboard were then oriented about the BGM121 radio board such that they directly inserted into the bPod enclosure. The IC's were connected to the BGM121 radio board with 24 gauge wire according to the schematic diagram in FIG. 3. Finally, wires were trimmed and wrapped around the BGM121. The orientation shown in FIG. 28B shows the electronic module inserted into the bPod enclosure. The use of connectable wires attached to the BGM121 radio board enabled easy removal of the electronic module from the 3D-printed enclosure, as well as on-demand flashing of application code to the MCU.

Device Operation

When the bPod is powered on, the BLE software begins to broadcast advertising packets at a 200 ms interval in order to pair with a user device. These packets contain information from the GATT profile, such the device name, as well as other custom characteristics embedded into the code. An external device, typically a smart phone, will be able to discover and provide a list of nearby Bluetooth devices containing this information and the aforementioned services. When the bPod connects or is paired with the custom app, the broadcast packets become less frequent, only often enough to maintain the paired status. When paired, by default, the bPod stays in a low-energy state (EM2) until an event interrupt is triggered. An interrupt, for reference, is a conditional signal sent to the processor of the MCU indicating a specific routine that is immediately executed before proceeding to the same line of code prior to the interrupt trigger. The two main interrupt handles used in the programming of the bPod were external interrupts, triggered by write commands sent from the app, and software timers, triggered by internal clocks.

Amperometric measurements performed with the bPod will be presented below. The platform was submerged into a DI water solution and the DO % saturation adjusted to steady state conditions between 0 and 100%. Further details discussing how these values are generated will be described below. For calibration of the sensor, chronoamperometric measurements were performed using the CALIBRATE operational state. First, the LMP91000 AFE is configured for amperometric measurements, used for three-electrode sensors. Next, the output voltage is recorded by the BGM121 ADC, while in low power mode, before momentarily toggling to active mode to wirelessly transmit the 16-bit value to the phone. This switching is repeated for the next recorded value every 50 ms for 25 s, completing one measurement. The CALIBRATE command is then sent to the bPod when the next steady state condition is achieved within the bioreactor. For real-time monitoring of DO with the bPod, the MEASURE operational state is used, triggering a similar energy mode that toggles once every 5 minutes, recording values every 50 ms for 25 s to produce a characteristic chronoamperometry curve. After each measurement sequence, the program checks the number of measurements performed; once the desired amount of data has been collected the device will return to deep sleep mode until another external command is given. A duty cycle of −14% was determined to extend the current battery capacity from a couple hours to a couple of weeks.

3D-Printed Enclosure

A 3D-printing approach was employed as a rapid, low-cost prototyping method for the bPod enclosure, creating packaging to (1) protect the custom electronic module, (2) seal the device from the liquid environment, and (3) support contact with the fabricated electrochemical sensor. There exists a variety of 3D-printing techniques suitable for generating small robust enclosures, including fused deposition modeling (FDM), stereolithography (SLA), and Polyjet printing. However, not all printing techniques are able to produce leak-proof features using biocompatible materials without additional post-processing (due to gaps between adjacent print layers). Biocompatibility and preservation of the electronic module in a liquid environment is critical for the successful operation of the system. To this end, the bPod was printed using a Polyjet printer, the Objet500 (Stratasys, Eden Prairie, MN) which employs UV-curable photo resins to produce high resolution prints with low moisture retention (1-2%). A clear biocompatible resin commonly used in dental implants, MED610, in conjunction with a dissolvable support material was used to 3D-print the packaging for the encapsulation of the electronic module.

Architecture and Dimensions

Figure 29:
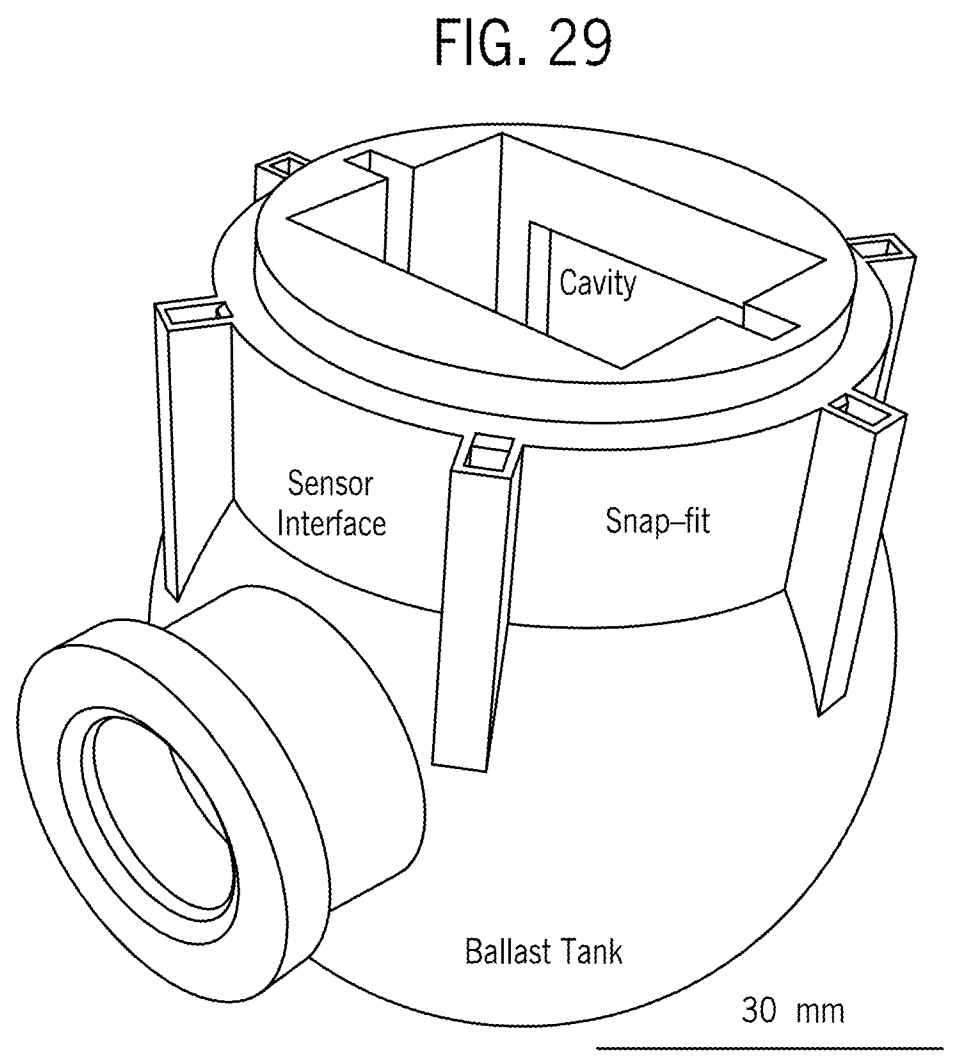

The bPod was designed with a 60 mm diameter to incorporate the electronic module and sensor interface into a minimally viable product for monitoring DO. A larger module would allow for more flexibility when prototyping the electronics, as well as support successive testing of DO sensors. The ideal architecture for the bPod packaging was a sphere-like 'marble' with a target diameter of 25 mm (diameter of quarter). Smaller form factors would reduce potential interactions with the bioreactor impeller blades during stirring and agitation as well as minimize the shear effects of the device on cell culture products. However, starting at the 60 mm size scale, a benchtop version could be validated with all of the system components before committing resources to a printed circuit board design. Additionally, the use of the BGM121 radio board (40 mm×35 mm) allowed for evaluation of the wireless communication capabilities of the bPod without encountering propagation signal losses due to an inefficient ground plane or PCB layout. The spherical shape was inspired by submarine and buoy structures, which present a symmetrical distribution of mass and volume about the central axis of the bPod. Essential features for the bPod enclosure include a small cavity to hold the electronic module, interlocking seals for closing the device, adjustable mass for maintaining neutral buoyancy, and a sensor interface. FIG. 29 shows an early conceptual representation of the 3D-printed packaging. Though ultimately impractical for various reasons not discussed here, this design showcased several of the necessary features that later were integrated into the bPod.

bPod Enclosure Dimensions

Figure 30:
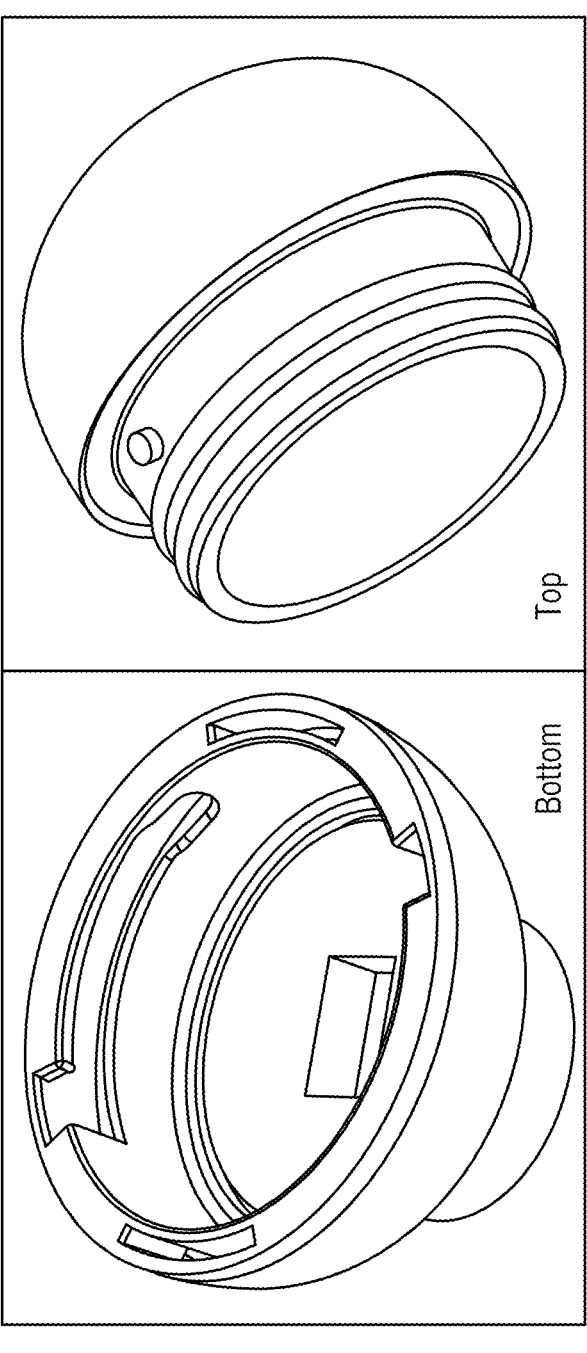
FIG. 30 shows a CAD drawing of the top and bottom halves of the bPod enclosure.

In one construction, the spherical pod has an outer diameter of 60 mm and was assembled from two attachable parts as shown in FIG. 30. The two halves (top and bottom) of the packaging were connected by a bayonet twist connector and sealed with three silicone O-rings. This allowed for switching various COTS components while designing the circuit, as well as improving the sealing of the packaging. A tolerance of 0.1 mm was used for the separation of the top and bottom parts, which press down onto an O-ring (55 mm inner diameter), and a tolerance of 0.45 mm for the two O-rings (50 mm inner diameter) used to create a leak-proof slip-fit seal. Silicon oil/grease and Teflon tape were incorporated to assist with O-ring sealing. The tolerance of the bPod enclosure was adjusted across several iterations to ensure that the seal was leak-proof. Moreover, application of a fine grit sand paper was necessary to smooth the 3D printed surfaces to ensure proper fitting between the two halves.

For achieving a neutral buoyancy condition two hollow cavities along the periphery of the package were included to allow additional weight or infill. The CEC was aligned using a 10 mm×14 mm×3 mm cutout, such that the sensor could be easily inserted into the electronic module. Finally, the sensor interface was designed to expose the sensing electrodes to the aqueous sample, while isolating the sensor contacts. The sensor interface geometry and leak-proof sealing were modified through three generations of prototype development, and evaluated for reliability during sensor testing. Each generation of the sealing interface is described in detail below.

Generation 1: 3D-Printed Enclosure for Glucose Sensing

Figures 31A, 31B:
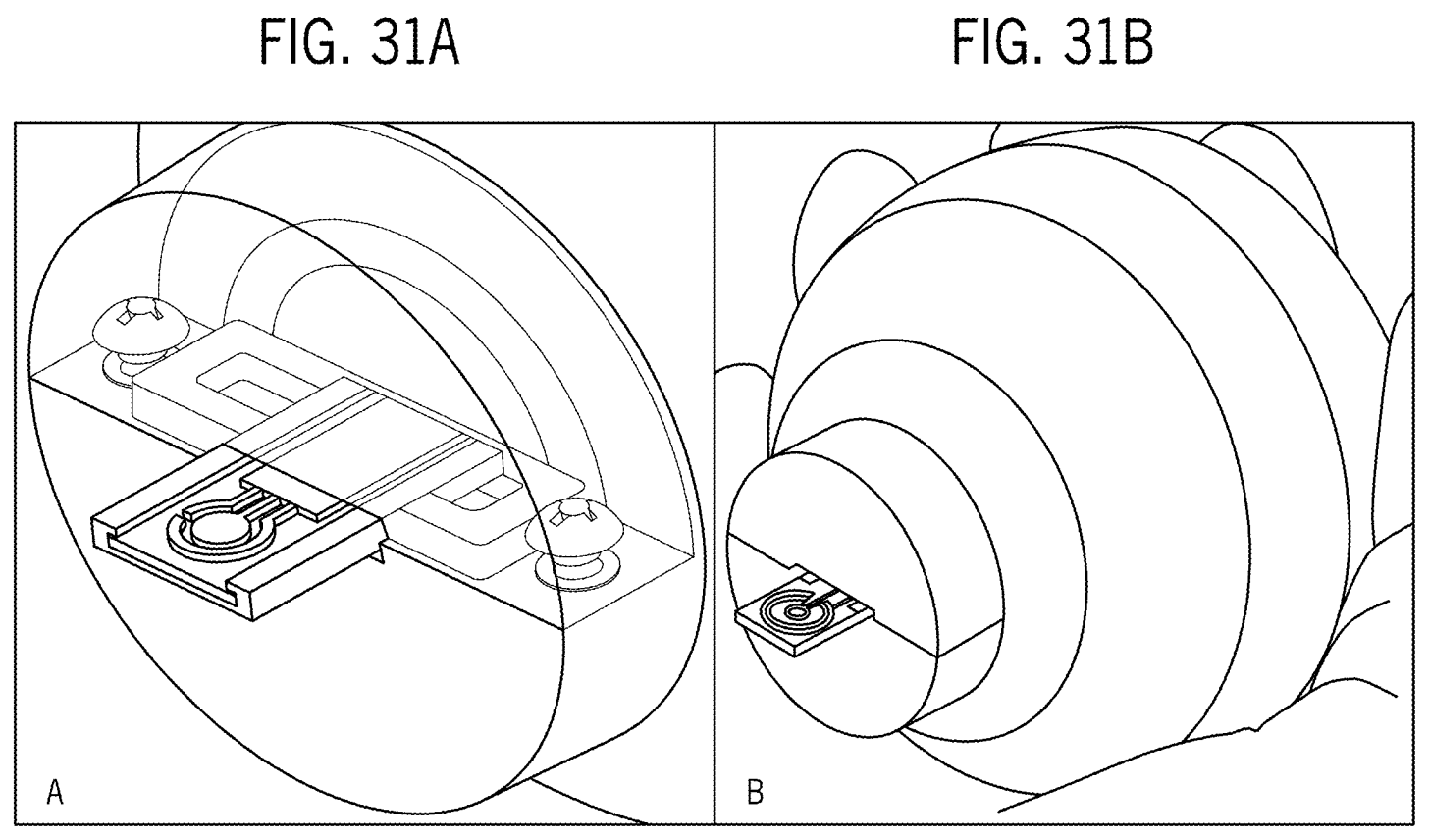

As discussed above, the initial motivations for generation 1 of the 3D-printed enclosure were to enable the sensing of glucose. The electrodes were exposed to the liquid environment without the need of an electrochemical well to stabilize the sensor measurement. For achieving a leak-proof seal three custom molded Polydimethylsiloxane (PDMS) gaskets were utilized to seal the bPod interior, as seen in FIGS. 31A and 31B. Details for the development of the generation 1 3D-printed enclosure and sensor interface are included in Appendix B. Due to issues with the PDMS seals leaking, difficulties with the PDMS fabrication, and concerns regarding exposing the sensor to the environment with minimal protection, the 3D-printed bPod enclosure (generation 1) and sensor interface design were significantly modified.

Generation 2: 3D-Printed Screw-Top Sensor Interface

The generation 2 bPod enclosure was designed to enable amperometric measurements of the fabricated DO sensors within a bioreactor. To accomplish this a 3D-printed screw-top sensor interface was utilized to form an electrochemical well integrated with the main 3D-printed enclosure, as shown in FIG. 16A and FIG. 16B. The design of the 3D-printed screw-top sensor interface was discussed above, and a detailed description of modifications from the generation 1 to the generation 2 bPod enclosure are discussed in Appendix B.

It was found that the generation 2 bPod enclosure encapsulation method hindered sensor performance. The excess distance between the membrane and sensor surface caused a delay for the diffusion of DO into the electrolyte well from the bulk solution. This time delay was on the order of 10 minutes, which is undesirable for bioprocess monitoring within bioreactors. Therefore, to decrease the response and equilibration time of the sensor, an improved sensor interface was designed in generation 3 of the bPod enclosure.

Generation 3: 3D-Printed Receptacle and Tape-Based Sensor Interface

Figure 32:
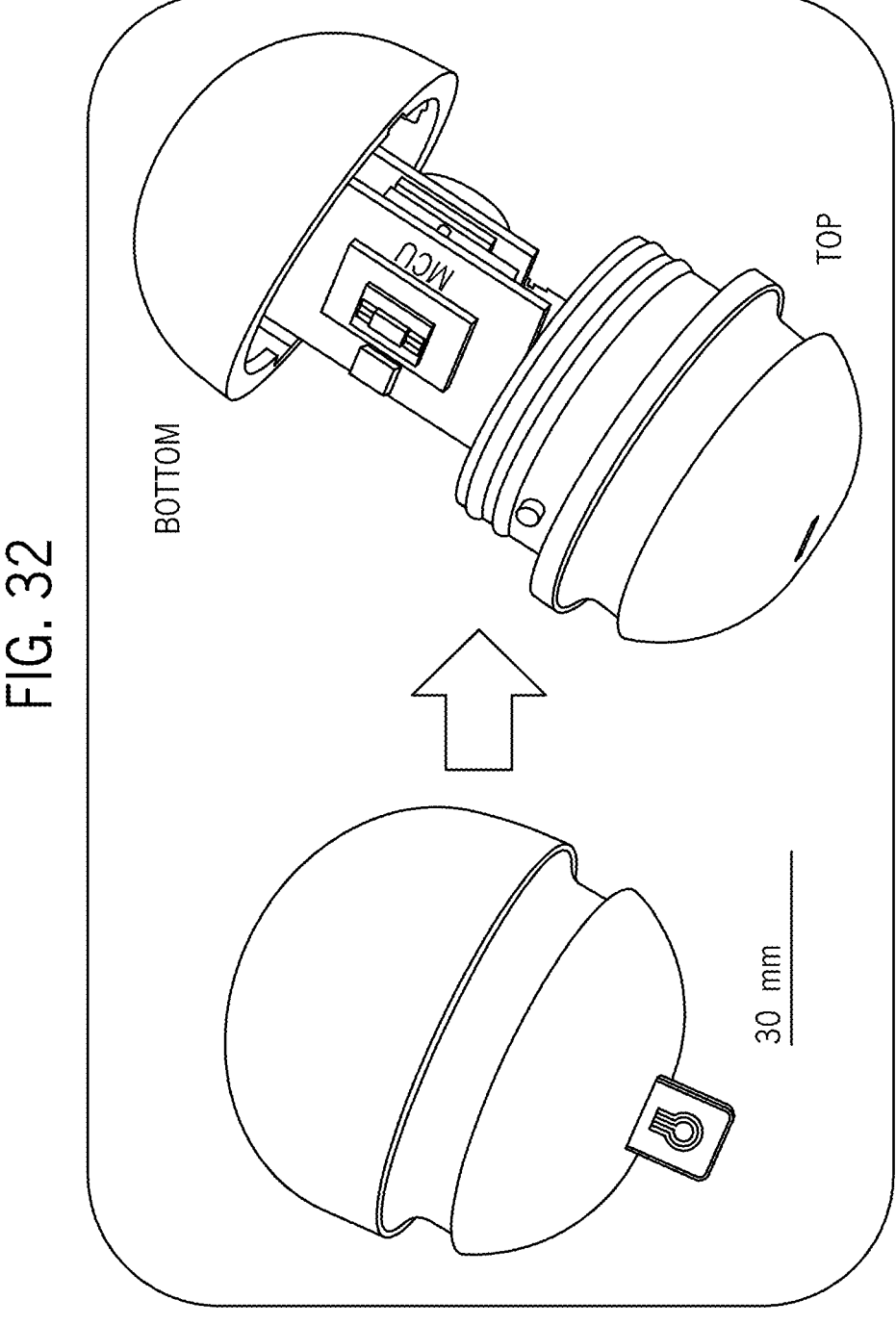
FIG. 32 shows generation three of bPod enclosure.

Generation 3 of the 3D-printed bPod enclosure greatly minimize the complexity of the sensor interface, by directly fabricating the electrochemical well onto the sensor rather than with the packaging, as was the case for generation 2. This approach preserved the integrity of the electronic module and improved consistency of the leak-proof sealing during testing. The aforementioned sealing interface (generation 2) was removed from the bPod enclosure and replaced with a 2 mm×10 mm slit. When the top and bottom parts are brought into contact and twisted along the interlocking pin a frictional force is applied to the electronic module due to surface roughness of the internal cavity. At times this resulted in cracking of the Pyrex electrochemical DO sensor or unseating of wires used to connect the electronic components of the electronic module. While this did not degrade any leak-proof features, it resulted in numerous failed experiments. Therefore, for the generation 3 enclosure, the slit location for the DO sensor was flipped from the bottom half of the bPod to the top, according to the previously defined orientation provided in generation 1. As a result, the torque experienced by the electronic module during the assembly of the device was completely removed, allowing the bPod to be open and closed freely. This change is reflected in FIG. 32 indicating the updated orientation.

For sealing the 3D-printed receptacle and the tape-based sensor interface discussed herein, water-resistant epoxy (Devcon, Hartford, CT) was placed between the sensor assembly and the bPod enclosure slit followed by 15 minutes of curing. For interfacing with the electronic module, the 3D-printed receptacle (generation 3 spacer) was designed and incorporated to add thickness to the sensor for insertion into the enclosure and robustness during handling.

Enclosure Summary

The 3D-printed enclosure had notably undergone many iterations to conform to the needs of the bPod system. The size of device was constructed to house the hand soldered electronic module. Future iterations will seek to miniaturize the packaging size, while also satisfying the sensor interface requirements. Current limitations to scaling the packaging dimensions are found with the electronic module and battery size. The electronic module form factor can be reduced to roughly 18 mm in diameter by using a printed circuit board (PCB), while the battery is limited to roughly a 20 mm diameter to contain enough capacity for system operation. Strategies related to ongoing packaging designs will be discussed below.

Validation of Integrated System

Disclosed herein is an electrochemical characterization of the fabricated DO sensor and the fully integrated bPod platform in several testing environments. The electrochemical characterization of the bPod was performed in three separate stages: (1) characterization of the DO sensors in a 250 mL beaker using a benchtop potentiostat, (2) characterization of the fully assembled bPod in a 2 L vessel for determining the optimal bPod testing experimental protocol, and (3) testing of the bPod in a 10 L Bioflo310 bioreactor for calibrating and dynamically monitoring the bPod platform at several DO % saturations. Within each testing setup several DO sensor packaging variations were demonstrated to improve the sensor repeatability and response time. In the following sections, the specifications for each testing setup will be explained and applied to validate system components for the bPod.

Figure 33:
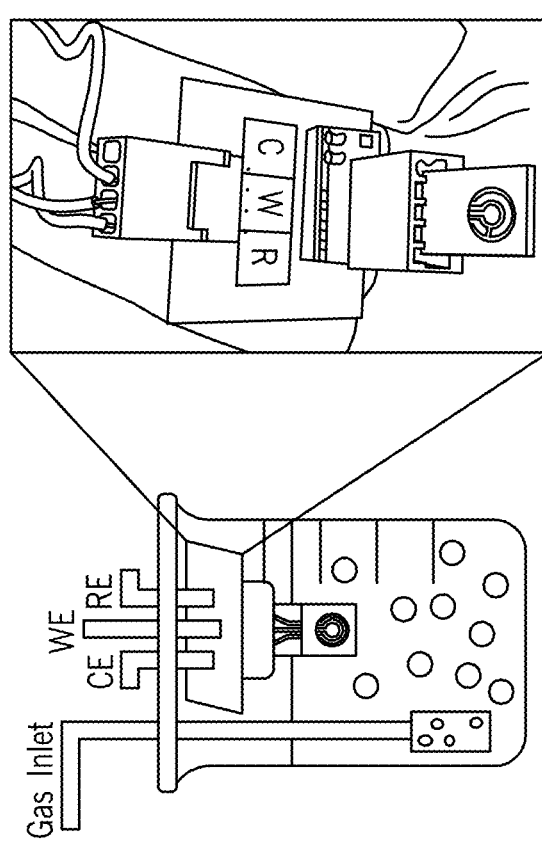
FIG. 33 shows an experimental setup used for determining the excitation bias for the reduction of DO.

Electrochemical Characterization—Beaker-Level Characterization of Electrochemical DO Sensor A small-scale beaker-level setup was developed for evaluation of the DO sensor prior to integration with the bPod platform. As shown in FIG. 33, the setup incorporates a gas inlet for pumping air or N2 into the beaker, a wired adapter for interfacing the sensor with the benchtop potentiostat, a flask holder for fixing the adapter in place, and a parafilm cover for trapping air inside the beaker. Sensors were submerged in 125 mL of 0.1 M KCl solution for electrochemical measurements, performed with a benchtop potentiostat (BioLogic VSP-300). A single gas line, carrying either air or N2, was connected to the beaker with polyethylene tubing (¼" ID) and a stone bubble diffuser. The diffuser produces small gas bubbles, allowing facile gas dissolution by increasing the gas-solution interface, and leading to a rapid achievement of a partial pressure equilibrium. An external nitrogen tank (K-bottle) was connected to sparge (bubbling of a gas) $N_2$ into the beaker, displacing DO molecules within the solution, thereby creating a 0% DO saturation state. To return the solution back to an ambient oxygen condition, such as air (~20% $O_2$), the tubing was connected to an electronic serological pipette aid (USA Scientific, Ocala, FL), and air was pumped into the vessel via the accompanying air compressor. The parafilm cover was placed over top of the beaker to prevent gas exchange with the surroundings. By removing the parafilm cover the system would return to an ambient equilibrium after 10-15 minutes.

Custom Adapter for Beaker-Level Testing

Sensors were interfaced with the potentiostat via a custom adapter. The adapter utilizes the CEC and a 3D-printed spacer discussed herein to form an electrical contact with the sensors terminated with three wires. As seen in FIG. 33, the adapter has two 2.54 mm pitch female headers soldered to a Veroboard (perforated FR4 board) which the CEC is plugged into. Traces on the backside of the board are soldered to a 4-pin 90° Molex connector, and the three wires are fastened with crimps inside the sockets. The wires connected with the potentiostat via alligator clips corresponding to the working, counter, and references electrodes.

Determination of Excitation Bias Point

The custom fabricated electrochemical DO sensors were evaluated using the beaker-level setup to determine a suitable excitation bias voltage which would maximize the DO reduction peak (maximally negative current). The sensor current response was recorded using a benchtop potentiostat (BioLogic), and the electrochemical properties of the three-electrode system (WE: Au, CE: Au, RE: Ag) in 0.1 M KCl were analyzed at two distinct DO % saturation states, namely a N2 purged state (0% DO) and an air purged or ambient state (denoted as 100% DO). As discussed herein, the dynamic range of DO sensors are defined by the signal difference between a 0 and 100 DO % saturation states. Common methods for controlling DO % saturation levels include pumping out (flowing N2 gas into the system), or by adding an oxygen scavenger (i.e. sodium sulfite). The pump-out method was utilized in this work to better relate to the bioreactor agitation conditions and to observe the effects of purging on the sensor response. Purging was disabled during measurements to minimize the effects of aeration and agitation on the bare electrodes.

Figure 34A:
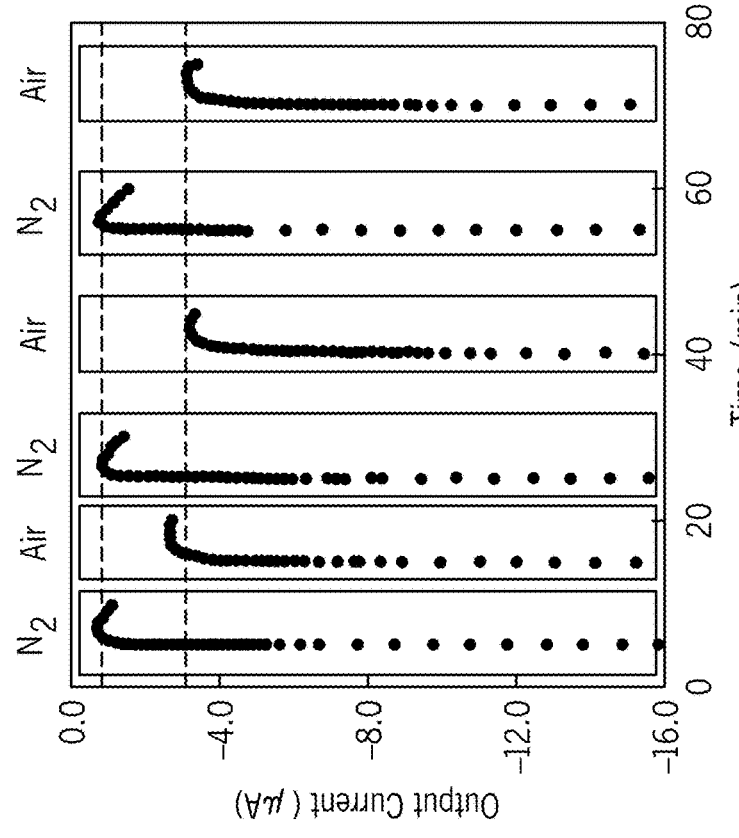
FIG. 34A shows a cyclic voltammogram acquired from DO sensor in 0.1 M KCl purged at two different DO % saturation states, 0% (N2) and 100% (air).
Figure 34B:
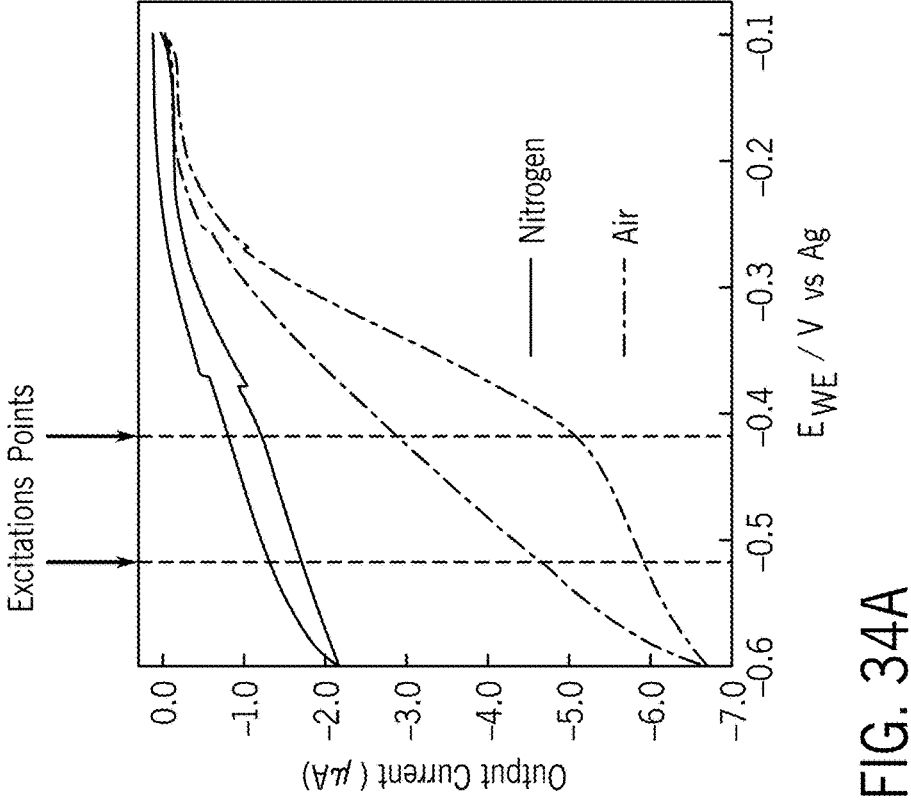
FIG. 34B shows a chronoamperogram of 0% and 100% DO saturation states using an excitation bias of −0.42 V.

Two electrochemistry techniques were employed to characterize the electrodes: cyclic voltammetry (CV) was used to determine the optimal voltage bias which was utilized in chronoamperometry (CA) for sensor calibration. FIG. 34A presents the resulting cyclic voltammogram of the bare electrode at both N2 and air purged states. The limiting current representing the reduction of DO was observed between −0.4--0.6 V, corresponding to the DO concentration. This is reflected as an output current ranging from 2--5 µA between the 0 and 100% DO saturation states. As the potential became increasingly negative, hydrogen adsorption was observed at −0.72 V, therefore values beyond this point were discarded. From this, two candidate voltage biases were identified for application during CA measurement, namely −0.42 V and −0.5 V. These values corresponded to the excitation bias points that could be generated using the proposed potentiostat IC, namely the LMP91000. CA was applied as a fixed excitation bias pulse of −0.42 V, held for 45 seconds across the WE and RE, while the current was monitored between the CE and WE. The resulting chronoamperogram is shown in FIG. 34B. The DO % saturation state alternated between 0 and 100% at both 5-minute (first three) and 10-minute (last three) intervals, which resulted in an easily distinguishable separation between 0 and 100% DO saturation. This experiment verifies the viability of the electrochemical DO sensor materials and topology for bioprocess monitoring applications, as well as creates a reference system that can used to configure the AFE (LMP91000).

DO Sensor Testing with FEP Membrane

Following the electrochemical characterization of the bare Au DO sensors, electrodes were covered with an FEP membrane to form an isolated electrolyte well. The tape-based sensor interface, as described herein, was utilized for characterizing the current response of the sensor with and without the FEP membrane in 0.1 M KCl. This sensor interface provides a roughly 100 µm (thickness of electroplating tape) distance between the FEP membrane and WE surface, increasing the diffusivity of DO through the inner electrolyte, w improving the sensor response time. Since the DO within the bulk solution diffuses through the FEP membrane for the electrolyte reservoir to reach a steady state equilibrium, a delay in the response time for the sensor can be expected when compared to the bare Au electrode.

Figure 35:
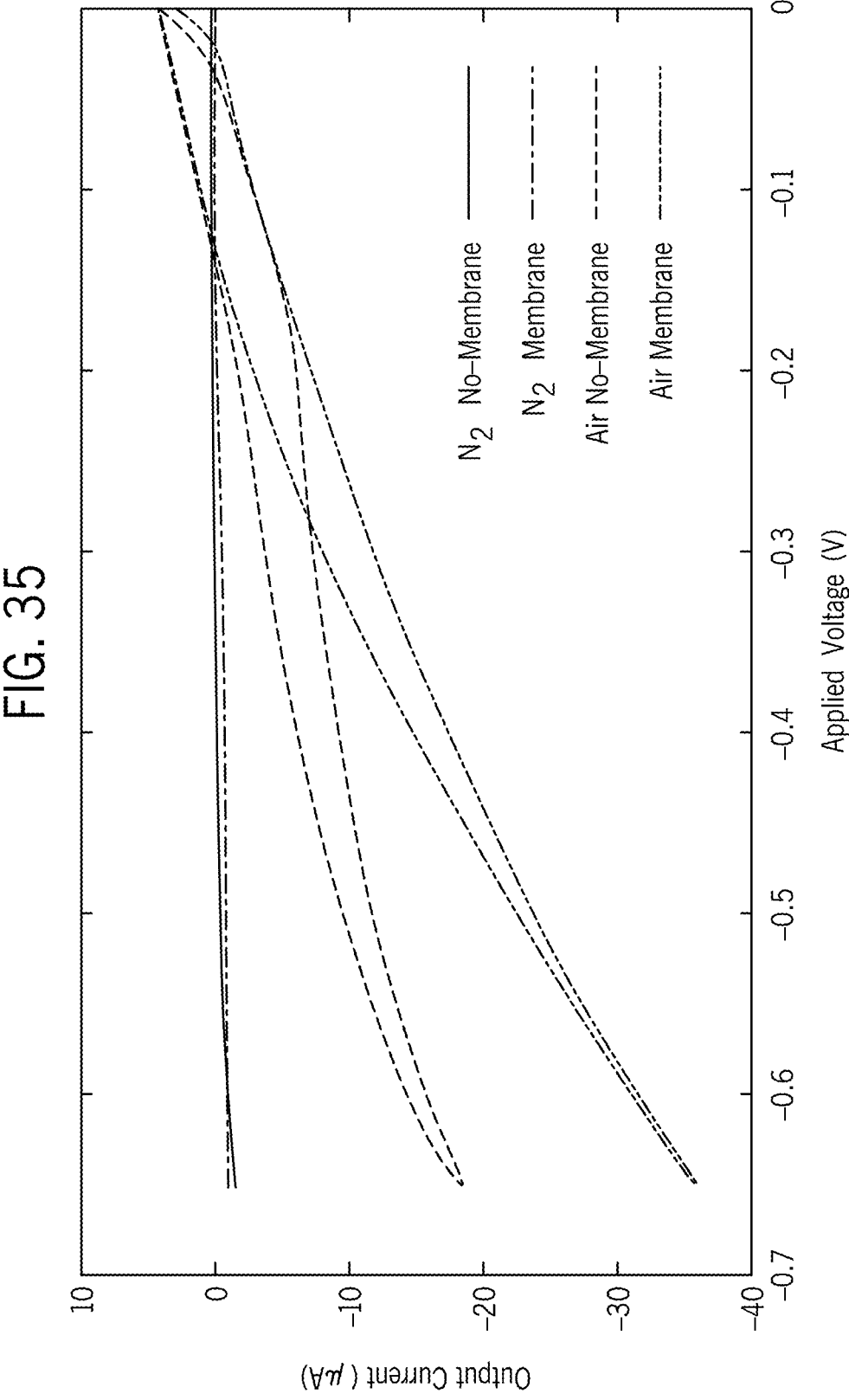
FIG. 35 shows cyclic voltammograms comparing peak current response between a bare sensor and a membrane integrated sensor in 0.1 M KCl at air purged and N2 purged DO % saturation states.

The beaker-level setup was used to compare the current response of the tape-based sensor interface to a bare Au sensor at two saturated DO states, an N2 purged state and an air purged state. N2 was sparged into the beaker for 3 minutes to generate a 0% DO saturation state, which was followed by sparging of air for 3 minutes to achieve a 100% DO state. The cyclic voltammogram in FIG. 35 presents highlights the differences between the diffusion limiting current necessary for both sensor configurations. The CV was performed with a linear sweep from 0.0--0.65 to preserve the sensor integrity as the potential became increasingly negative. Most notably, the current response when comparing the bare Au sensor and the tape-based sensor interface (FEP membrane) was similar at the N2 purged state, about 1 µA at −0.5 V, whereas a large deviation was seen in the current response during the air purged state between the FEP membrane sensor (−15 µA) and the bare sensor (−25 µA) in 0.1 M KCl. This result indicates that, under identical sparging idle times, the tape-based sealed sensor fully saturated at a lower excitation potential due to the diffusivity of the attached FEP membrane.

Figure 36:
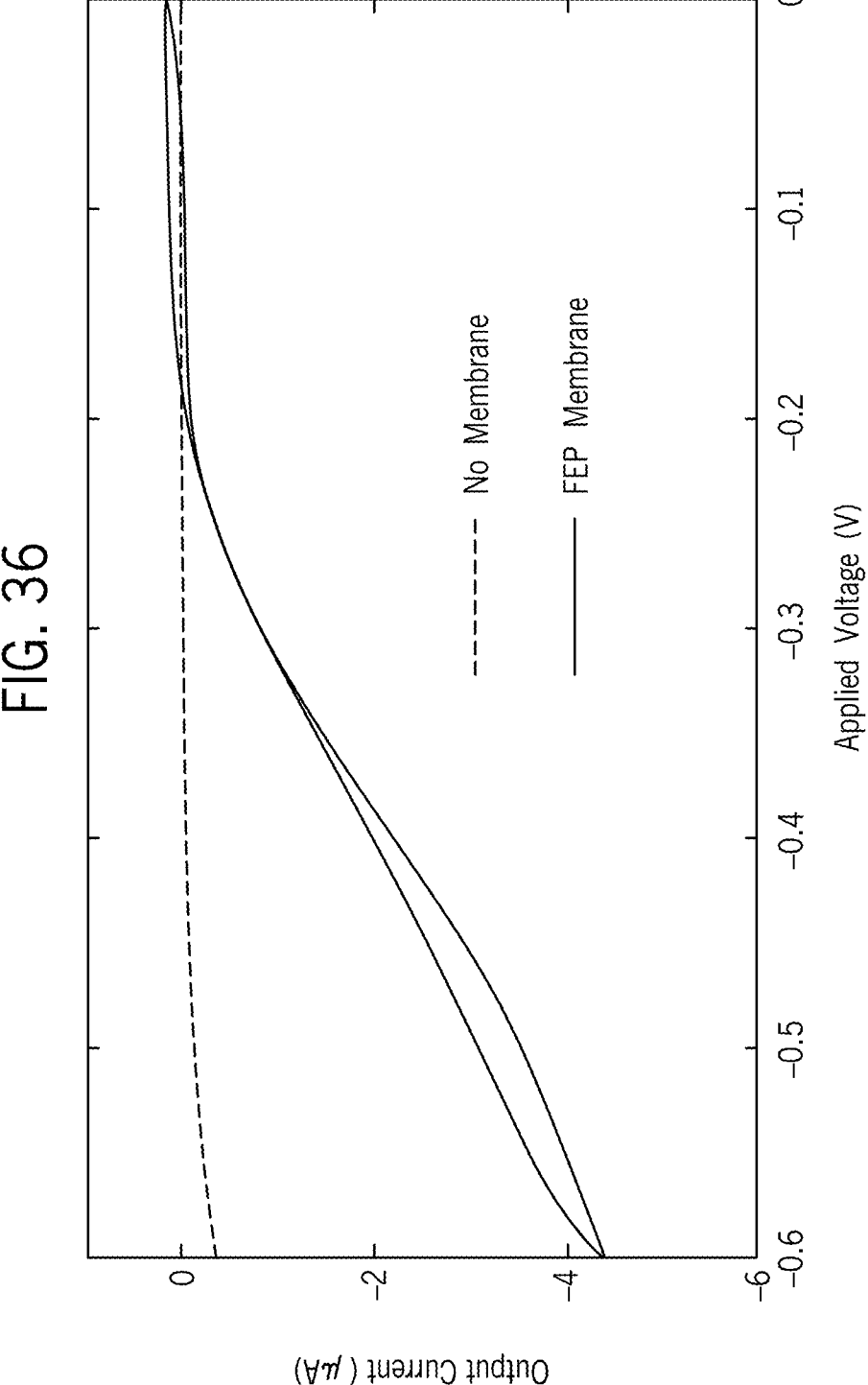
FIG. 36 shows cyclic voltammograms of a bare sensor and a membrane integrated sensor in DI water at an air purged DO % saturation state.

To demonstrate the ability of the FEP membrane electrode to perform in a non-conductive media, the bare Au electrodes and the tape-based sensor interface were tested in DI water. With an identical experimental setup, the sweep parameters were adjusted to 0.0 V to −0.6 V, and the water was purged solely with air for 10 minutes (given that the N2 purged state was the same for both sensors). It is shown in FIG. 36 that the bare sensor is unable to measure DO in the absence of an electrolyte (KCl), which provides ions which enhance electron transport to the sensors. Conversely, the FEP membrane enabled the DO sensor to successfully measure DO by diffusion through the electrolyte cell. When testing bare electrodes, bubbles from the sparging may displace fluid from the electrode surface and cause sporadic spikes in the current response, therefore the gas sources were turned off momentarily during electrochemical DO measurements. This behavior was not observed in electrodes covered with an FEP membrane, therefore measurements and sparging could be performed simultaneously, providing dynamic monitoring capabilities which are compatible with existing bioreactor systems. This implies that the bPod would be able to monitor culture parameters under continuous agitation and aeration conditions, which are necessary for the proliferation of the cell culture within the bioreactor.

Beaker-Level Measurements with LMP91000

Figure 37:
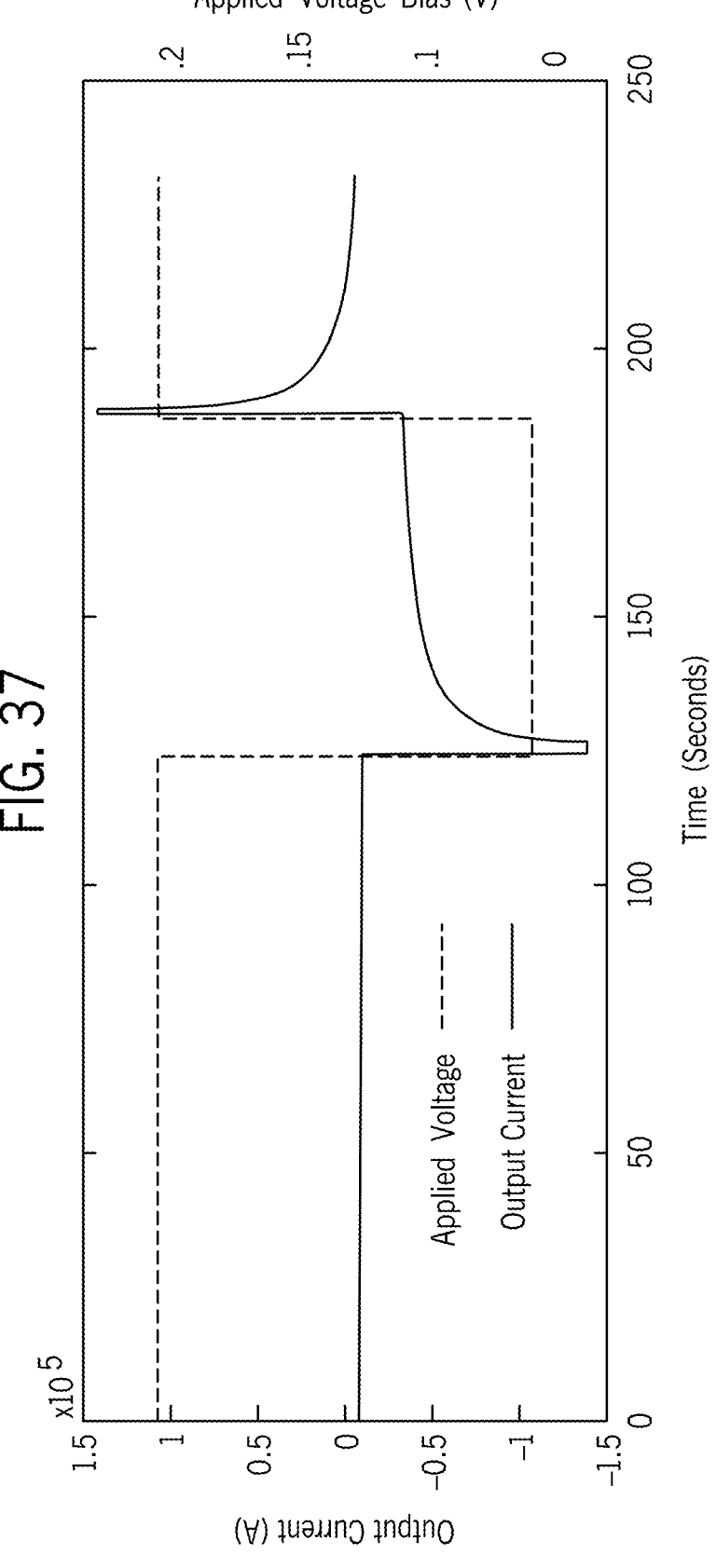
FIG. 37 shows a chronoamperogram of gold electrode with LMP91000 excitation bias between 0 and +0.2 V in 1 mM $K_4Fe(CN)_6$ in DI water.

The benchtop potentiostat was operated as a gold standard reference for electrochemical characterization of the DO sensors and assisted with transitioning to the AFE module (LMP91000). The small form factor of the LMP91000 allowed for portable amperometric measurements. The operation of the AFE however presented two challenges: (1) a limited resolution for applying excitation biases and (2) incompatibility with performing CV measurements. However, utilizing the excitation bias determined from the benchtop potentiostat, CA measurements were possible for the LMP91000 and the electronic module. Therefore, an experiment was conducted using the bare electrode sensors to verify proper sensor conditioning and monitoring capabilities of the LMP91000. The electrodes were submerged in 1 mM potassium ferrocyanide ($K_4Fe(CN)_6$) in DI water, a common compound for characterizing electrochemical sensors, and the current response was monitored for several voltage biases applied by the LMP91000. The LMP91000 potentiostat was programmed to apply a +0.2V pulse for 120 seconds ($K_4Fe(CN)_6$ oxidation potential vs. silver reference electrode). FIG. 37 shows results of a chronoamperogram of gold electrode with LMP91000 excitation bias between 0 and +0.2 V in 1 mM $K_4Fe(CN)_6$ in DI water. The LMP91000 converts the output current to a voltage which is digitized via the ADC from the BGM121. The data is recorded via wired UART communication to the PC. As shown in FIG. 38, a −0.2V pulse is applied for 60 s, resulting in a reduction spike that reaches a steady state value after about 10 seconds, followed by a +0.2 V pulse applied for 40 s, resulting in an oxidation current response. Data was captured by the BGM121 and transmitted via the Universal Asynchronous receiver/transmitter (UART) through a USB port, and recorded as a .csv file on the PC. This result demonstrated control of the LMP91000 registers for modulating the excitation voltage, as well as the monitoring of the output current. The representative chronoamperometric responses were utilized to determine essential parameters (i.e. pulse duration, sampling rate, the output gain, and virtual ground offset) for adjusting the LMP91000 measurement sequences, namely the sensor conditioning and digitization of the output voltage using the BGM121 ADC peripheral.

Evaluation of Electronic Module

Figures 38A, 38B:
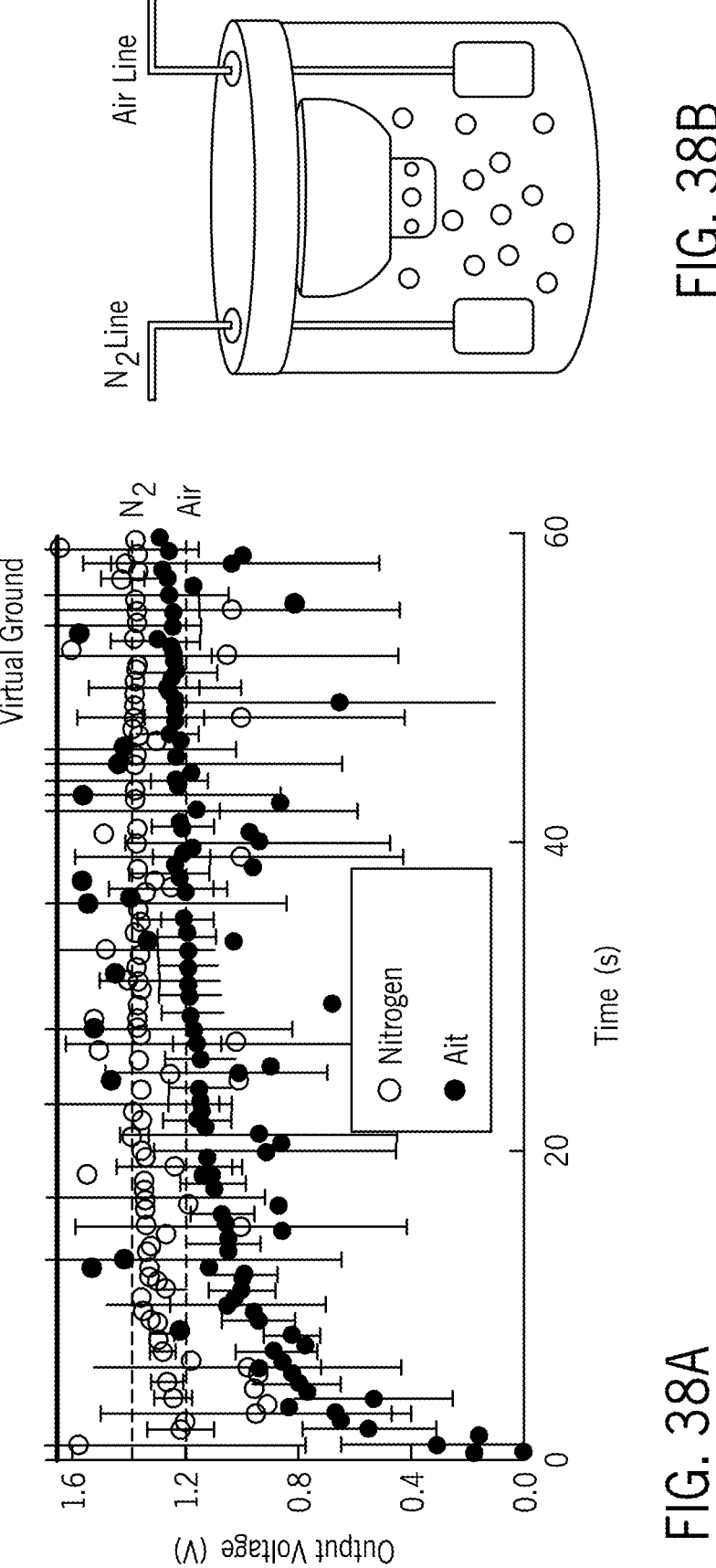
FIG. 38A shows a chronoamperometric measurement of DO in 0.1 M KCl at an excitation bias of −0.5V (N=5).
FIG. 38B shows an experimental setup with N2 and air gas line for testing the electronic module.

Following validation of the LMP91000 AFE module with 1 mM $K_4Fe(CN)_6$ the electronic module was assembled as outlined herein. In order to evaluate the electronic module, for monitoring DO a two point-measurement was performed using the beaker-level testing setup. The DO sensor in this case, however, is used without the FEP membrane attached and the sensor surface was directly exposed to a 0.1 M KCl solution, in order to solely evaluate the operation of the electronic module. Chronoamperometric measurements were performed at 5-minute intervals with an excitation bias of −0.5 V, and the current response was monitored for 1 minute. This current was converted to a voltage reading using the LMP91000 transimpedance amplifier circuit, sent to the ADC of the microcontroller, and then transmitted to the PC using the UART (wired connection). FIG. 38A shows the chronoamperogram at a 0 and a 100 DO % saturation state, obtained by alternating sparging of air and nitrogen, respectively, into the beaker every 5 minutes. The experimental setup with N2 and air gas line for testing the electronic module is shown in FIG. 38B. The observed response time of the sensor was roughly 10 seconds for the air sparge state and 3 seconds for the N2 sparged state, corresponding with direct reduction of DO at the working electrode surface with minimal delay before reaching a steady state response. The scattered distribution of data implies that measurements are susceptible to burst noise, or artifacts as a result of bubbles that collect at the sensor surface, and conversion errors relating to the ADC. It was determined that the BGM121 data transmission was set to a faster sampling rate than the ADC could convert the measured value, however this was resolved for future experiments. The electronic module was able to successfully apply a −0.5 V bias necessary to generate an output current that fits within the adjustable bounds of the LMP91000 AFE (5 µA to 750 µA).

bPod Testing in 2 L Glass Vessel

Two-point calibration in this work refers to a comparison of two separate measurements performed at the determined voltage bias with the same sensor in the bioreactor system: 1) at a 100% DO saturation state and 2) at a 0% DO saturation. This is essential for ensuring repeatability between different sensors, as well as accounting for variations in the bioreactor testing setup. For example, when comparing the benchtop setups, a 200 mL beaker, and a 10 L bioreactor vessel, may produce drastically different max current during two-point calibration, due to the stirring capabilities of the Bioflo310, however this parameter was not compared. Bioreactor system pressure, temperature, agitation and sparging capabilities all contribute to the maximum achievable DO % saturation and the time required between measurements. Three sensor interfaces with varied electrochemical cell geometries were evaluated: the 3D-printed screw-top, the 3D-printed receptacle, and the taped-well packaging architecture. The sensor response and equilibrium time between each specific generation of the bPod will be compared and the aforementioned parameters will be optimized for calibration of the final bPod design.

2 L Glass Vessel Setup

Figure 39:
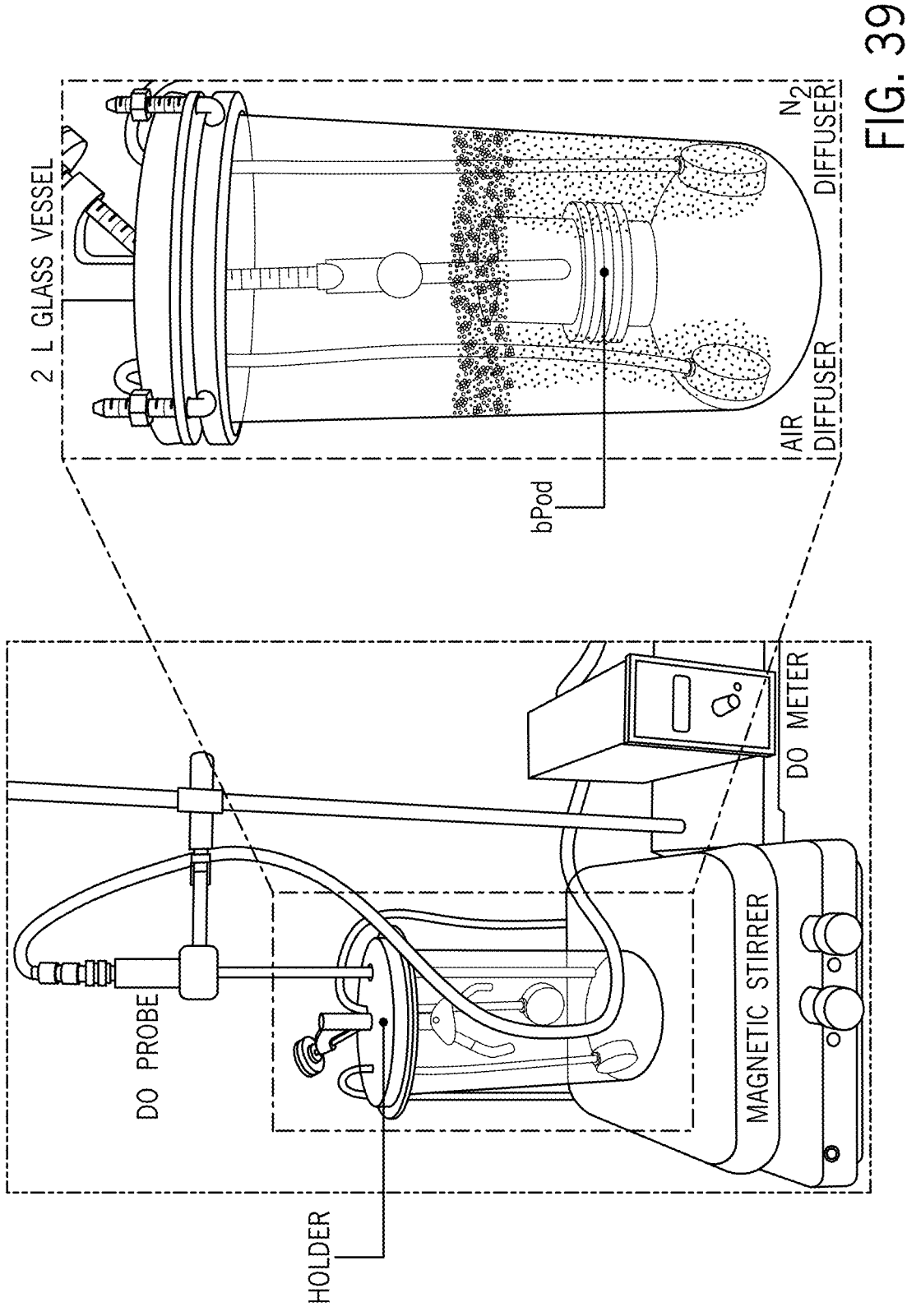
FIG. 39 shows an experimental setup for the 2 L glass vessel.

A 2 L glass vessel set-up was developed to generate a 0 and 100% DO saturation states for performing two-point calibration with the bPod. FIG. 39 provides an overview for the 2 L bioreactor vessel setup. Gas supplies are provided by a nitrogen tank (K-bottle) and a compressed air line (attached to the building). Polyethylene tubing (⅛" ID) connected pressure regulators (5 psi) attached to the gas supplies, through a ⅛"-¼" adapter (McMaster-Carr) to the fine stone bubble diffusers, which connected to ¼" ID polyethylene tubing.

The DO % saturation state is monitored by a commercial inline DO probe (Mettler Toledo) fixed into place by a flask holder and connected via a wire to a DO meter (Ingold), where the DO % value is displayed. The bounds of the DO meter are adjusted via an analog knob, such that both a 0 and 100% DO states are achieved for the given system. The larger vessel provided a dedicated inlet for each gas source and enabled more rapid purging of air into the vessel. This reduced the equilibration time for generating a 100% DO state as compared to the beaker-level set-up. Simultaneous sparging of air and N2 into the 2 L vessel is shown in FIG. 39, with the generation 2 bPod suspended in the solution, however no control of the gas flow rate into the vessel was available.

Figure 40A:
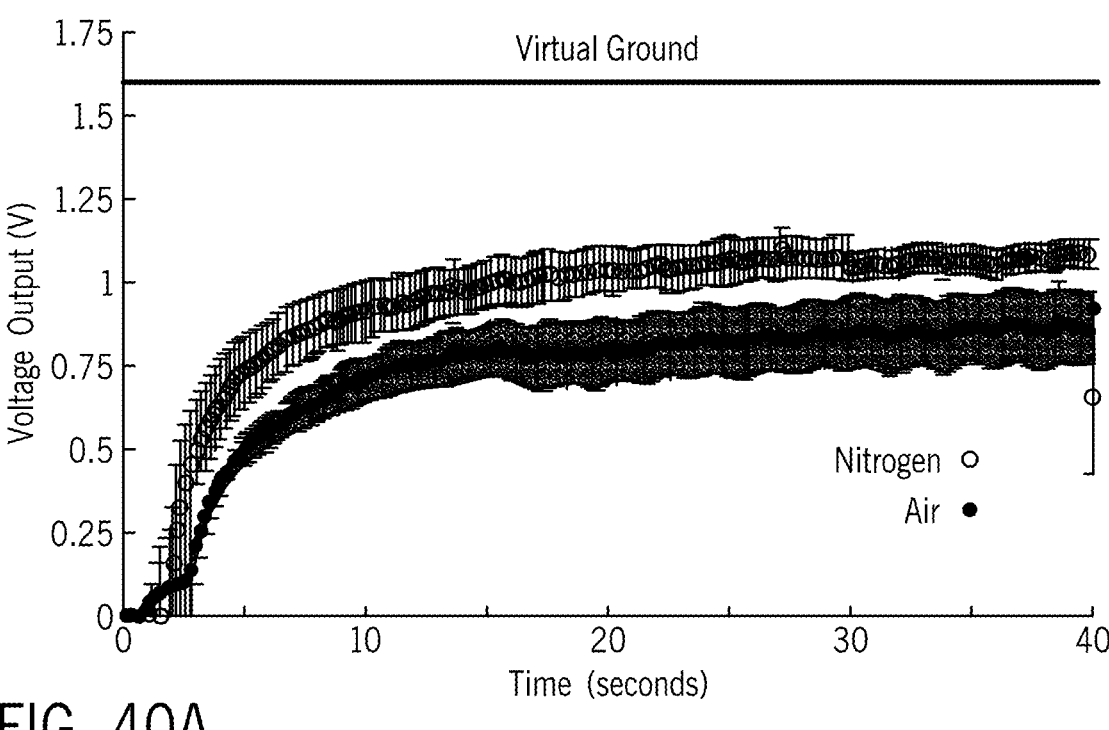
FIG. 40A shows a chronoamperogram of averaged voltage output at two DO % saturation states generated by purging N2 (0% DO) and air (100% DO), respectively, at 10-minute intervals and apply an excitation bias of V=−0.5 V (N=4) for a 40-second measurement.

Two-point calibration is typically conducted using a long purge time (i.e. 15-20 minutes) for DO % saturation values to completely stabilize. The hotplate is placed underneath the 2 L vessel and applies additional agitation to the system by spinning a magnetic stir bar. The formation of bubbles onto the membrane surface of the DO probe and the bPod, causes fluctuation in the DO saturation. The magnetic stir bar assists in the mixing and perturbation of the solution underneath the probe and bPod, ensuring sufficient diffusion of dissolved oxygen through the FEP membrane and stabilization of the steady state probe readings. This arrangement supports chronoamperometric measurements and two-point calibration of the bPod, containing the developed electronic module assembled with the rest of the system components.
Generation 2: 3D-Printed Screw-Top Sensor Interface The two-point calibration of the bPod (generation 2 enclosure) was performed in the 2 L testing setup. Once a stable response was observed then a measurement could be performed with the bPod. The excitation bias determined during benchtop testing is applied to the assembled DO sensors, using the CALIBRATE command (as described herein) at the two DO % saturation states (0 and 100%, respectively). FIG. 40A displays the resulting chrono-amperogram of the two-point calibration with the FEP membrane attached to the screw-top sensor interface, demonstrating successful wireless transmission of data to a custom phone app, and exhibiting smaller variations of the current response due to system agitation than without the FEP membrane. Testing occurred in 0.1 M KCl, with an applied excitation bias of −0.5 V for 40 seconds as opposed to 60 seconds. Longer duration sparging and wait between measurements (5-10 minutes) were added to allow the bulk solution to reach a steady state DO % saturation, as well as for the electrolyte well to equilibrate with the bulk. By reducing the measurement duration and maintaining a distinguishable difference between the equilibrium 0 and 100% DO saturation state, the bPod is able to remain in a low-energy mode for a longer time interval, thus decreasing the power consumption. During CV comparisons between membrane and non-membrane sensors, an increase in the sensor response time was observed. This was attributed to the additional diffusivity of the FEP membrane. The configuration of the bPod enclosure (generation 2), which resulted in the increased sensor response time incorporated the 3D-printed screw-top sensor interface (as described herein).

Figure 40B:
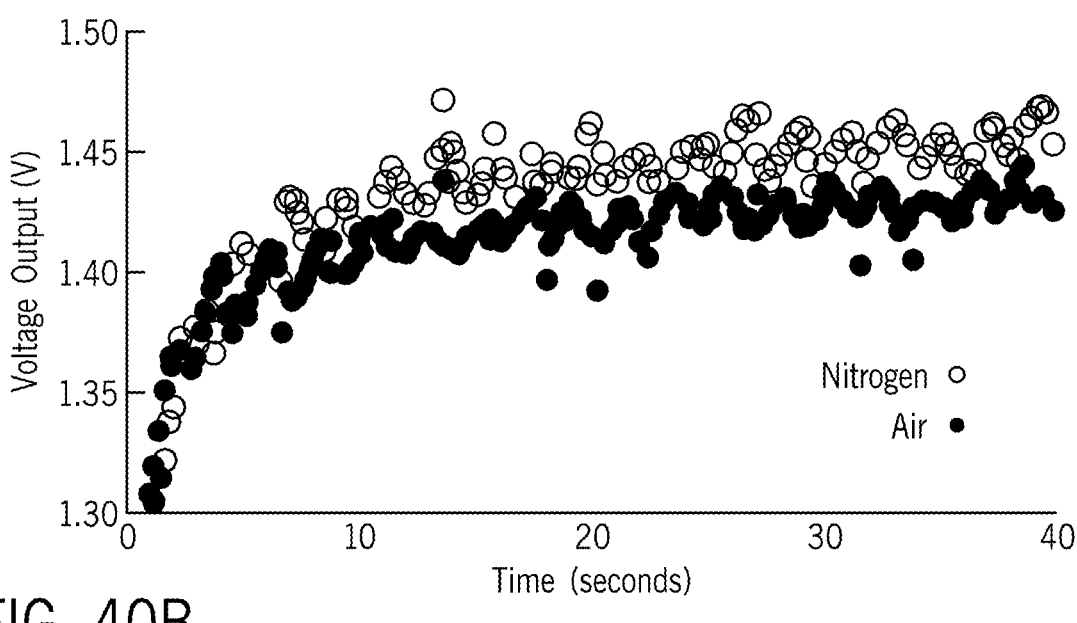
FIG. 40B shows degradation of sensor response that was observed after several days following the same testing conditions.
Figure 41B:
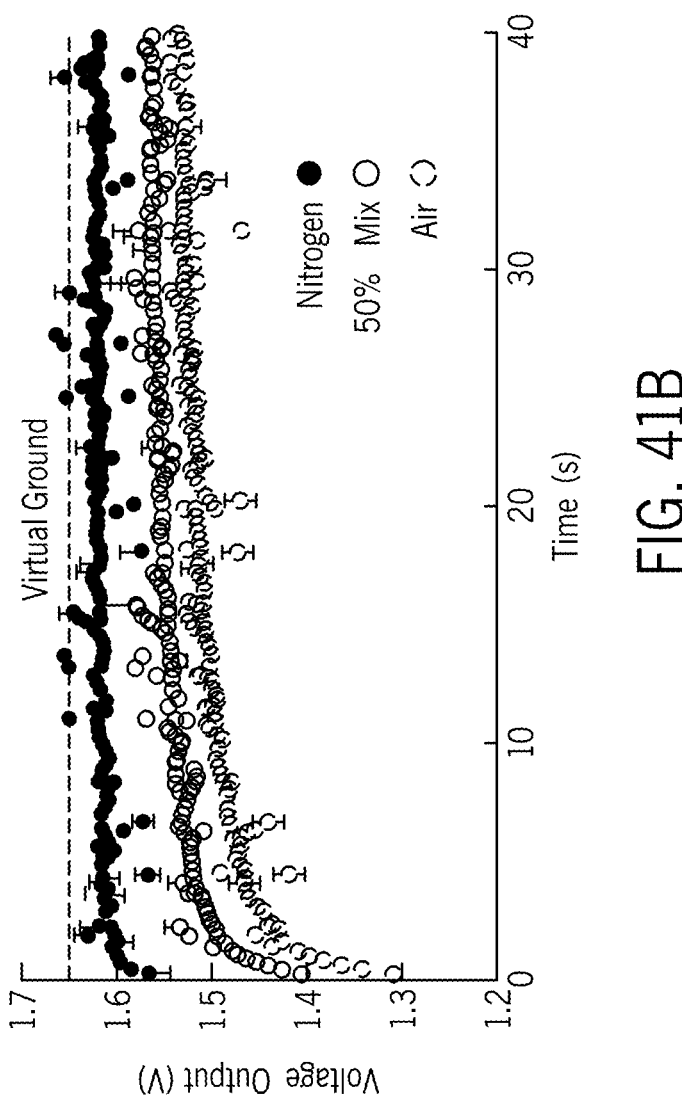
FIG. 41B shows a chronoamperogram of the bPod with the 3D-printed receptacle sensor interface at a −0.5 V excitation bias for several DO % saturation states (0%, 50%, 100%)
Figure 41A:
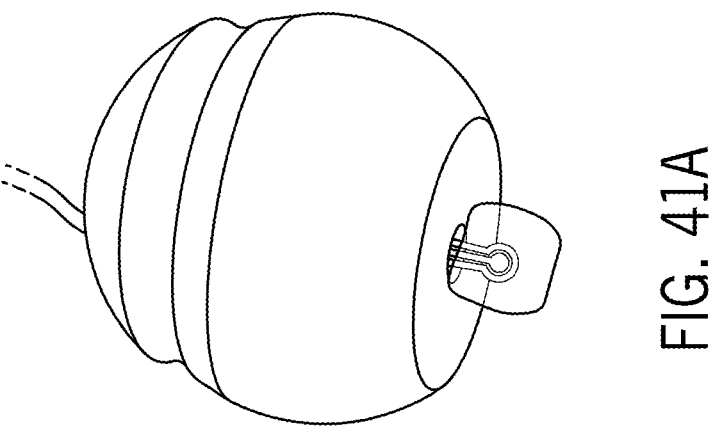
FIG. 41A shows an assembled bPod.

Repeated experiments with the same sensor several days later were performed, resulting in a reduction in the voltage response from 0.75 V to 1.40 Vat 100% DO saturation, as shown in the chronoamperogram presented in FIG. 40B. This behavior originates from instabilities of the Ag/AgCl RE which occur over time as the thin film Ag layer is consumed during reduction in KCl. Inefficiencies with the 3D-printed screw-top sensor interface design, notably the 7 mm distance between the FEP membrane and the electrode surface also contributed to the diminished voltage response and remained unchanged even after 40 minutes of constant sparging at each DO % saturation state.
Generation 3: 3D-Printed Receptacle Addressing concerns with the screw-top sensor interface, the complex generation 2 enclosure was modified, and the 3D-printed receptacle was used instead to form the electrolyte well (described herein). Recall the 3D-printed receptacle was inserted into the enclosure and sealed with epoxy at the intersection of the generation 3 bPod enclosure, as shown in FIG. 41A. The simplified sensor interface allowed the bPod to be placed into the 2 L glass flask and a two-point calibration was performed. In order to obtain the electrochemical characterization throughout the duration of the measurements, a 3.7 V Li—Po battery (GM301014H, PowerStream) was utilized to a power the device, and wireless data acquisition was conducted using the 'CALIBRATE' command of the custom app. Additionally, DO % saturation was monitored once every 5 minutes for three saturation states $N_2$ purged (0%), $O_2$ purged (100%) and a mixture of $O_2$ and $N_2$ (~50%) purge conditions. Slight variations in the values read by the DO meter were observed during simultaneous sparging of both $N_2$ and $O_2$ due to the proximity of the $O_2$ and $N_2$ diffusers to the DO probe which caused the steady state percentage to fluctuate+/−5%. The integrations of a mass flow controller with the 2 L setup would be necessary to correct this behavior.

Figure 42B:
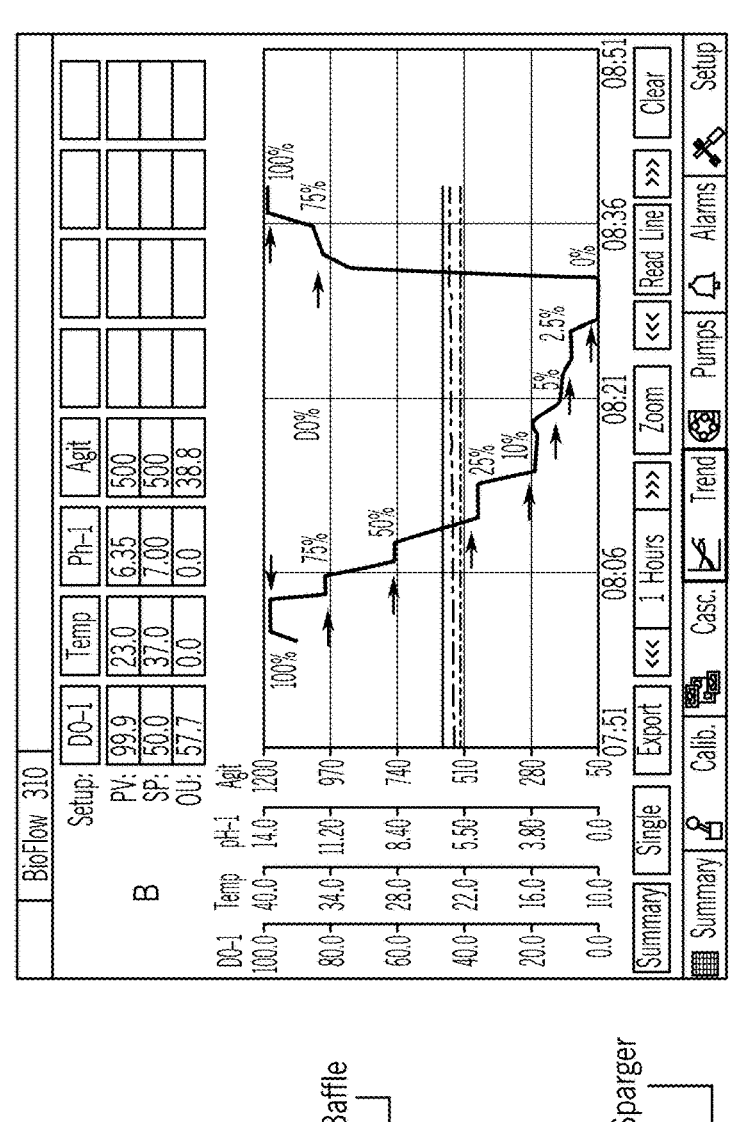
FIG. 42B shows a screenshot of the characterization of the DO % saturation profile produced by the Bioflo310 fermenter.
Figure 42A:
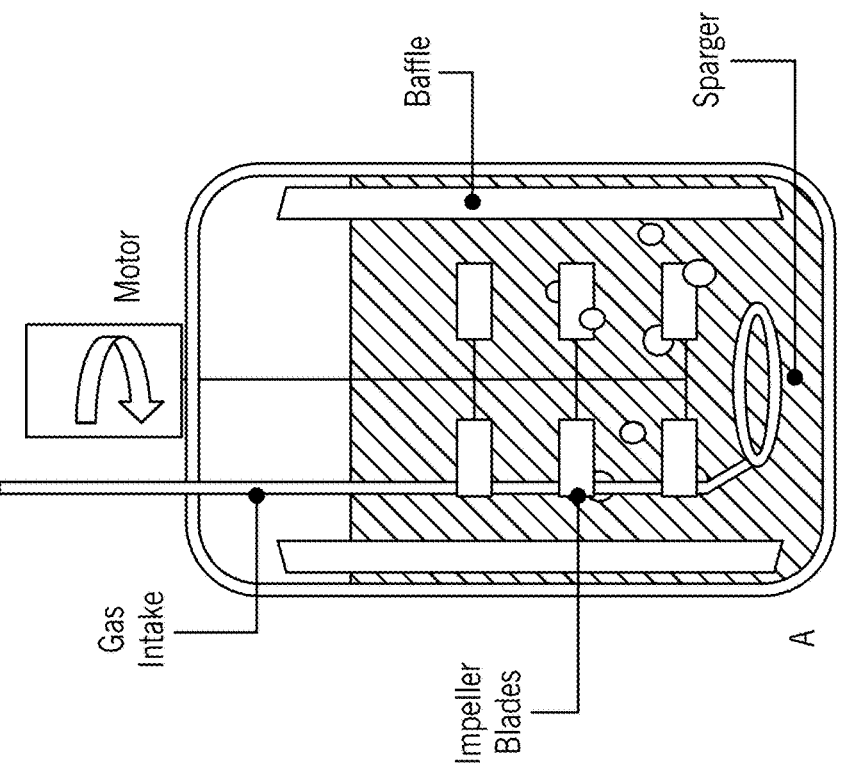
FIG. 42A shows a description of 10 L bioreactor vessel components.

For testing with the 3D-printed receptacle the compressed air line (building) was replaced with a regulated oxygen tank (K-tank). FIG. 41B presents the chronoamperogram of the bPod with the 3D-printed receptacle sensor interface at a −0.5 V excitation bias for several DO % saturation states (0%, 50%, 100%), providing a remarkable decrease of the sensor response time and minimum deviation of the repeated values. By reducing the distance between the membrane and the electrode surface from 7 mm to 500 µm the electrolyte well was able to quickly achieve a steady state DO % saturation. The 3D-printed receptacle starting to exhibit steady state behavior within 4 seconds as compared to 10 seconds when using the screw-top sensor interface. Additionally, using the 2 L bioreactor setup, testing parameters pertinent for tuning of the electronic module, such as measurement duration, equilibration time, response time, sampling rate, and output gain were adjusted to improve system accuracy. A noted downside of this implementation is that though excellent monitoring capabilities were possible the reliability of the sensor assembly warranted further adjustments to the sensor interface prior to scaling to the 10 L bioreactor. It was found that delicate epoxy seals resulted in an inconsistent sensor assembly with low yield and reduced the sensor lifetime (1 or 2 days) as portions of the electrode surface areas were covered while forming the well, as described herein.
bPod Testing in 10 L Bioreactor
10 L Bioreactor Set-Up A 10 L glass bioreactor vessel coupled with the Bioflo310 fermenter (Eppendorf), was utilized for generating a calibration curve for the bPod. In addition, this equipment provides a viable testbed for analyzing the continuous monitoring capabilities of the bPod under a variety of system conditions for long-term bioprocess monitoring applications. As shown in FIG. 42A, the 10 L bioreactor vessel is equipped with two Rushton blade impellers for agitating the solution, a motor column for driving the circulation of the impellers, a single gas inlet connected to a sparger at the bottom of the vessel for bubbling in gas mixtures, baffles for assisting with bioreactor mixing, a water cooled/heated metal jacket to stabilize the temperature of the vessel, and several sensor ports for a DO probe, a pH sensor as well as a temperature sensor. The bioreactor components described above are controlled by an accompanying Bioflo310 fermenter, which is capable of producing a variety of DO % saturations via a built-in mass flow controller, as well as monitoring the DO % saturation using the DO probe for the duration of a bioreactor process.

A single gas inlet is utilized for purging a mixture of air, $N_2$ and $O_2$ into the vessel. High pressure polyurethane tubing (5/32" ID, ¼" OD, MSC Industrial Supply, Melville, NY) is attached to three regulated gas sources: a pure nitrogen tank (AirGas, Radnor, PA), a pure oxygen tank (K-bottle), and a compressed air line (supplied from lab bench), enabling highly controllable gas mixture concentrations to be purged into the 10 L vessel. Gas pressure for each of the three inputs is limited to less than 10 psi, and the overall gas flow rate (L/min) of the fermenter can be specified via the control interface. It is important to note that the Bioflo310 does not internally mix the gases prior to release, instead the gas flow into the vessel is demultiplexed and output as a periodic pulse, dependent on a defined duty cycle. For example, a flow ratio ($O_2$:$N_2$) of 50% $O_2$ and 50% $N_2$ (50:50) for a one second pulse will result in 0.5 seconds of $O_2$ and 0.5 seconds of $N_2$ gas, respectively, to be purged into the vessel at a defined max flow rate.

The DO % saturation state is monitored using a commercial inline DO probe (30 mm) fixed to an access port on top of the vessel and displayed in real-time onto the integrated touchscreen user interface—values are saved once every 30 seconds. Values are calibrated through the user interface and set manually following purging of the system with either 100:0 of $O_2$ (or air), the 100% DO saturation bound, followed by 0:100 $N_2$, the 0% DO saturation bound. Once calibrated intermediate DO % saturation states are achieved through modulation of the $N_2$, $O_2$, and air ratio. As shown in FIG. 42B a descending cascade of DO % saturation equilibrium states beginning at 100% DO and ending at 0% DO is achieved for characterization of the commercial DO probe. It is this DO % saturation reference which shall be used for experiments performed with this setup.

The Bioflo310 fermenter is operated in three-gas-mode which enables mixing of oxygen, nitrogen, and air, while also fixing the impeller blade rotation to a constant rpm. For the following experiments, compressed air was not used, however, future integration into the Bioflo310 is expected to allow for long-term gas purging of the bioreactor (more than 10 days), given the limited supply of the $O_2$ and $N_2$ gas tanks. Additional operation modes allow for long-term bioprocess monitoring defined by system cascades that modulate the agitation of the system, by either increasing or decreasing the rpm of the impeller blades, to maintain culture parameter values, such as DO % saturation, at different stages of cell growth. The 10 L bioreactor setup and Bioflo310 fermenter have been used to evaluate the viability of the bPod prototype under a variety of test condition, and provide an invaluable testbed for further investigation onto the viability of the platform for large-scale bioprocess monitoring applications.

Generation 3: Tape-Based Sensor Interface

To calibrate the bPod inside the 10 L bioreactor vessel the tape-based sensor interface design was integrated with the bPod as described herein, trapping the 0.1 M KCl electrolyte between the FEP membrane and the gold electrode. The bPod was submerged inside the bioreactor utilizing a braided two-wire tether to (1) provide a 3.3 V voltage supply (Agilent, Santa Clara, CA) for prolonged measurements and (2) to prevent the device from colliding with the rotating impeller blades. Prior to measurements, the Bioflo310 fermenter gas ratio was set to start with a two-point calibration of 0% and 100% DO between 100:0 and 0:100 at a 25% interval generating several DO saturation percentages using the built-in mass flow controller (2 L/min flow rate) with a fixed spin speed of 75 rpm. Table 4-1 summarizes the $O_2$ and $N_2$ ratios input in the flow controller and the generated DO % saturation states as correlated with the commercial inline DO probe. The DO sensor was excited using –0.5 V, and the current response was measured every 5 minutes for 30 seconds at a sampling rate of 50 ms with the 'CALIBRATE' state. Data was wirelessly transmitted from the bPod to the external modified smart phone app.

Table 4-1 shows parameters for the generation of DO % saturation states. Constant variables include temperature (22° C.), impeller blade speed (75 rpm), and max flow rate (2.0 L/min).

TABLE 4-1

| $O_2$:$N_2$ (Ratio) | DO %(Probe) |
|---|---|
| 100:0 | 100% |
| 75:25 | 79% |
| 50:50 | 55% |
| 25:75 | 25% |
| 100:0 | 0% |

Figures 43A, 43B:
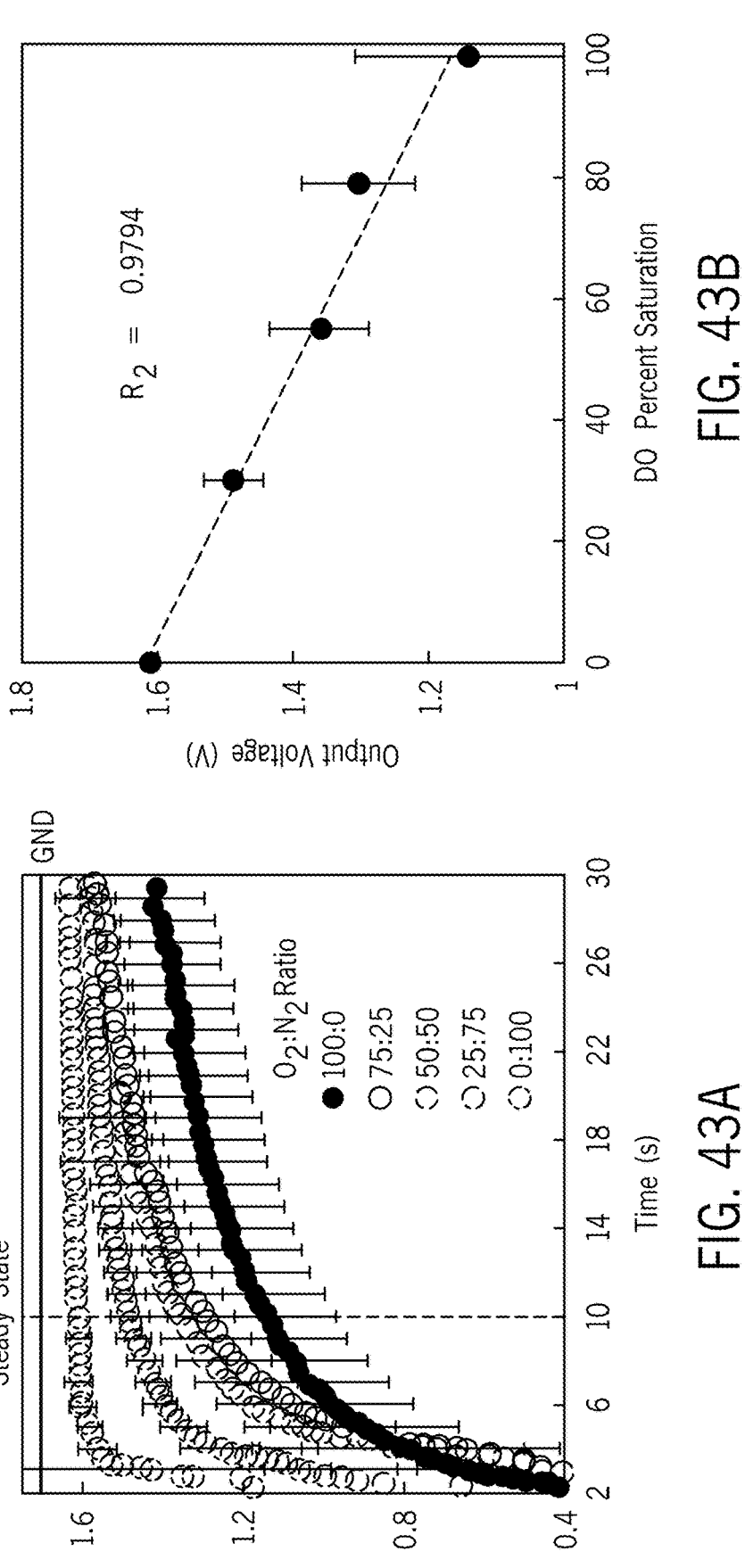
FIG. 43A shows a chronovoltammogram depicting the averaged output voltage recorded by the bPod with 3 repeats at a 5-minute interval (N=3).
FIG. 43B shows a resulting calibration curve taken at steady state (10 sec) and compared to the commercial polarographic DO probe.

FIG. 43A shows the resulting chronoamperograms of the bPod for a decreasing DO saturation state in DI water. A steady state output voltage was observed after 10 seconds at each DO % state, exhibiting a linear behavior in agreement with the polarographic DO probe. The measurement duration of 10 seconds allows the entire current response to be observed, and comparatively to previous measurements (40 seconds) reduces the time the bPod operates in active mode, thus reducing the power consumption. Even shorter measurement durations would allow for further reduction in the power consumption. However, the current response prior to 5 seconds have shown a lack of repeatability across additional sensors.

FIG. 43B provides the resulting calibration curve, correlating DO % saturation to the output voltage at 10 second and exhibiting a linear response (correlation coefficient $R^2$=0.9794) with a sensitivity if 37.5 nA/DO % and limit of detection of 8.26 DO %. Additional testing is necessary to achieve dynamic sampling at various locations for untethered experiments, which would require extrapolation of the current response at lower measurement times (i.e. 5 seconds) that are correlated with the DO steady state behavior.

Industrial bioreactor systems typically utilize an air gas source to generate a calibrated 100% DO saturation state, therefore the dynamic range of the bPod can be readily adjusted to account for this. The resolution is currently limited by the diffusivity of the FEP membrane, the resolution of the LMP91000 TIA, and the stability of the sensor. Each of these parameters can be further optimized to improve the resolution of the bPod by maintaining fixed timed intervals and fermenter settings for each measurement, and systematically adjusting. Nonetheless essential functionality of the 60 mm bPod tethered in the 10 L setup was demonstrated and validation of the system components necessary for scaling the platform was completed.

Real-Time Monitoring of DO with Free-Floating bPod

Figure 44B:
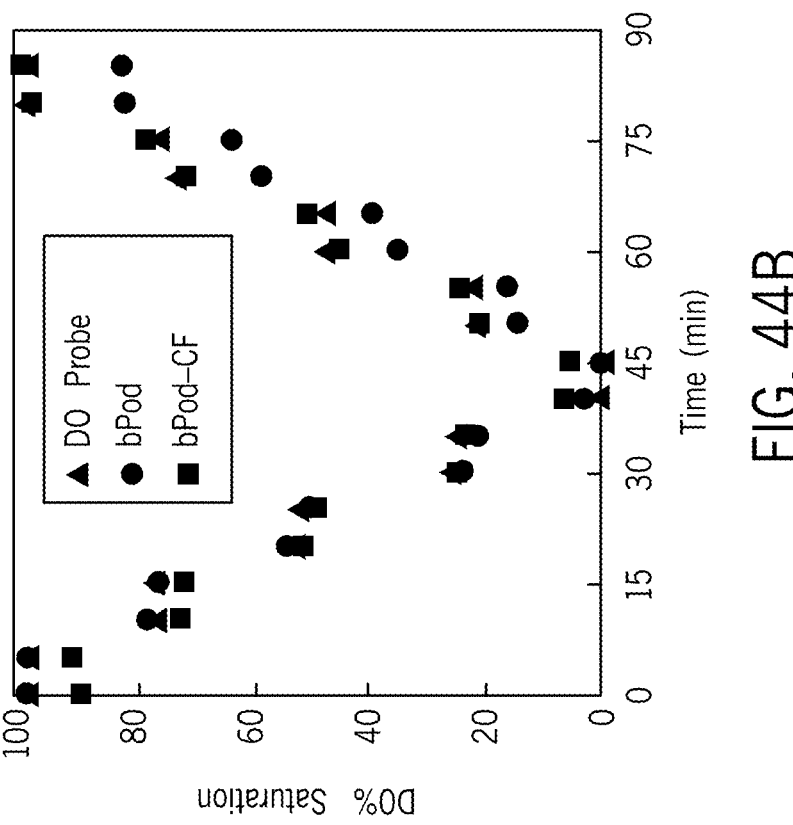
FIG. 44B shows a comparison of the inline DO probe, bPod, and corrected bPod (bPod-CF).
Figure 44A:
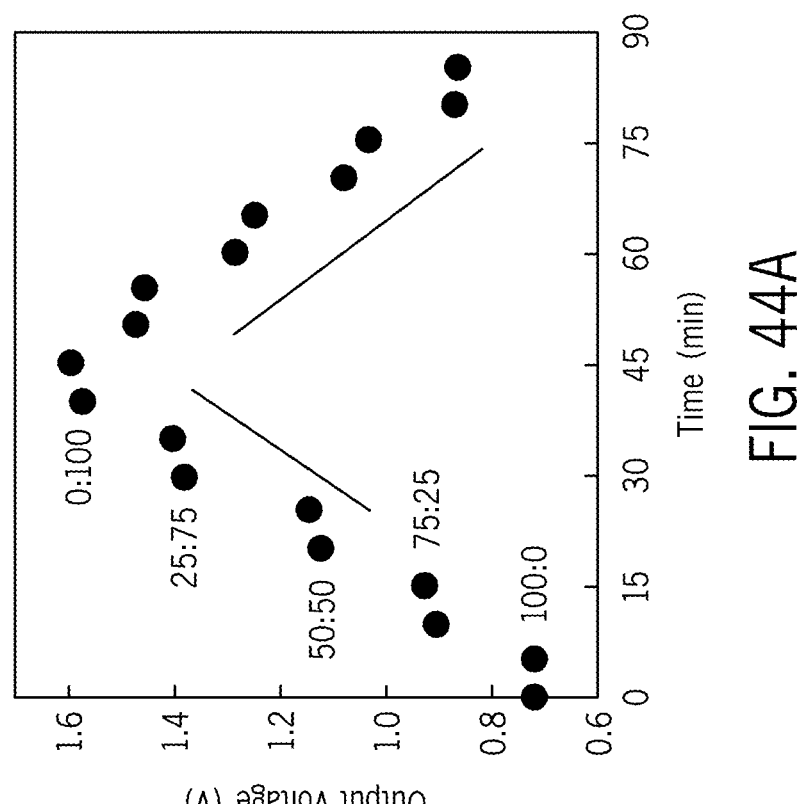
FIG. 44A shows an output voltage from the bPod recorded at steady state (10 s).

To evaluate the stability and continuous monitoring capabilities of the untethered system, the bPod was deployed in the 10 L bioreactor. The 'MEASUREMENT' sequence, as described herein, was utilized to perform chronoamperometric measurements of DO every 5 minutes for 1.5 hours. The DO % saturation was adjusted from 100 to 0% DO at 25% intervals every 10 minutes. FIG. 44A depicts the steady state output voltage response of the bPod taken after 10 seconds. Similar to calibration results shown in FIGS. 43A, 43B, the output voltage was found to linearly increase inversely proportional with DO % saturation, demonstrating excellent reproducibility using the tape-based sensor interface. bPod measurements were converted into a DO % saturation for comparison with the commercial polarographic DO probe to evaluate the system viability in FIG. 44B. Initial measurements varied less than 3% (1 hour), with a slight increase in drift between the bPod measurements (~9%) observed over time. The average shift across the measurements was 4%. A possible explanation for this discrepancy is the degradation of the sensing electrode and shifting of the silver reference due to repeated excitation. Additionally, differences in membrane permeability of the commercial DO probe and FEP membrane used for the bPod may imply measurement intervals longer than 5 minutes are preferable for achieving an equilibrium within the electrolyte reservoir. However, the DO probe and bPod were found to converge slightly with additional sparging time at each particular DO % saturation.

Figure 45:
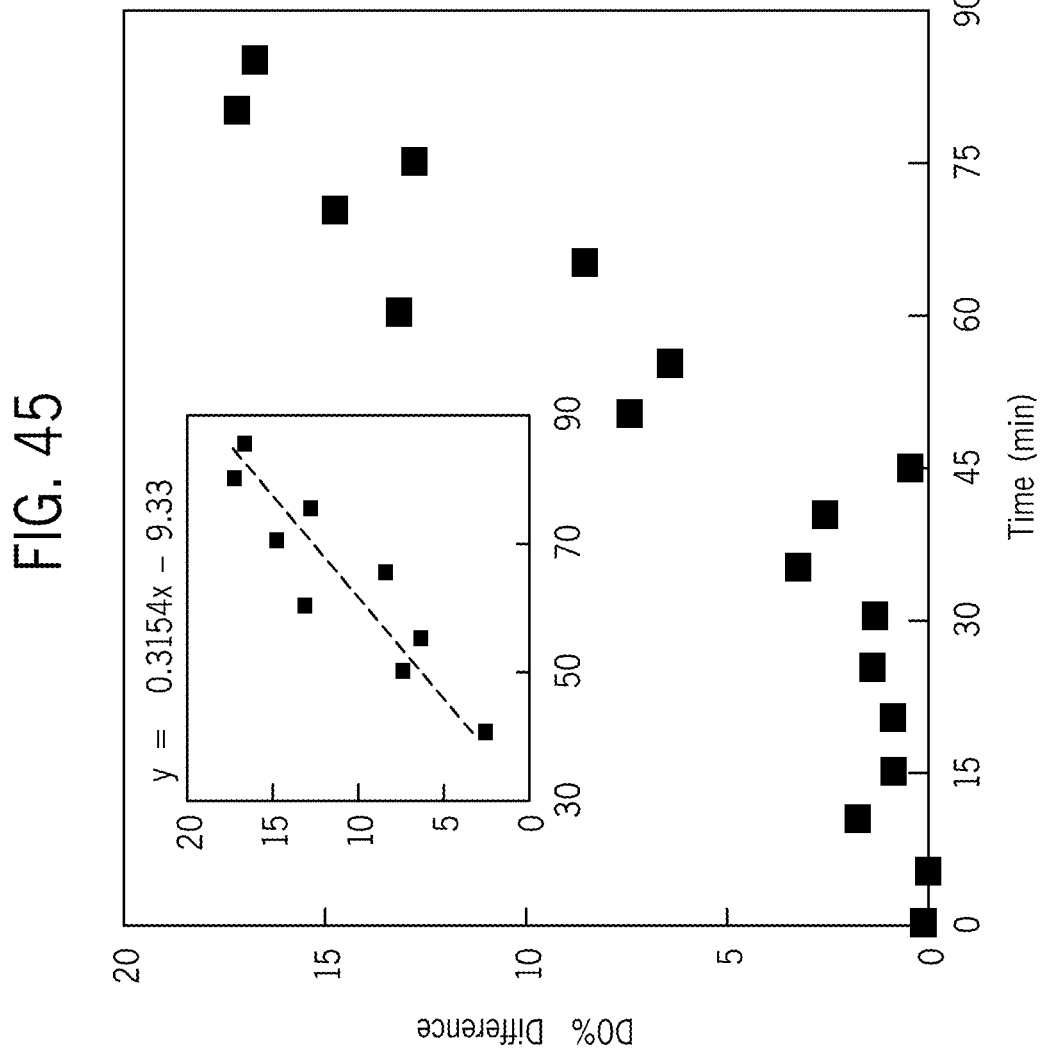
FIG. 45 shows the absolute value of the variation between the bPod and DO probe was extracted over time.

Potential improvements to the bPod sensor response are increasing the ratio between the surface area of the counter and working electrodes (CE:WE>2:1) to minimize the potential difference between CE and WE during measurements, operating a lower excitation potential (−0.42 V), or applying a weighted correction factor based on the rate of sensor degradation. For example, a suggested method to account for the shift in DO % saturation, is to apply a correction factor (CF). As shown in FIG. 45, the absolute value of the difference between the bPod and DO probe DO % were recorded for each measurement, showing a linear deviation for values greater than 5% after 45 minutes. A linear fit was applied and reflected in FIG. 43B, where the modified bPod values with the CF (bPod-CF), show significantly reduced DO % deviation (<4%) across later measurements (after 45 minutes) as compared to the reference inline probe. Therefore, offline correction of linear DO % saturation shifts provide a viable solution to account for degradation in the sensor response, prolonging device operation and stabilizing the DO % saturation measurement of the bPod.

The 3.7 V Li—Po battery maintained a stable supply voltage without degradation throughout the measurement. This sampling time can be extended using a larger capacity battery, such as a typical CR2032 coin cell (Energizer), in order achieve operational lifetimes suitable for mammalian cell culture. While the introduced bPod platform sufficiently validates the practicality of free-floating wireless capsules for DO monitoring within bioreactors, there are additional opportunities to extend this study in terms of device scalability, sensor network size, and continuous monitoring of cell culture products of interest (i.e. monoclonal antibodies). Approaches integrating wireless microsystems with specific and robust sensors can greatly enhance bioprocess monitoring capabilities and provide a platform for investigating product heterogeneity with bioreactors.

Thus an innovative bioprocess monitoring technology, the bPod, has been developed, enabling the real-time wireless monitoring of DO in bioreactors. In completion of this platform, three main system components have been investigated and integrated into a scalable prototype: (1) an electronic module for signal conditioning and wireless data transmission, (2) an electrochemical sensor for the evaluation of DO % saturation, and (3) a leak-proof package to enclose the sensor and electronics for an underwater-environment operation.

The concept improves on existing approaches of microsystems design stemming from ingestible and bioprocessing capsules. However, the choice of wireless modality, sensor assembly, and packaging materials were guided towards future implementation within industrial bioreactors. Initial efforts have focused on characterization of the custom-developed Clark-type electrochemical sensors in both DI water and aqueous ionic media (0.1 M KCl). The electrochemical current response under various excitation biasing was explored for the DO sensor with an integrated FEP membrane. The successful demonstration of the Clark-type electrochemical sensor coupled with a BLE chipset for wireless data acquisition allowed for autonomous measurements controlled by a smartphone or through a computer virtual terminal software (Teraterm). Furthermore, several operation states were programmed to demonstrate scheduled measurements as well as calibration of the bPod. Control of the operational states using a smartphone enabled the bPod to be placed in the lowest energy mode possible when idle, in order to minimize power consumption.

Numerous iterations of the 3D-printed enclosure were explored to eliminate leaking underwater. Early generations of the design demonstrated leak-proof sealing for benchtop testing, however were not sufficient at higher system pressures relevant to bioreactor sparging conditions. Minimizing the design complexity by replacing extraneous O-rings and 3D-printed extrusions from the enclosure in favor of simpler sealing methods, such as epoxy and water-resistant tape, succeeded in achieving a leak-proof condition, formation of an electrochemical well, and allowed streamlined access to the electronic components.

Electrochemical characterization was conducted first using a beaker-level setup before moving into a 10 L bioreactor vessel. For the latter case, the 10 L vessel was attached to the BioFlo310 fermenter, which enabled the generation of various DO % saturation states through the use of a built-in mass flow controller. The DO partial pressure of the system was adjusted by sparging (bubbling) in different ratios of $N_2$, $O_2$, and air, which has been monitored by the bPod. The bPod was calibrated by comparing recorded CA measurements with a commercial inline DO probe (Mettler Toledo). The fundamental behavior of the Clark electrode was verified as the electrochemical characterization of the sensor resulted in a linear current response with respect to the DO % saturation. The integration of the individual system components into a wireless in situ module highlighted the potential of this approach and will provide an invaluable tool for quality control and future optimization of cell cultures within bioreactors.

Device Scaling

In various embodiments the spherically-shaped bPod device is 60 mm in diameter, although in other embodiments the bPod may range between 15-25 mm in diameter to reduce the risk of shear interactions with the cell culture and for easily inserting the bPod into large-scale industrial bioreactor system. Thus, the bPod device is preferably in the range of 15 mm to 100 mm, more preferably in the range of 15 mm to 80 mm, more preferably in the range of 15 mm to 60 mm, and more preferably in the range of 15 mm to 25 mm. Devices having sub-25 mm diameters are most preferred for circumstances in which reduced size is optimal. Devices having larger sizes may be more preferred for environments in which more powerful (i.e., larger) communications components are desired (e.g., larger sized reactors, reactors in which receiving antenna are not able to be positioned close to the reactor, or reactors containing particularly lossy media or other interference). In order to achieve a smaller form factor, each system component is accordingly reshaped or resized. First, by reducing the DO sensor form factor and improving the consistency of the fabrication process, the overall sensor reproducibility will be improved. This would eliminate the need for intermediate interfacing components such as the CEC, which takes up considerable space, and allow permanent interfacing processes such as wire bonding that are ideal for minimizing trace distance. Particularly, smaller feature sizes can be obtained via traditional MEMS fabrication techniques, which are critical for achieving system miniaturization. The current approach presented herein utilizes paper masks produced by laser cutting, which limit the feature size to 100-200 µm and produce irregularities in the deposition trace pattern. Application of photolithography and use of a transparency mask would replace the current fabrication process and allow sub-1 μm features. Finally, a flexible substrate, such as polyimide, will provide additional interfacing options for bending the connecting traces and could be integrated into the 3D-print package, further reducing the form factor.

Figure 46:
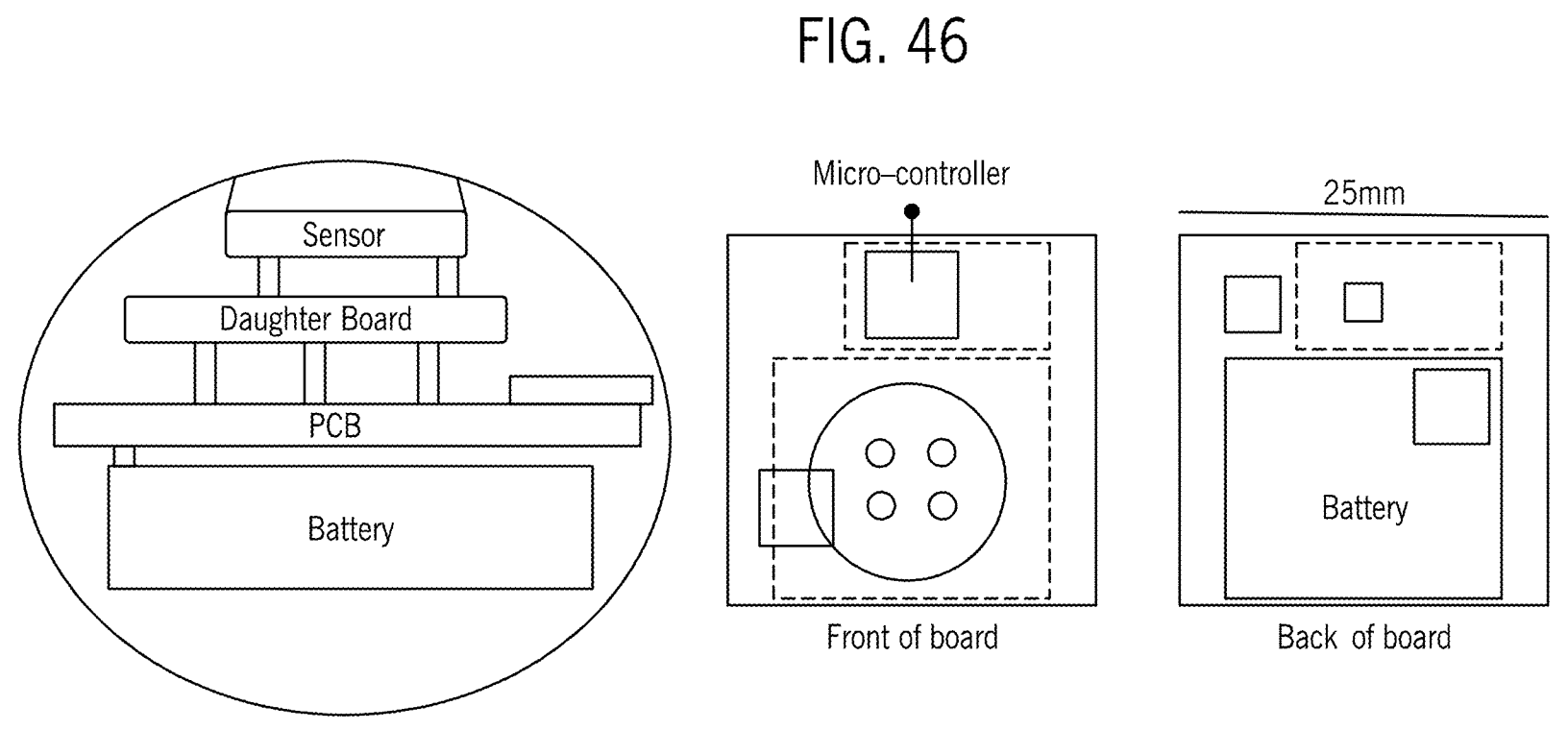

In various embodiments, miniaturization of the electronics module of the bPod will be based on: 1) the design and construction of a custom PCB and 2) implementation of a sufficient power supply. Implementation of a PCB would greatly miniaturize the overall bPod, by replacing the soldered DIP adapters and wires with small copper traces. Sub-25 mm form factor is achievable through various implementations such as a stack board design or proper placement of sensor IC's, as shown in FIG. 46. A major challenge with the design is maintaining a robust RF link between the bPod and external device using BLE communication. Since BLE operates at the 2.45 GHz frequency band it is susceptible to significant power dissipation through a lossy medium, such as water or cell culture. Therefore, careful attention to the antenna placement and ground plane size are needed in order to mitigate potential system losses in signal propagation. Currently, the BGM121 radio board (Silicon Labs), an ideal PCB layout for the BGM121 module, was utilized for the bPod because it incorporated an efficient ground plane design. However, the cost of this was an increase in size; compared to the BGM121 module (6.5 mm×6.5 mm) the radio board was about 5 times larger in length and width. Design and construction of a PCB following best practices for high frequency circuit and antenna design coupled with the rest of the electronics is currently in ongoing development. In certain embodiments a miniaturized PCB will be developed that can be integrated with a variety of electrochemical sensors, and allow for a modular means of simultaneous monitoring not only DO, but temperature and pH.
Location Tracking In addition to monitoring DO % saturation, the bPod can be used to localize culture parameter distribution. In situ modules provide an excellent template for the investigation of location tracking as they are able to dynamically move throughout the flow of the bioreactors. Of particular interest is identifying spatial distributions of process parameters to target product heterogeneities within the bioreactor. Future research focusing on device miniaturization and locating the bPod may utilize deployment of a Bluetooth mesh network that will ensure multihopping of data between distributed sensing devices. A mesh network would considerably improve the security and robustness of the system, providing multiple data transmission paths to overcome failures in device connectivity.

Sensor modalities that require continuous/constant sampling (order of 1 second) or rely on iterative tracking in order to accurately assess the position of the bPod (inertial measurement units i.e. accelerometers) are not ideal for long-term sensing in bioreactors, as they drastically increase the overall power consumption. To this end, incorporation of a low-power tracking methodology leveraging the Bluetooth signal strength (RSSI) in combination with on-board sensors, pressure and magnetometer, would allow for localization of individual nodes independent of previous bPod positioning. A MEMS pressure sensor, such as the LPS33HW (ST Electronics), would provide a small form factor (3.3 mm×3.3 mm×2.9 mm) and monitor depth to up to 4.25 m of liquid. A magneto-resistive sensor, such as the LIS3MDL (ST Electronics) with dimensions: 2.0 mm×2.0 mm×1.0 mm, could also be used to correlate an observed magnetic field to the distance between the sensor and a magnetic source. For more information please refer to the following references. The approaches discussed above provide a means for extracting location data wirelessly out from large-scale stainless-steel bioreactors, which would normally be impossible.

Growing global demand for culture products has led to the increased use of large-scale bioreactors and a shift towards parallel processing. This has necessitated the need for effective tools that both continuously monitor cell culture parameter levels, as well as identify cell culture distribution throughout the bioreactor. This disclosure addresses these needs through the development of an integrated wireless platform for real time monitoring of DO, the bPod that can be integrated into a variety of bioreactor vessels as a low-cost and localizable solution for in situ bioprocess monitoring. Additionally, initial chronoamperometry measurements, resulting in a linear electrochemical response to DO concentrations, show significant progress towards scalable in situ applications targeting bioreactor heterogeneity. Lastly, it is believed that successful integration into bioreactors and further development of innovative autonomous approaches such as this offers highly controllable bioreactor conditions, which will promote large scale production of increasingly complex biologics.

Example 3—bPod Miniaturization

Figure 47:
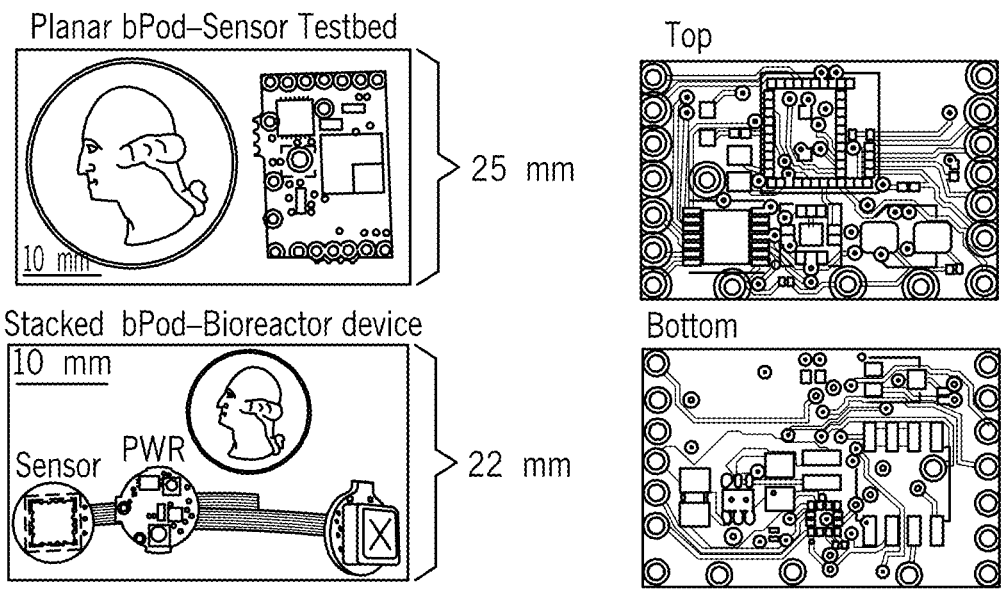
FIG. 47 shows embodiments of bPod electronics modules.
Figure 48:
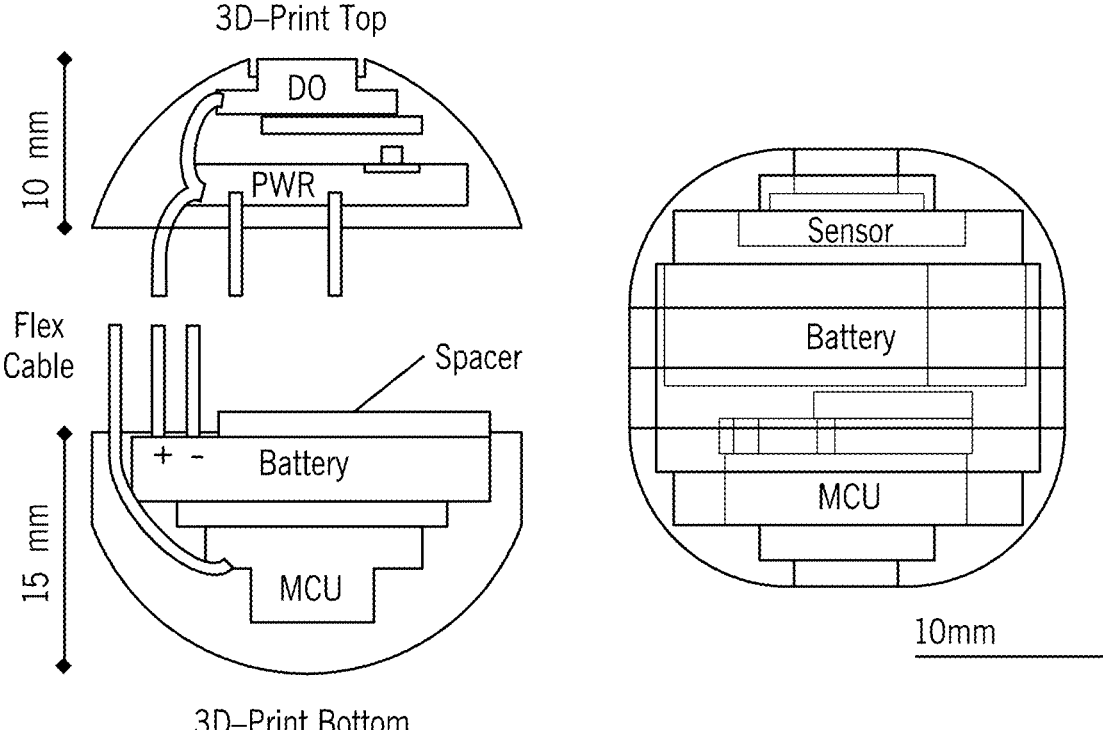
FIG. 48 shows a cross-sectional view of an embodiment of a bPod device which includes a two-part electronics module such as that shown in the bottom panel of FIG. 53, with an opened unit on the left and a sealed unit on the right.

Smaller bPod devices (e.g. less than 25 mm dia.) may be needed for certain applications. Accordingly, certain steps have been taken to fit all of the necessary components into a smaller package. FIG. 47 shows a first bPod electronics module that is a single board (top left) and a second bPod electronics module that is divided into two boards (bottom left), which permits miniaturization of the bPod device. A planar PCB layout is shown on the right in FIG. 47. FIG. 48 shows a cross-sectional view of an embodiment of a bPod device which includes a two-part electronics module such as that shown in the bottom panel of FIG. 47. The housing of the bPod is made (e.g. using 3D printing) in two parts: the first part of the housing may contain the microcontroller unit (MCU) and the power supply (battery), while the second part may contain the sensor (e.g. a dissolved oxygen (DO) sensor, see FIG. 49) and a power controller (PWR). A spacer may optionally be placed between the power supply and the power controller. The components contained within the first and second parts may be in communication with one another by one or more connector pins and/or flexible cables. The first and second parts of the housing may be connected using either a compression fit (e.g. an O-ring plus a mechanical coupler such as a bayonet connector) or using a combination of adhesive (e.g. an epoxy) and/or sealant (e.g. silicone). A two-part bPod is shown on the left in FIG. 48 in two parts prior to joining while another embodiment of a two-part unit is shown on the right in FIG. 48 after joining the two parts.

The part of the housing containing the sensor may include a slot or opening through which the sensor may gain access to the bioreactor contents. In the specific example shown in FIG. 48, the DO sensor is exposed to the contents of the bioreactor through a recessed window at the apex of the second part. Making the window slightly recessed can help protect the sensor from physical damage as it moves through the bioreactor environment. In various embodiments the bPod device sensors may include pressure measurement, a magnetometer, a DO, and/or RSSI measurements (relative received signal strength measurements in a wireless environment).

Figure 49:
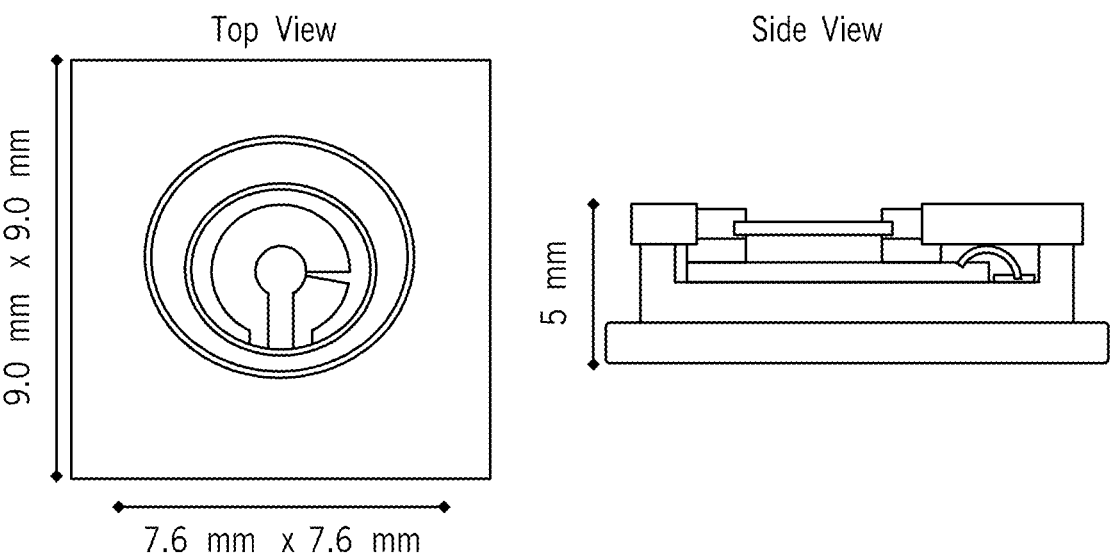
FIG. 49 shows an embodiment of a planar sensor.

FIG. 49 shows an embodiment of a planar sensor (DO in FIG. 48) including a top view (left) and a side view (right).

The planar sensor shown in FIG. 49 is about 5 mm high and the base is 9 mm×9 mm while the upper portion is 7.6 mm×7.6 mm. This sensor may include platinum working and counter electrodes and a silver reference. Three working electrode diameters were tested: 1 mm, 1.25 mm, and 1.5 mm. In general, the ratio of the counter electrode (CE) and working electrode (WE) was 2:1 to minimize sensor degradation. In the top view, the orange outer portion is a 3D-printed top; the light blue central regions (outlined in dark blue) are the two tape layers; the grey (outlined) portion is the sensor; the grey portion with no outline is the FEP membrane; the gold parts seen in the side view are soldered wire bonds; the dark blue section seen in the side view is the QFN package; and the green portion at the bottom in the side view is the PCB base.

Figure 50:
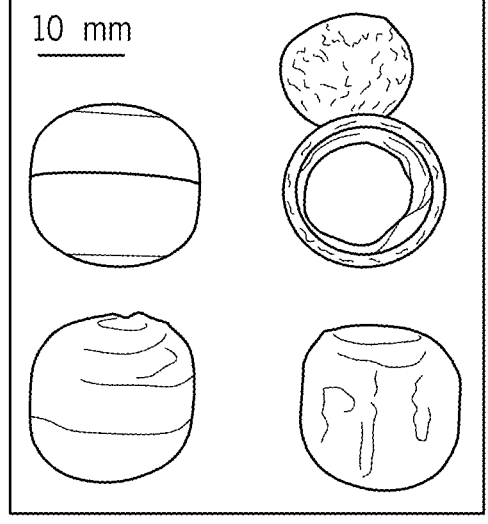
FIG. 50 shows embodiments of miniaturized bPods that were made using hard materials (e.g. Med610, top) or softer materials (e.g. PDMS, bottom).

FIG. 50 shows embodiments of miniaturized bPods that were made using hard materials (e.g. Med610, top) or softer materials (e.g. PDMS, bottom) after running tests in a bioreactor environment, although the outer surface of both materials tended to strip/tear after repeated collisions at 200 RPM.

Development of the bPod is directed to producing a device that is compact, self-contained, and long-lasting (e.g. can operate continuously for two weeks or longer) and has progressed from a benchtop prototype (approx. 60 mm dia., BGM121 chipset, no Bluetooth Mesh, card edge/glass electrode interface, lithium polymer battery), to a single board design (approx. 25-28 mm dia., BGM13S chipset, Bluetooth Mesh, wires to glass/flexible electrode interface, lithium polymer/lithium ion battery, BGM internal antenna for RF transmission, and optional magnetometer/pressure sens./temp./RSSI), to the miniaturized stacked board design (approx. 22-25 mm dia., BGM13S chipset, Bluetooth Mesh, wires to QFN package/flexible electrode interface, lithium ion/lithium thionyl. chlor. battery, patch antenna for RF transmission, and optional magnetometer/pressure sens./temp./RSSI). As noted above, a combination of one or more of a magnetometer, pressure sensor, and signal strength information from the RSSI may be used to track the location of the bPod device.

Power management is important for permitting the bPod devices to operate for sustained periods in an autonomous manner in a bioreactor environment, for example up to two weeks or longer; this a particular issue for the miniaturized bPod design since there is less space within the housing to hold power supplies (e.g. batteries). FIG. 51 provides information regarding power estimates for transmission current (output power) in low-power mode as well as at several transmission levels, and required capacity per week at various transmission levels. The antenna for the microcontroller can be operated at several output power levels. The higher the dBm the further the signal can propagate and the longer the communication distance. However this increased communication distance comes at the cost of higher current draw by the electronics, which when multiplied by the voltage gives the power calculation. FIG. 51 shows two possible estimations for device operation: 1) the "overestimation" that views the signal transfer during a measurement as a high pulse, and 2) models of the current at the given output power when transmitting and then of the device in low power mode when processing. The calculation shows the capacity of the battery required per week that is the sum of all the pulses over one week of time, assuming a measurement occurs every 5 minutes. We have a 225 mAh maximum capacity for two weeks, therefore a maximal power output can be estimated based on this capacity.

Figure 52:
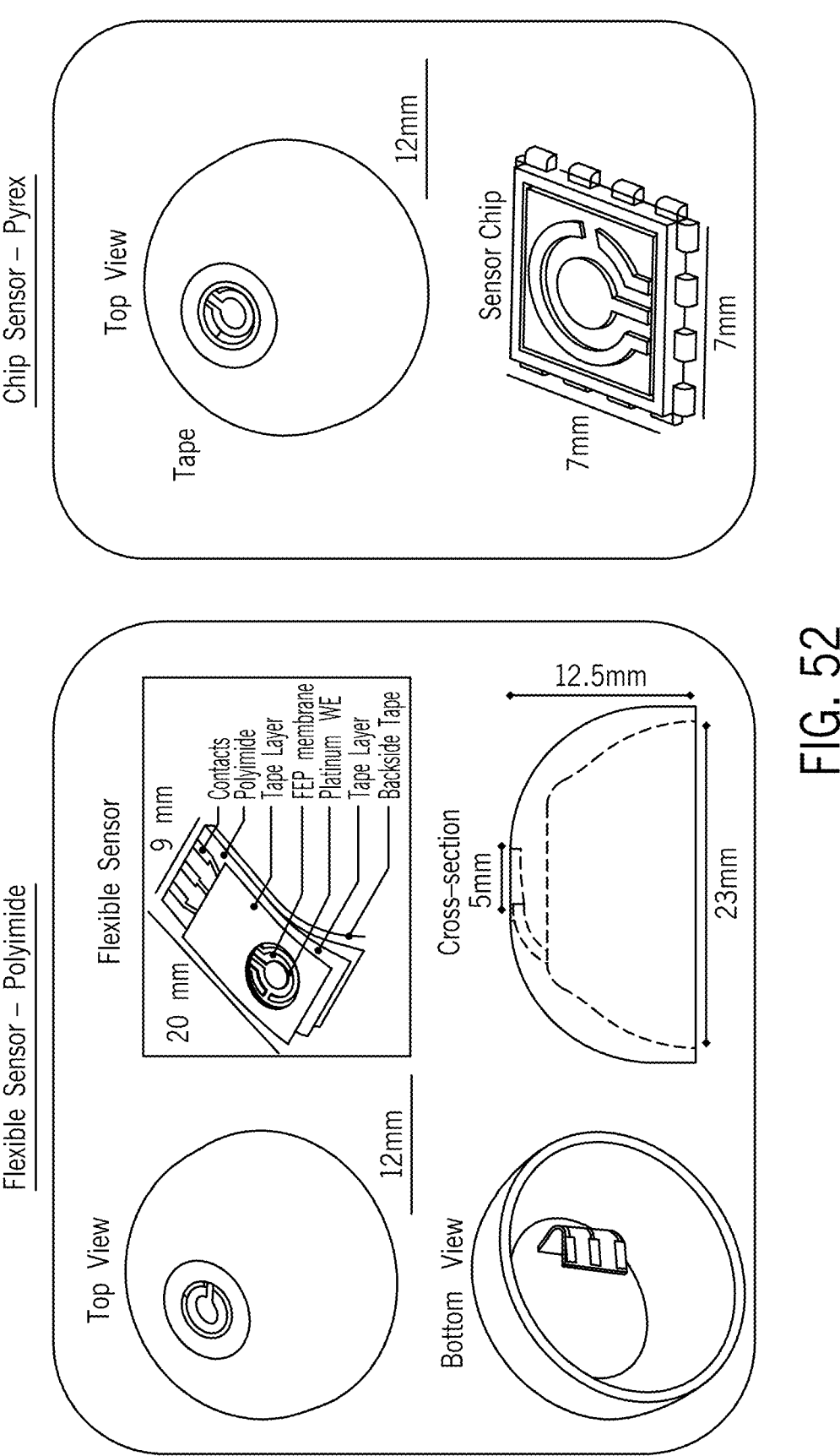
FIG. 52 shows designs for sensor interfaces on a miniaturized bPod device.

FIG. 52 shows designs for sensor interfaces on a miniaturized bPod device. The left panel of FIG. 52 shows a possible sensor interface for use with a flexible sensor. The right panel of FIG. 52 shows a possible sensor interface for use with a chip sensor (e.g. Pyrex). A multi-layer flexible sensor is an alternative approach to the chip sensor which is being explored for the stacked PCB embodiment. The flexible sensor includes a similar topology (mask metal pattern) as the single/planar chip sensor, however the flexible is fabricated on a polyimide (flexible) substrate. The sensor metal materials are platinum for the working and counter electrodes, and silver for the reference electrode. The sealing is the same as described in the tape based sensor interface: two layers of tape, a KCl electrolyte, and a FEP membrane. Metal adhesion and cutting of the substrate into sensors requires several additional assembly steps and is not initially preferred to using Pyrex as this is what the gold sensors were made of and all previous experimental results are derived from.

Figure 53:
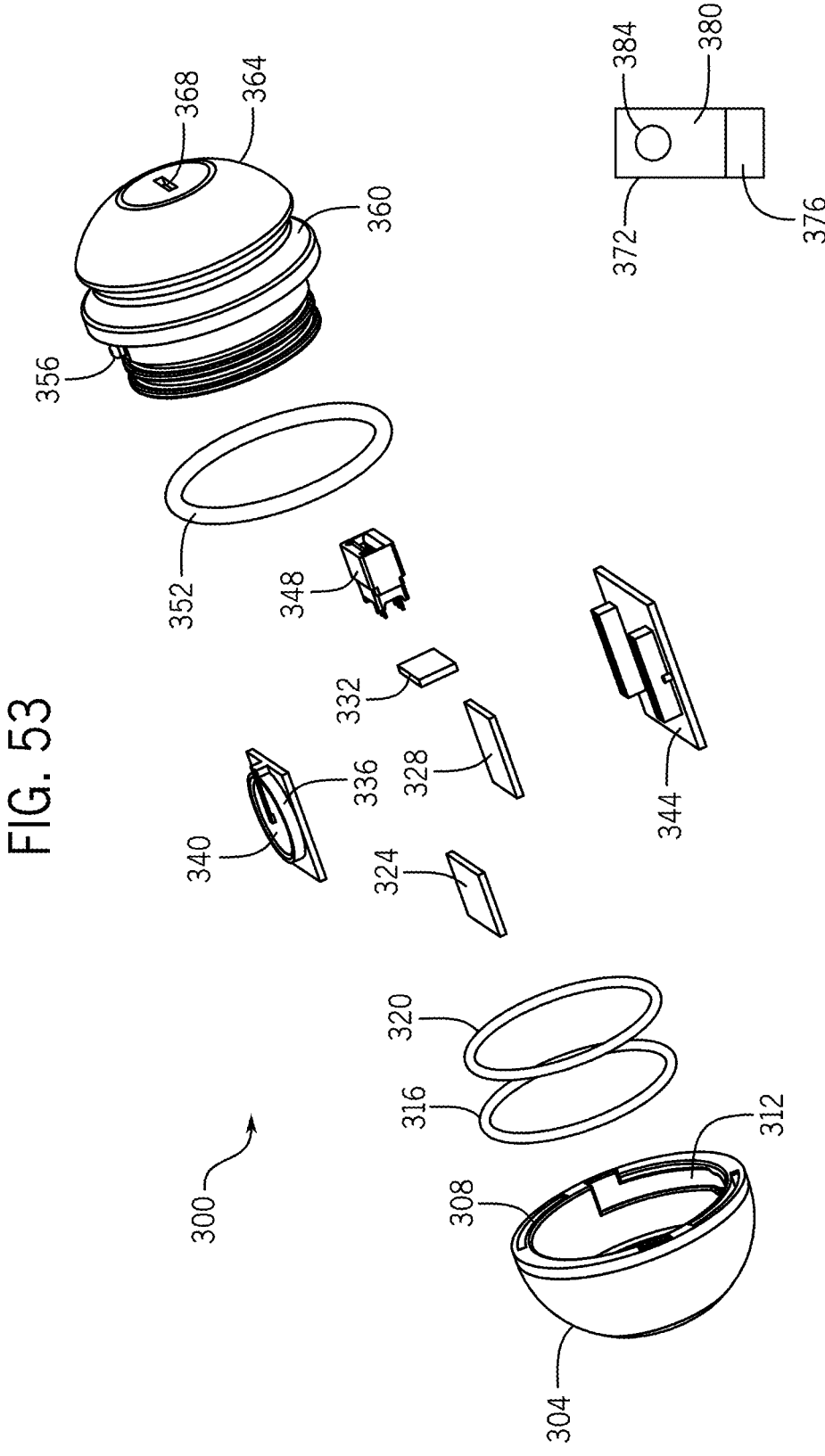
FIG. 53 shows an exploded view of a third generation bPod.

Referring now to FIG. 53, an exploded view of a third generation bPod 300 is shown. The third generation bPod 300 can have a diameter of 60 mm and a nominal wall thickness of 2 mm. The third generation bPod 300 can include a housing including a bottom portion 304 and a top portion 364 having a nominal thickness of 2 mm. The bottom portion 304 can be formed with a female bayonet connector 312 and be configured to accept a male bayonet connector 356 included in the top portion 364. The top portion 364 can be inserted into the bottom portion 304 with the male bayonet connector 356 angularly positioned to be inserted into the female bayonet connector 312. The top portion 364 can then be angularly rotated until the male bayonet connector 356 and the female bayonet connector 312 are interlocked in order to attach the top and bottom portions. The top portion 364 can include a grip 356 that can allow a user to more easily grip the top portion 364. The bottom portion 304 can include a weight infill slot 308 into which various weights can be inserted to adjust the weight and/or buoyancy of the third generation bPod 300.

The third generation bPod 300 can include two first size O-rings 316, 320 sized 48 mm in diameter and 2.5 mm thick. The first size O-rings 316, 320 can be used to provide a friction fit between the top portion 364 and the bottom portion 304 when the top portion 364 and the bottom portion 304 are interlocked. The third generation bPod 300 can include a second size O-ring 352 sized 54 mm in diameter and 4 mm thick. The second size O-ring 352 can be used to provide a press fit between the top portion 364 and the bottom portion 304 when the top portion 364 and the bottom portion 304 are interlocked.

The top portion 364 and the bottom portion 304 can house at least a portion of various electrical components configured to sense DO and communicate information wirelessly. The third generation bPod 300 can include a potentiostat 324 such as a LMP91000 from Texas Instruments, a voltage regulator 328, a battery holder 336 configured to hold a coin cell battery 340 such as a 20 mm CR2302 battery, and a card edge connector (CEC) 348. The potentiostat 324, the voltage regulator 328, the battery holder 336, the coin cell battery 340, and the card edge connector (CEC) 348 can be coupled to a microcontroller 344 with wireless communication capability such as a Silicon Labs BGM121 microcontroller. The microcontroller 344 can be further coupled to a DO sensor 372 arranged to at least partially protrude through the top portion 364 in order to be place in fluid communication with a liquid the third generation bPod 300 is positioned in. More specifically, the DO sensor 372 can extend through a slot 368 formed in the top portion 364. The slot 368 can be 10 mm wide by 2 mm high. The DO sensor 372 can include an FEP membrane 384 positioned at least partially outside the top portion 364 and configured to be placed in fluid communication with the liquid the third generation bPod 300 is positioned in. The DO sensor 372 can also include a gold electrode 376.

Figure 54:
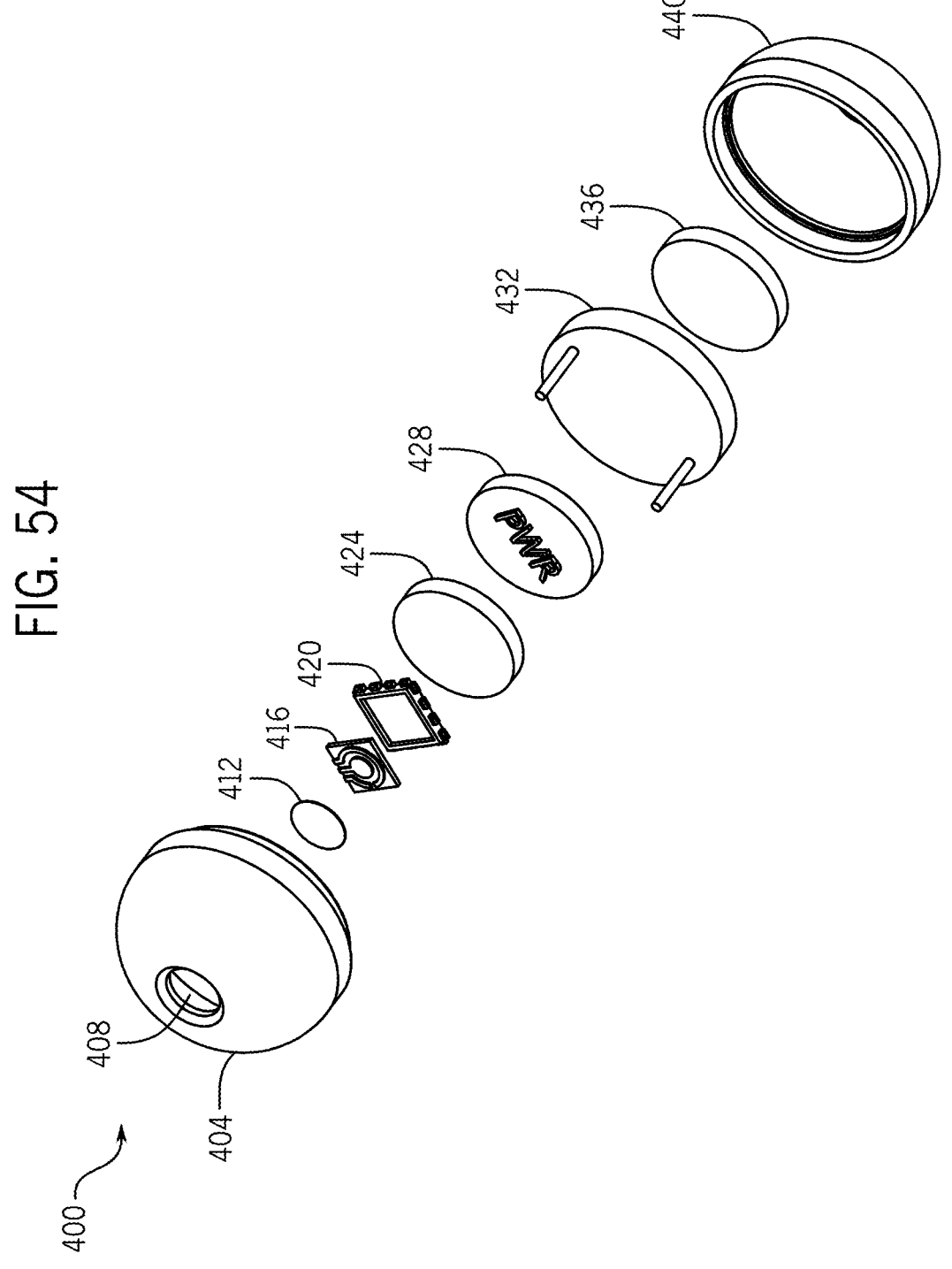
FIG. 54 shows an exploded view of a second generation bPod

Referring now to FIG. 54, an exploded view of a second generation bPod 400 is shown. The second generation 400 can have a diameter of 23.5 mm and a nominal wall thickness of 1.5 mm. The second generation bPod 400 can include a top portion 404 including a 6 mm diameter opening 408. The top portion 404 can be coupled to a bottom portion 440. The top portion and the bottom portion can each have a nominal wall thickness of 1.5 mm. The second generation bPod 400 can include a number of components housed at least partially within the top portion 404 and the bottom portion 440. The second generation bPod 400 can include an FEP membrane 412 arranged on top of a DO sensor die 416 including a platinum electrode. The DO sensor die 416 can be arranged on top of a 9 mm×9 mm open-air QFN package 420. The second generation bPod 400 can include a DO sensor PCB 424 coupled to the 9 mm×9 mm open-air QFN package 420. The DO sensor PCB 424 can be coupled to a power regulating PCB 428 coupled to a voltage regulator, a LMP91000 analog front end, a LP533HW pressure sensor, and a LIS3MDL microcontroller. The power regulating PCB 428 can be coupled to a coin cell battery 432 such as a 20 mm CR2032 battery. The second generation bPod 400 can further include an MCU PCB 436 coupled to a microcontroller such as a BGM135 microcontroller and an external antenna.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

What is claimed is:

1. A system for in-situ real-time wireless and continuous monitoring of a product process in a bioreactor, the system comprising:
a bioreactor tank containing a culture media within with a magnetic source disposed about the tank;
an external control device;
a plurality of neutral buoyant devices each independently free-floating within the culture media, each neutral buoyant device comprising:
a leak-proof housing, including a top half and a bottom half, the top half including a bayonet twist connector to form a leak proof seal with the bottom half, the top half including a central cutout;
an electrochemical cell including a bioprocess sensor, the bioprocess sensor including a first end having a plurality of contact pins and a second end having a sensor interface, the electrochemical cell being disposed in the central cutout of the housing with a leak-proof connection therebetween, the contact pins being disposed within the housing and the sensor interface disposed outside the housing and exposed to the culture media to sense a parameter of the product process in the culture media;
a card edge connector interfaced with the sensor, the card edge connector having leak-proof fittings located between the plurality of contact pins and the sensor interface of the bioprocess sensor;

a readout circuit directly interfaced with the sensor via the card edge connector, the readout circuit including an analog front end (AFE) potentiostat;
a power supply contained within the housing; and
an electronics module contained within the housing and in communication with the power supply and the bioprocess sensor, the electronics module comprising:
a wireless communication unit including a Bluetooth low energy (BLE) chipset having an internal antenna having a defined transmission frequency and a ground plane sized to fit within the housing and modulate the transmission frequency so as to form a Bluetooth mesh network with another neutral buoyant device in the plurality of neutral buoyant devices and the external control device over the modulated transmission frequency and through the culture media; and
a location tracking mechanism for identifying location information including spatial distributions of process parameters and product heterogeneities within the tank, the location tracking mechanism including an RSSI receiver, an on-board pressure sensor, and a magneto-resistive sensor, the RSSI receiver to determine an RSSI signal strength, the pressure sensor to monitor depth within the media and the magneto-resistive sensor to correlate an observed magnetic field between the magneto-resistive sensor and the magnetic source to determine the location of the neutral buoyant device within the tank; and
wherein each of the plurality of devices transmits over the Bluetooth mesh network to the external control device the sensed parameter of the product process, and location information associated with the parameter for identifying spatial distributions of the sensed parameters to target product heterogeneities within the bioreactor.

2. The system of claim 1, wherein the housing comprises a first element and a second element joined with a leak-proof fitting.

3. The system of claim 1, wherein the housing comprises a biocompatible material.

4. The system of claim 3, wherein the housing is formed using 3D printing of the biocompatible material.

5. The system of claim 1, wherein the bioprocess sensor comprises a dissolved oxygen sensor.

6. The system of claim 5, wherein the dissolved oxygen sensor comprises a Clark electrode bathed in electrolyte solution and covered by a gas-permeable membrane to define the sensor interface; disposed thereon defining a first portion an electrode surface, the electrolyte solution being trapped within a well formed by a electroplating tape, the gas permeable membrane being a fluorinated ethylene propylene gas permeable membrane separating the electrolyte solution from the culture media.

7. The system of claim 1, wherein the housing comprises a spherical shape.

8. The system of claim 7, wherein a diameter of the housing is in a range of 2 cm to 6 cm.

9. The system of claim 1, wherein the electronics module further comprises a power management unit.

10. The system of claim 1, wherein the wireless communication unit comprises a transmitter capable of emitting a signal strong enough to be detected by a receiver.

11. A method for in-situ real-time wireless and continuous monitoring of a product process, the method comprising:
providing a plurality of neutral buoyant devices into a bioreactor tank containing a culture media each neutral buoyant device independently free-floating within the culture media of the bioreactor tank, each neutral buoyant device including:

a leak-proof housing, including a top half and a bottom half, the top half including a bayonet twist connector to form a leak-proof seal with the bottom half, the top half including a central cutout;

an electrochemical cell including a bioprocess sensor having a first end with a plurality of contact pins and a second end having a sensor interface, the electrochemical cell being disposed in the central cutout of the housing with a leak-proof connection therebetween, the contact pins being disposed within the housing and the sensor interface disposed outside the housing;

a card edge connector interfaced with the sensor, the card edge connector having leak-proof fittings located between the plurality of contact pins and the sensor interface of the bioprocess sensor;

a readout circuit directly interfaced with the sensor via the card edge connector the readout circuit including an analog front end (AFE) potentiostat;

a power supply contained within the housing, and an electronics module contained within the housing and in communication with the power supply and the bioprocess sensor, the electronics module comprising:

a wireless communication unit including a Bluetooth low energy (BLE) chipset having an internal antenna having a defined transmission frequency and a ground plane sized to fit within the housing; and a location tracking mechanism including an RSSI receiver, an on-board pressure sensor, and a magneto-resistive sensor, sensing a parameter of the product process in the culture media by the plurality of neutral buoyant devices;

recording location information using the location tracking mechanism, the location information corresponding to spatial distributions of process parameters and product heterogeneities within the tank, the recording including using the RSSI receiver to determine an RSSI signal strength, using the pressure sensor to monitor depth within the media and using the magneto-resistive sensor to correlate an observed magnetic field between the magneto-resistive sensor and a magnetic source to determine the location of the neutral buoyant devices within the tank;

storing the data regarding the parameter and the corresponding location information in the electronics module of each neutral buoyant device; and transmitting through the culture media the sensed parameter of the product process and the location information associated with the parameter, the transmitting including modulating the transmission frequency of the internal antenna of one neutral buoyant device with the ground plane of the one neutral buoyant device; and forming a Bluetooth mesh network with another neutral buoyant device in the plurality of neutral buoyant devices.

12. The method of claim 11, wherein the bioprocess sensor comprises a dissolved oxygen sensor, and wherein sensing a parameter includes measuring dissolved oxygen levels.

13. The method of claim 11, wherein sensing a parameter further comprises: measuring the bioprocess parameter at least once per every 60 seconds.

14. The method of claim 11, further comprising receiving the information identifying the parameter at a receiver and displaying the information via a user interface of a display to a user.

15. The method of claim 14, further comprising making multiple transmissions of information identifying parameters, and receiving the transmissions at a receiver.

16. The method of claim 15, further comprising detecting a missing transmission from a given neutral buoyant device and reporting to the user that the sensor has a fault condition.

17. The method of claim 15, wherein the user interface displays to the user a visual spatial mapping of the parameters.

18. The method of claim 15 wherein the user interface alerts the user of a sensed parameter that is outside a predetermined desired range.

19. The method of claim 13, wherein sensing the parameter further comprises, for each of the more than one of the plurality of neutral buoyant devices:

measuring a signal output from the bioprocess sensor for a measurement duration to record a first measurement, wherein the measurement duration is about 5 seconds to about 30 seconds, then ceasing to measure such signal;

after a period of not measuring the signal output, measuring the signal output again for another measurement duration to record a second measurement; and associating the first measurement with location information of the sensor unit indicative of where the neutral buoyant device was located in the bioreactor tank during the associated measurement duration and associating the second measurement with location information of the sensor unit indicative of where the neutral buoyant device was located in the bioreactor tank during the associated measurement duration.

20. The system of claim 1, wherein the parameter measurement comprises a measurement duration comprising a duty cycle of about 10% to about 20%.

* * * * *